United States Patent
Bergman et al.

(10) Patent No.: US 10,421,743 B2
(45) Date of Patent: *Sep. 24, 2019

(54) TETRAHYDROISOQUINOLINES AS PRMT5 INHIBITORS

(71) Applicant: CTXT PTY LTD, Victoria (AU)

(72) Inventors: Ylva Elisabet Bergman, Victoria (AU); Michelle Ang Camerino, Victoria (AU); Scott Raymond Walker, Victoria (AU); Paul Anthony Stupple, Victoria (AU)

(73) Assignee: CTXT PTY LTD, Victoria (AU)

(*) Notice: Subject to any disclaimer, the term of this patent is extended or adjusted under 35 U.S.C. 154(b) by 0 days.

This patent is subject to a terminal disclaimer.

(21) Appl. No.: 16/081,696

(22) PCT Filed: Mar. 9, 2017

(86) PCT No.: PCT/EP2017/055529
§ 371 (c)(1),
(2) Date: Aug. 31, 2018

(87) PCT Pub. No.: WO2017/153513
PCT Pub. Date: Sep. 14, 2017

(65) Prior Publication Data
US 2019/0071425 A1    Mar. 7, 2019

(30) Foreign Application Priority Data
Mar. 9, 2016 (GB) .................................. 1604020.6

(51) Int. Cl.
*C07D 217/16* (2006.01)
*A61K 31/472* (2006.01)
(Continued)

(52) U.S. Cl.
CPC .......... *C07D 401/14* (2013.01); *C07D 217/16* (2013.01); *C07D 217/24* (2013.01);
(Continued)

(58) Field of Classification Search
CPC ............................. C07D 217/16; A61K 31/472
(Continued)

(56) References Cited

U.S. PATENT DOCUMENTS 4,880,802 A    11/1989 Schohe et al.
6,008,219 A    12/1999 Stemp et al.
(Continued)

FOREIGN PATENT DOCUMENTS

CN    102417483 A    4/2012
DE    261 153 A1    10/1988
(Continued)

OTHER PUBLICATIONS

Aggarwal et al., Cancer Cell 2010, 18, 329-340.
Berger, Nat. Cell Biol. 2008, 10, 1389-1390.
Chen et al., Proc. Natl. Acad. Sci. USA 2009, 106, 13433-13438.
Cho et al., EMBO J. 2012, 31, 1785-1797.
Durant et al., Cell Cycle 2009, 8, 801-802.
Gu et al., Biochem. J. 2012, 446, 235-241.
He et al., J. Transl. Med. 2013, 11:14.
Jansson et al., Nat. Cell Biol 2008, 10, 1431-1439.
Kanduri et al., Blood 2010, 115, 296-305.
Kim et al., Clin. Cancer Res. 2005, 11, 473-482.
Krause et al., Pharmacol. Ther. 2007, 113, 50-87.
Le Guezennec et al., Mol. Cell Biol. 2006, 26, 843-851.
Nicholas et al., Cancer Res. 2012, 72(8), Supplement, DOI : 10.1158/1538-7445.AM2012-LB-254.
(Continued)

*Primary Examiner* — Charanjit Aulakh
(74) *Attorney, Agent, or Firm* — Stites & Harbison PLLC; Richard S. Myers, Jr.

(57) ABSTRACT

A compound of formula (I) wherein: n is 1 or 2; p is 0 or 1; $R^{1a}$, $R^{1b}$, $R^{1c}$ and $R^{1d}$ are independently selected from the group consisting of H, halo, $C^{1-4}$ alkoxy, $C_{1-4}$ alkyl, $C_{1-4}$ fluoroalkyl, $C_{3-4}$ cycloalkyl, NH—$C_{1-4}$ alkyl and cyano; $R^{2a}$ and $R^{2b}$ are independently selected from the group consisting of: (i) F; (ii) H; (iii) Me; and (iv) $CH_2OH$; $R^{2c}$ and $R^{2d}$ are independently selected from the group consisting of: (i) F; (ii) H; (iii) Me; and (iv) $CH_2OH$; $R^{2e}$ is H or Me; $R^{3a}$ and $R^{3b}$ are independently selected from H and Me; $R^4$ is either H or Me; $R^5$ is either H or Me; $R^{6a}$ and $R^{6b}$ are independently selected from H and Me; A is either (i) optionally substituted phenyl; (ii) optionally substituted naphthyl; or (iii) optionally substituted $C_{5-12}$ heteroaryl; wherein when $R^{2e}$ is H, at least one of $R^{1a}$, $R^{1b}$, $R^{1c}$ and $R^{1d}$ is selected from $C_{1-4}$ alkoxy, $C_{2-4}$ alkyl, $C_{1-4}$ fluoroalkyl, $C_{3-4}$ cycloalkyl, NH—$C_{1-4}$ alkyl and cyano.

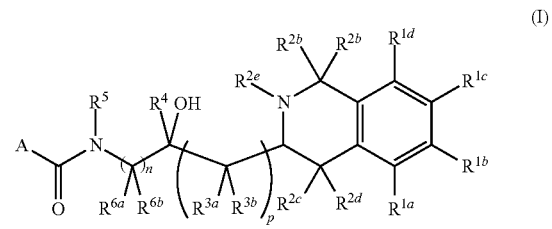

(I)

24 Claims, No Drawings

(51) Int. Cl.

| | |
|---|---|
| *C07D 401/14* | (2006.01) |
| *C07D 405/14* | (2006.01) |
| *C07D 401/12* | (2006.01) |
| *C07D 413/12* | (2006.01) |
| *C07D 471/04* | (2006.01) |
| *C07D 498/08* | (2006.01) |
| *C07D 217/24* | (2006.01) |
| *C07D 491/08* | (2006.01) |
| *A61P 35/00* | (2006.01) |

(52) U.S. Cl.
CPC ......... *C07D 401/12* (2013.01); *C07D 405/14* (2013.01); *C07D 413/12* (2013.01); *C07D 471/04* (2013.01); *C07D 491/08* (2013.01); *C07D 498/08* (2013.01); *A61P 35/00* (2018.01)

(58) Field of Classification Search
USPC .......................................... 546/146; 514/307
See application file for complete search history.

(56) References Cited

U.S. PATENT DOCUMENTS

| | | | |
|---|---|---|---|
| 6,046,210 | A | 4/2000 | Stemp et al. |
| 6,274,593 | B1 | 8/2001 | Johns et al. |
| 6,579,892 | B1 | 6/2003 | Starck et al. |
| 9,856,252 | B2 | 1/2018 | Stupple et al. |
| 10,005,792 | B2 | 6/2018 | Bergman et al. |
| 2005/0101647 | A1 | 5/2005 | Oda et al. |
| 2005/0107398 | A1 | 5/2005 | Mach et al. |
| 2006/0235037 | A1 | 10/2006 | Purandare et al. |
| 2010/0069431 | A1 | 3/2010 | Iwata et al. |
| 2016/0222005 | A1 | 8/2016 | Stupple et al. |
| 2017/0283407 | A1 | 10/2017 | Foitzik et al. |
| 2017/0298075 | A1 | 10/2017 | Berman et al. |

FOREIGN PATENT DOCUMENTS

| | | |
|---|---|---|
| EP | 1008592 A2 | 6/2000 |
| GB | 2286395 A | 6/1995 |
| WO | WO 96/30333 A1 | 10/1996 |
| WO | WO 97/43262 A1 | 11/1997 |
| WO | WO 98/49145 A1 | 11/1998 |
| WO | WO 03/035065 A1 | 5/2003 |
| WO | WO 03/082186 A2 | 10/2003 |
| WO | WO 2004/016611 A1 | 2/2004 |
| WO | WO 2004/024897 A2 | 3/2004 |
| WO | WO 2005/030206 A1 | 4/2005 |
| WO | WO 2005/042495 A1 | 5/2005 |
| WO | WO 2006/008133 A2 | 1/2006 |
| WO | WO 2006/080821 A1 | 8/2006 |
| WO | WO 2009/005551 A2 | 1/2009 |
| WO | WO 2009/113085 A1 | 9/2009 |
| WO | WO 2009/139076 A1 | 11/2009 |
| WO | WO 2010/025295 A2 | 3/2010 |
| WO | WO 2012/108689 A2 | 8/2012 |
| WO | WO 2014/100695 A1 | 6/2014 |
| WO | WO 2014/100716 A1 | 6/2014 |
| WO | WO 2014/100719 A2 | 6/2014 |
| WO | WO 2014/100730 A1 | 6/2014 |
| WO | WO 2014/100734 A1 | 6/2014 |
| WO | WO 2014/100764 A2 | 6/2014 |
| WO | WO 2015/198229 A1 | 12/2015 |
| WO | WO 2015/200677 A2 | 12/2015 |
| WO | WO 2016/034671 A1 | 3/2016 |
| WO | WO 2016/034673 A1 | 3/2016 |
| WO | WO 2016/034675 A1 | 3/2016 |

OTHER PUBLICATIONS

Pal et al., Mol Cell. Biol. 2003, 23, 7475-7487.
Pal et al., EMBO J. 2007, 26, 3558-3569.
Pollack et al., J. Biol. Chem. 1999, 274, 31531-31542.
Powers et al., Cancer Res. 2011, 71, 5579-5588.
Rank et al., Blood 2010, 116, 1582-1592.
Scoumanne et al., Nucleic Acids Res. 2009, 37, 4965-4976.
Wang et al., Mol. Cell Biol. 2008, 28, 6262-6277.
Zhongping et al., PLoS ONE 2012, 7(8): e44033.
Zhang et al., J. Pestic. Sci. 2012, 37, 338-341.
Secci et al., J. Heterocyclic Chem. 2012, 49, 1187-1195.
Rostamizadeh et al., Synth. Commun. 2011, 41, 1794-1804.
Chen et al., Heterocycl. Commun. 2010, 16, 123-135.
Göker et al., J. Heterocyclic Chem. 2009, 46, 936-948.
Kaynak et al., Struct. Chem. 2008, 19, 477-480.
Kuş et al., Ankara Ecz. Fak. Derg. 2006, 35, 237-244.
Vijayakumar et al., J. Chem. Pharm Res. 2010, 2(4), 215-224.
Richards et al., Eur. J. Med. Chem. 2006, 41, 950-969.
Mach et al., ChemBioChem 2004, 5, 508-518.
Braun et al., Ber. Dtsch. Chem. Ges., B 1926, 59, 2416-2425.
Zajdel et al., QSAR Comb. Sci. 2007, 26, 215-219.
Chan-Penebre et al., Nature Chemical Biology, 2015, 11, 432-437.

ns as PRMT5
TETRAHYDROISOQUINOLINES AS PRMT5 INHIBITORS

CROSS REFERENCE TO RELATED APPLICATIONS

This application is a § 371 National State Application of PCT/EP2017/055529 filed Mar. 9, 2017 which claims priority to GB 1604020.6 filed Mar. 9, 2016.

The present invention relates to C-alkyl bicyclic amines and their use as pharmaceuticals, and in particular, in treating cancer and hemoglobinopathies.

BACKGROUND TO THE INVENTION

Post-translational modification of proteins is a hallmark of signal transduction where cells are able to react quickly to changes or events in the cellular environment. Post-translational modification of proteins expands the structural and functional diversity of the proteome. The role of acetylation and phosphorylation of proteins has been extensively studied as highly reversible reactions for fine-tuning responses to external stimuli or changes in the environmental conditions. Recently, the importance of other types of protein modifications, including ubiquitination and methylation has begun to be recognized.

The methylation of proteins and the enzymes that carry out these reactions has increased the dimensions of gene regulation by marking genes that are transcriptionally active or silenced. Protein methylation can occur on amino acids such as lysine, arginine, histidine, or proline, and on carboxy groups.

Arginine methylation of mainly nuclear proteins is an important post-translational modification process involved in structural remodelling of chromatin, signal transduction, cellular proliferation, nucleocytoplasmic shuttling, translation, gene transcription, DNA repair, RNA processing, or mRNA splicing.

Methylation of proteins at arginine residues is catalysed by Protein Arginine Methyltransferase enzymes. The Protein Arginine Methyl Transferase (PRMT) family of enzymes are evolutionarily conserved between organisms but differ in the number of members in different organisms.

There are eleven members of the human PRMT family, eight of which have known enzymatic activity and target substrates. With the exception of PRMT2 and two recently identified putative PRMT genes (PRMT10 and PRMT11), all remaining proteins of the family possess enzymatic arginine methylation activity.

PRMTs are subdivided into two types based on the methylation that they catalyse at the guanidinium group of arginine residues of substrate proteins. There are three nitrogens in the guanidinium group, potentially all of which could be methylated; the two ψ-guanidino nitrogen atoms and the internal δ-guanidino nitrogen atom. Mono-methylation and dimethylation of arginine (MMA and DMA) is found in mammalian cells at one or both of the two ψ-guanidino nitrogen atoms; dimethylation may be either symmetric or asymmetric. The third methylated arginine is generated by monomethylation of the internal δ-guanidino nitrogen atom of arginine and has so far been documented only in yeast proteins. Type I PRMT enzymes catalyse the formation of MMA and asymmetric dimethylarginine by di-methylating the same nitrogen atom of the guanidinium group, whereas Type II PRMT enzymes catalyse the formation of MMA and symmetric di-methylarginine by mono-methylating each of the terminal nitrogen atoms. Type III enzymes methylate the internal δ-guanidino nitrogen atom. Of the eight well characterised human PRMTs, PRMT1, 3, 4, 6 and 8 are Type I enzymes, and PRMT5, 7 and 9 are Type II enzymes.

PRMTs catalyse the methylation of the guanidino nitrogen atoms of arginine residues through the transfer of a methyl group from S-adenosyl methionine (SAM). A by-product of the enzymatic methylation step is S-adenosyl-L-homocysteine (AdoHcy), which is hydrolyzed to adenosine and homocysteine by AdoHcy hydrolase (Krause et al., 2007).

PRMT5

PRMT5 (aka JBP1, SKB1, IBP72, SKB1his and HRM-TIL5) is a Type II arginine methyltransferase, and was first identified in a two-hybrid search for proteins interacting with the Janus tyrosine kinase (Jak2) (Pollack et al., 1999).

PRMT5 plays a significant role in control and modulation of gene transcription. Inter alia, PRMT5 is known to methylate histone H3 at Arg-8 (a site distinct from that methylated by PRMT4) and histone H4 at Arg-3 (the same site methylated by PRMT1) as part of a complex with human SWI/SNF chromatin remodelling components BRG1 and BRM.

In addition to direct repressive histone marks induced by PRMT5, the enzyme's role in gene silencing is also mediated through the formation of multiprotein repressor complexes that include NuRD components, HDACs, MDB proteins and DNA methyltransferases, (Rank et al., 2010; Le Guezennec et al., 2006; Pal et al., 2003).

PRMT5 is involved in the methylation and functional modulation of the tumour suppressor protein p53. See (Berger, 2008; Durant et al., 2009; Jansson et al., 2008; Scoumanne et al., 2009). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harbouring wild type p53, by way of inhibiting mechanisms that suppress its function leads to growth arrest and apoptosis, and is regarded as a potentially effective means of tumour suppression.

p53 target genes have two alternative downstream effects: either they pause the cell cycle, allowing the DNA to be repaired, or, if repair is not possible, they activate processes leading to apoptosis (programmed cell death). How p53 'chooses' between these distinct outcomes is a central question in the field of tumour biology.

p53 is replete with post-translational modifications. Phosphorylation was one of the first post-translational modifications to be clearly defined on p53. In the last decade it has become additionally clear that p53 is modified not only by phosphorylation, but that it is extensively modified by lysine acetylation and methylation, among other modifications. Indeed, besides histone proteins p53 is the most common protein substrate known for these post-translational modifications. However, despite the plethora of post-translational modifications, p53 has not been identified, until recently, as a substrate for arginine methylation.

Jansson et al (Jansson et al., 2008) discovered that PRMT5 is physically associated with a p53 cofactor called Strap. A co-factor complex that contains Strap et al binds to p53 in response to DNA damage. Jansson et al demonstrated that PRMT5 methylates p53 in vitro, and mapped the sites of methylation (R333, R335 and R337). They developed an antibody that specifically detects p53 methylated on these sites and confirmed that p53 is methylated in vivo. Jansson et al went on to show that p53 methylation requires PRMT5 and is increased in response to etoposide, a DNA damaging agent.

The role of PRMT5 and p53 arginine methylation on cell cycle regulation and DNA damage response have been explored by both Jansson et al and Scoumanne et al (Jansson et al., 2008; Scoumanne et al., 2009). Although some differences are evident between the results from the two groups in respect of cell cycle regulation in unperturbed cells (which may be ascribed to cell type specific effects and/or the actual nature of the experimental arrangements), both groups report similar results with respect to the DNA damage response.

In response to DNA damage, caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in a reduced level of p21, a key p53 target gene that regulates cell cycle arrest during the p53 response and MDM2, a p53 E3 ubiquitin ligase, but not PUMA, NOXA, AIP1 & APAF1, p53 target genes linked to apoptosis.

Knockdown of PRMT5 (but not PRMT1 or CARM1/PRMT4) results in decreased p53 stabilisation, decreased basal p53 levels, and decreased p53 oligomerisation, and also decreased expression of eIF4E a major component of translational machinery involved in ribosome binding to mRNA. Indeed, eIF4E is a potent oncogene, which has been shown to promote malignant transformation in vitro and human cancer formation.

Knockdown of PRMT5 would be expected to lead to a reduction in the level of arginine methylated p53. Consistent with arginine methylation status of p53 influencing the p53 response (reduced arginine methylation biasing the response to proapoptotic), Jannson et al showed that a p53 mutant in which each of the three critical arginine residues were substituted with lysine (p53KKK) retained the ability to induce apoptosis but its cell cycle arrest activity was significantly compromised.

Moreover, pS3KKK also has a significantly reduced ability to induce transcription of p21, by contrast with APAF1. The promoter binding specificity of wild-type p53 to key target genes is also significantly affected by arginine methylating status: Knockdown of PRMT5 results in decreased p53 binding to the promoter regions of the p21 and (intriguingly) PUMA genes, but does not affect p53 binding to the promoter regions of NOXA or APAF1.

Taken together, it would seem that PRMT5 is a pro-survival factor, which regulates cell proliferation in unstressed conditions and modulates the p53 response during DNA damage. In particular, knockdown of PRMT5, leading to a reduction in the levels of arginine methylated p53, appears to bias the p53 DNA damage response to proapoptotic as opposed to cell cycle arrest.

PRMT5 is further linked to cancers in that it is aberrantly expressed in around half of human cancer cases. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including CLL are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukaemia cell lines; and B-CLL cell lines, relative to normal CD19+ B lymphocytes (Pal et al., 2007; Wang et al., 2008). Intriguingly, despite elevated levels of PRMT5 protein in these tumour cells, the levels of PRMT5 mRNA are reduced (by a factor of 2-5). Translation of PRMT5 mRNA is however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumour suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

PRMT5 Function and Hemoglobinopathies

Hemoglobin is a major protein in red blood cells and is essential for the transport of oxygen from the lungs to the tissues. In adult humans, the most common hemoglobin type is a tetramer called hemoglobin A, consisting of two $\alpha$ and two $\beta$ subunits. In human infants, the hemoglobin molecule is made up of two $\alpha$ and two $\gamma$ chains. The gamma chains are gradually replaced by subunits as the infant grows. The developmental switch in human ß-like globin gene subtype from foetal ($\gamma$) to adult (ß) that begins at birth heralds the onset of the hemoglobinopathies ß-thalassemia and sickle cell disease (SCD). In ß-thalassemia the adult chains are not produced. In SCD a point mutation in the coding sequence in the ß globin gene leads to the production of a protein with altered polymerisation properties. The observation that increased adult $\gamma$-globin gene expression (in the setting of hereditary persistence of foetal hemoglobin (HPFH) mutations) significantly ameliorates the clinical severity of ß-thalassemia and SCD has prompted the search for therapeutic strategies to reverse $\gamma$-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the $\gamma$-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as ß-thalassemia and Sickle Cell Disease (SCD).

The present inventors have developed particular substituted β-hydroxy amides inhibit the activity of PRMT5 and therefore may be of use in treating conditions ameliorated by the inhibition of the activity of PRMT5.

SUMMARY OF THE INVENTION

A first aspect of the present invention provides a compound of formula I:

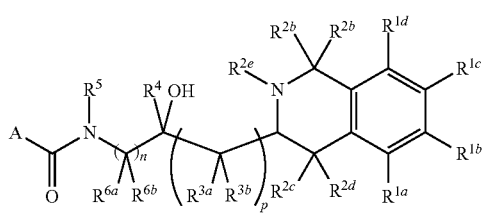

(I)

wherein:
n is 1 or 2;
p is 0 or 1;
$R^{1a}$, $R^{1b}$, $R^{1c}$ and $R^{1d}$ are independently selected from the group consisting of H, halo, $C_{1-4}$ alkoxy, $C_{1-4}$ alkyl, $C_{1-4}$ fluoroalkyl, $C_{3-4}$ cycloalkyl, NH—$C_{1-4}$ alkyl and cyano;
$R^{2a}$ and $R^{2b}$ are independently selected from the group consisting of:
(i) F;
(ii) H;
(iii) Me; and
(iv) $CH_2OH$;
$R^{2c}$ and $R^{2d}$ are independently selected from the group consisting of:
(i) F;
(ii) H;
(iii) Me; and
(iv) $CH_2OH$;
$R^{2e}$ is H or Me;
$R^{3a}$ and $R^{3b}$ are independently selected from H and Me;
$R^4$ is either H or Me;
$R^5$ is either H or Me;
$R^{6a}$ and $R^{6b}$ are independently selected from H and Me;
A is either
(i) optionally substituted phenyl;
(ii) optionally substituted naphthyl; or
(iii) optionally substituted $C_{5-12}$ heteroaryl;
wherein when $R^{2e}$ is H, at least one of $R^{1a}$, $R^{1b}$, $R^{1c}$ and $R^{1d}$ is selected from $C_{1-4}$ alkoxy, $C_{2-4}$ alkyl, $C_{1-4}$ fluoroalkyl, $C_{3-4}$ cycloalkyl, NH—$C_{1-4}$ alkyl and cyano.

A second aspect of the present invention provides a compound of the first aspect for use in a method of therapy. The second aspect also provides a pharmaceutical composition comprising a compound of the first aspect and a pharmaceutically acceptable excipient.

A third aspect of the present invention provides a method of treatment of cancer, comprising administering to a patient in need of treatment, a compound of the first aspect of the invention or a pharmaceutical composition of the first aspect of the invention. The third aspect of the present invention also provides the use of a compound of the first aspect of the invention in the manufacture of a medicament for treating cancer, and a compound of the first aspect of the invention or pharmaceutical composition thereof for use in the treatment of cancer.

As described below, the compound of the first aspect may be administered simultaneously or sequentially with radiotherapy and/or chemotherapy in the treatment of cancer.

A fourth aspect of the present invention provides a method of treatment of hemoglobinopathies, comprising administering to a patient in need of treatment, a compound of the first aspect of the invention or a pharmaceutical composition of the first aspect of the invention. The fourth aspect of the present invention also provides the use of a compound of the first aspect of the invention in the manufacture of a medicament for treating hemoglobinopathies, and a compound of the first aspect of the invention or pharmaceutical composition of the first aspect of the invention for use in the treatment of hemoglobinopathies.

Definitions $C_{5-12}$ heteroaryl: The term "$C_{5-12}$ heteroaryl" as used herein, pertains to a monovalent moiety obtained by removing a hydrogen atom from an aromatic structure having from 5 to 12 rings atoms, of which from 1 to 3 are ring heteroatoms. The term 'aromatic structure' is used to denote a single ring or fused ring systems having aromatic properties, and the term 'ring heteroatom' refers to a nitrogen, oxygen or sulphur atom.

In this context, the prefixes (e.g. $C_{5-12}$, $C_{5-6}$, etc.) denote the number of atoms making up the aromatic structure, or range of number of atoms making up the aromatic structure, whether carbon atoms or heteroatoms.

Examples of $C_{5-12}$ heteroaryl structures include, but are not limited to, those derived from:
$N_1$: pyrrole (azole) ($C_5$), pyridine (azine) ($C_6$); pyridone ($C_6$); indole ($C_9$); quinoline ($C_{10}$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_1S_1$: thiazole ($C_5$), isothiazole ($C_5$);
$N_2S_1$: thiadiazole ($C_5$)
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$); benzimidazole ($C_9$)
$N_3$: triazole ($C_5$), triazine ($C_6$).

Cyano: The term "cyano" as used herein pertains to a group —CN.

Optional Substituents

The optional substituents for the phenyl, naphthyl and $C_{5-12}$ heteroaryl groups in A may be selected from the following groups.

$C_{1-4}$ alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms.

Examples of saturated alkyl groups include, but are not limited to, methyl($C_1$), ethyl($C_2$), propyl($C_3$), and butyl($C_4$).

Examples of saturated linear alkyl groups include, but are not limited to, methyl($C_1$), ethyl($C_2$), n-propyl($C_3$), and n-butyl($C_4$).

Examples of saturated branched alkyl groups include iso-propyl($C_3$), iso-butyl($C_4$), sec-butyl($C_4$) and tert-butyl ($C_4$).

The term "$C_{2-4}$ alkyl" as used herein, pertains to a monovalent moiety obtained by removing a hydrogen atom from a carbon atom of a saturated hydrocarbon compound having from 2 to 4 carbon atoms.

$C_{1-4}$ fluoroalkyl: The term "$C_{1-4}$ fluoroalkyl" refers to a $C_{1-4}$ alkyl group as defined above where one of more of the hydrogen atoms is replaced by a fluoro. Examples of $C_{1-4}$ fluoroalkyl include, but are not limited to, —$CF_3$, $CF_2H$, —$C_2F_5$, and —$C_2F_4H$.

$C_{3-6}$ cycloalkyl: the term '$C_{3-6}$ cycloalkyl' as used herein, pertains to a monovalent moiety obtained by removing a hydrogen atom from a carbon atom of a saturated cyclic core having 3, 4, 5 or 6 atoms in the cyclic core all of which are carbon atoms. Examples of $C_{3-6}$ cycloalkyl include, but are not limited to, cyclopropyl, cyclohexyl and cyclopentyl.

$C_{3-4}$ cycloalkyl: the term '$C_{3-4}$ cycloalkyl' as used herein, pertains to a monovalent moiety obtained by removing a hydrogen atom from a carbon atom of a saturated cyclic core having 3 or 4 atoms in the cyclic core all of which are carbon atoms. Examples of $C_{3-4}$ cycloalkyl include cyclopropyl and cyclobutyl.

$C_{5-6}$ heteroaryl: the term $C_{5-6}$ heteroaryl as used herein, pertains to a monovalent moiety obtained by removing a hydrogen atom from a ring atom of an aromatic structure having between one and three atoms that are not carbon forming part of said ring. Wherein, those atoms that are not carbon can be chosen independently from the list nitrogen, oxygen and sulphur. The group may be substituted by one or more $C_{1-4}$ alkyl groups.

Examples of $C_{5-6}$ heteroaryl groups include, but are not limited to, groups derived from:

$N_1$: pyridine ($C_6$);
$N_1O_1$: oxazole ($C_5$), isoxazole ($C_5$);
$N_2O_1$: oxadiazole (furazan) ($C_5$);
$N_2S_1$: thiadiazole ($C_5$)
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$).

$C_{5-6}$ heteroaryl methyl: —$CH_2$—($C_{5-6}$ heteroaryl), wherein $C_{5-6}$ heteroaryl is as defined above.

$C_{4-6}$ heterocyclyl: The term "$C_{4-6}$ heterocyclyl" as used herein, pertains to a monovalent moiety obtained by removing a hydrogen atom from a ring atom of a monocyclic heterocyclic compound, which moiety has from 4 to 6 ring atoms; of which from 1 to 2 atoms are heteroatoms, chosen from oxygen or nitrogen.

In this context, the prefixes (e.g. $C_{4-6}$) denote the number of ring atoms, or range of number of ring atoms, whether carbon atoms or heteroatoms.

Examples of $C_{4-6}$ heterocyclyl groups include, but are not limited to, those derived from:

$N_1$: azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$N_2$: diazetidine ($C_4$), imidazolidine ($C_5$), pyrazolidine (diazolidine) ($C_5$), imidazoline ($C_5$), pyrazoline (dihydropyrazole) ($C_5$), piperazine ($C_6$);
$O_1$: oxetane ($C_4$), tetrahydrofuran ($C_5$); oxane ($C_6$);
$O_2$: dioxetane ($C_4$), dioxolane ($C_5$); dioxane ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$).

Those $C_{4-6}$ heterocyclyl groups which include a N atom may be substituted on this atom by an acyl group, and in particular, by —C(=O)Me.

$C_{4-6}$ heterocyclyl methyl: —$CH_2$—($C_{4-6}$ heterocyclyl), wherein $C_{4-6}$ heterocyclyl is as defined above.

Phenyl: —$C_6H_5$, wherein the phenyl may itself be optionally substituted by one or more $C_{1-4}$ alkyl groups, one or more $C_{1-4}$ fluoroalkyl groups, one or more $C_{1-4}$ alkoxy groups, one or more halo substituents and one or more cyano substituents.

Benzyl: —$CH_2$-Phenyl, wherein phenyl is as defined above.

Halo: The term "halo" as used herein, refers to a group selected from fluoro, chloro, bromo and iodo.

Amido: —C(=O)NRR' wherein R and R' are independently selected from H, $C_{1-4}$ alkyl and $C_{4-6}$ heterocyclyl as defined above, or together form a group selected from (—$CH_2$—)$_n$ and —($CH_2$)$_m$—X—($CH_2$)$_p$—, where n=3-6, m and p=0-4, and X=O or NH. X may also be N—S(=O)$_2$, S or S(=O)$_2$. The cyclic amido groups may also be bridged by a further group selected from (—$CH_2$—)$_{n1}$ and —($CH_2$)$_{m1}$—X—($CH_2$)$_{p1}$—, where n1 is 1-3 and m1 and p1 are 1-3. The cyclic amido groups may also be further substituted by one, two or more hydroxy, oxo, $C_{1-2}$ alkyl, $C_{1-2}$ alkyl-$C_{1-2}$ alkoxy, $C_{1-2}$ alkyl-hydroxy and $C_{1-2}$ alkoxy groups or one spiro $C_{4-6}$ heteroaryl or spiro $C_{4-6}$ cycloalkyl group or be fused to an $C_{5-7}$ aromatic ring. Examples of amido groups include, but are not limited to, —C(=O)$NH_2$, —C(=O)$NMe_2$, —C(=O)NHMe, —C(=O)NHCH($CH_3$)$_2$,

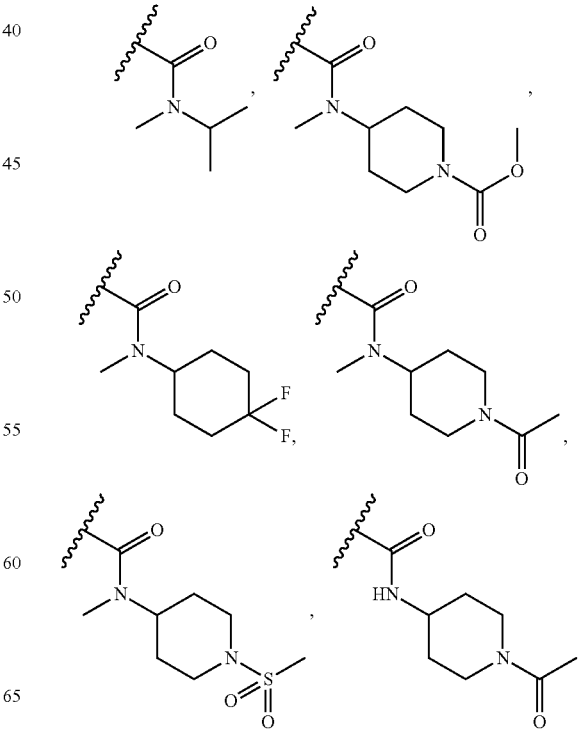

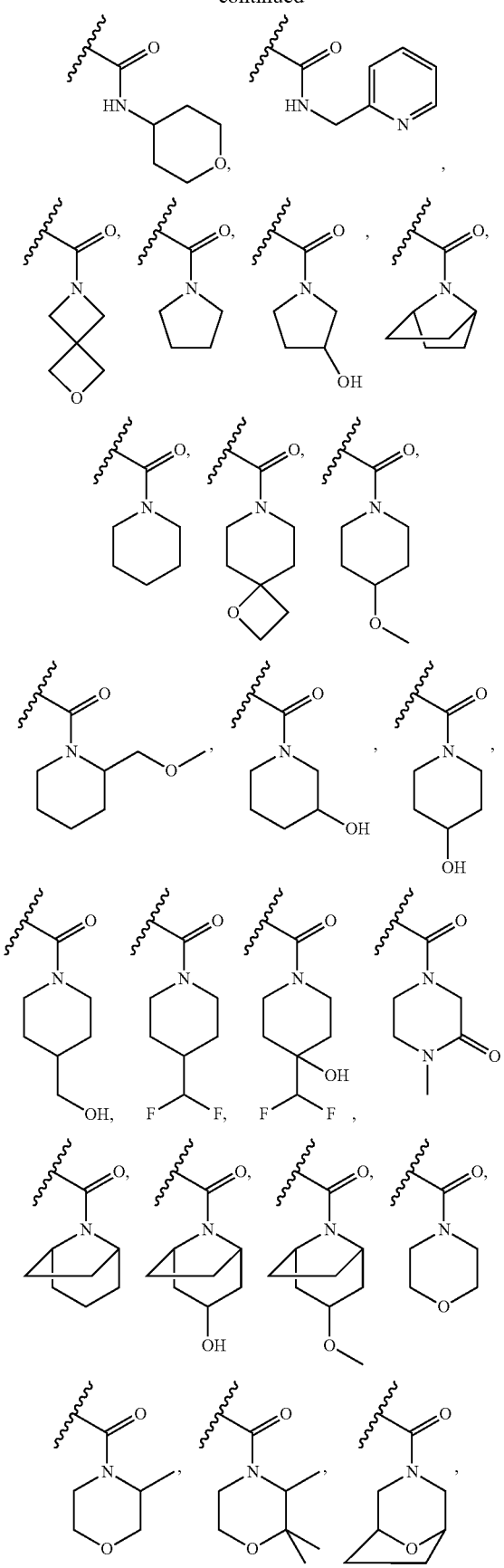
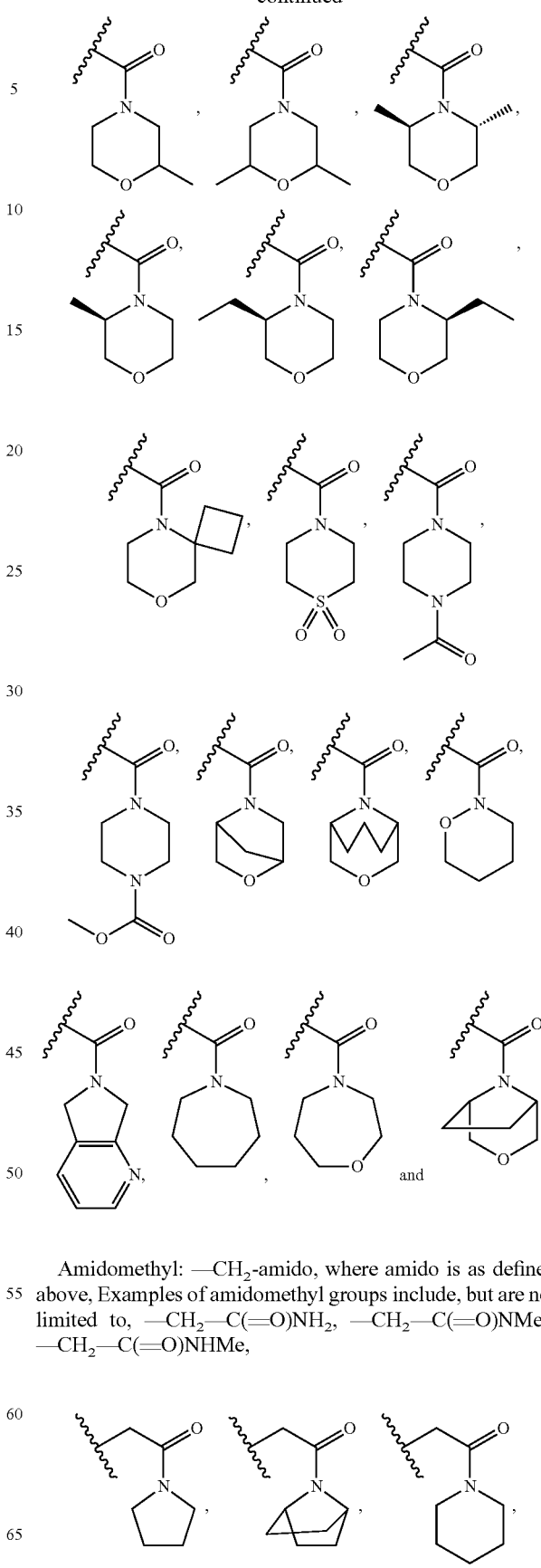
Amidomethyl: —CH$_2$-amido, where amido is as defined above, Examples of amidomethyl groups include, but are not limited to, —CH$_2$—C(=O)NH$_2$, —CH$_2$—C(=O)NMe$_2$, —CH$_2$—C(=O)NHMe,

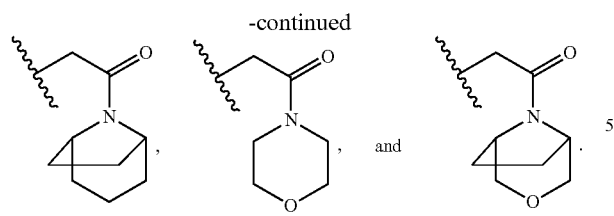

Acylamido: —NR(C═O)R' wherein R and R' are independently selected from H, $C_{1-4}$ alkyl and $C_{1-4}$ fluoro alkyl as defined above. R' may also be —(CH$_2$)$_n$—, where n is 3 or 4. Examples of an acylamido group include, but are not limited to, —N(H)C(═O)CF$_3$, —N(H)C(═O)Me, and:

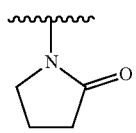 [SMILES: *N1CCCC1=O]

Acylamidomethyl: —CH$_2$-acylamido, where acylamido is as defined above, Examples of acylamidomethyl groups include, but are not limited to —CH$_2$—N(H)C(═O)Me and —CH$_2$—N(H)C(═O)CF$_3$.

$C_{1-4}$ alkyl ester: —C(═O)OR, wherein R is a $C_{1-4}$ alkyl group. Examples of $C_{1-4}$ alkyl ester groups include, but are not limited to, —C(═O)OCH$_3$, —C(═O)OCH$_2$CH$_3$, and —C(═O)OC(CH$_3$)$_3$.

$C_{1-4}$ alkyl ester methyl: —CH$_2$—($C_{1-4}$ alkyl ester), where $C_{1-4}$ alkyl ester is as defined above. Examples of $C_{1-4}$ alkyl ester methyl groups include, but are not limited to, —CH$_2$—C(═O)OCH$_3$, —CH$_2$—C(═O)OCH$_2$CH$_3$, and —CH$_2$—C(═O)OC(CH$_3$)$_3$.

$C_{1-4}$ alkyl carbamoyl: —NHC(═O)OR wherein R is a $C_{1-4}$ alkyl group as defined above. Examples of $C_{1-4}$ alkyl carbamoyl include, but are not limited to, —N(H)C(═O)OCH$_3$, —N(H)C(═O)OCH$_2$CH$_3$, and —N(H)C(═O)OC(CH$_3$)$_3$.

$C_{1-4}$ alkyl carbamoyl methyl: —CH$_2$—($C_{1-4}$ alkyl carbamoyl), where $C_{1-4}$ alkyl carbamoyl is as defined above. Examples of $C_{1-4}$ alkyl carbamoyl methyl include, but are not limited to, —CH$_2$—N(H)C(═O)OCH$_3$, —CH$_2$—N(H)C(═O)OCH$_2$CH$_3$, and —CH$_2$—N(H)C(═O)OC(CH$_3$)$_3$.

$C_{1-4}$ alkylacyl: —C(═O)R, wherein R is a $C_{1-4}$ alkyl group as defined above. Examples of $C_{1-4}$ alkylacyl groups include, but are not limited to, —C(═O)CH$_3$ (acetyl), —C(═O)CH$_2$CH$_3$ (propionyl) and —C(═O)C(CH$_3$)$_3$ (t-butyryl).

$C_{1-4}$ alkylacyl methyl: —CH$_2$—($C_{1-4}$ alkylacyl), where $C_{1-4}$ alkylacyl is as defined above. Examples of $C_{1-4}$ alkylacylmethyl groups include, but are not limited to, —CH$_2$—C(═O)CH$_3$, —CH$_2$—C(═O)CH$_2$CH$_3$, and —CH$_2$—C(═O)C(CH$_3$)$_3$.

Phenylcarbonyl: —O(═O)-phenyl, where phenyl is as defined above.

Carboxy (carboxylic acid): —C(═O)OH

Carboxymethyl: —CH$_2$—C(═O)OH.

Ether: —OP, wherein P is chosen from one of the following substituents: $C_{1-4}$ alkyl, benzyl, phenyl, $C_{1-4}$ fluoroalkyl, $C_{5-6}$ heteroaryl, —CH$_2$—$C_{5-6}$ heteroaryl, $C_{4-6}$ heterocyclyl, and —CH$_2$—$C_{4-6}$ heterocyclyl as defined above. Examples of an ether include, but are not limited to, —OPh, —OBn, —OCF$_3$, —OCH$_2$CF$_3$, —OCH(CH$_3$)$_2$, —OCH$_2$-cyclopropyl,

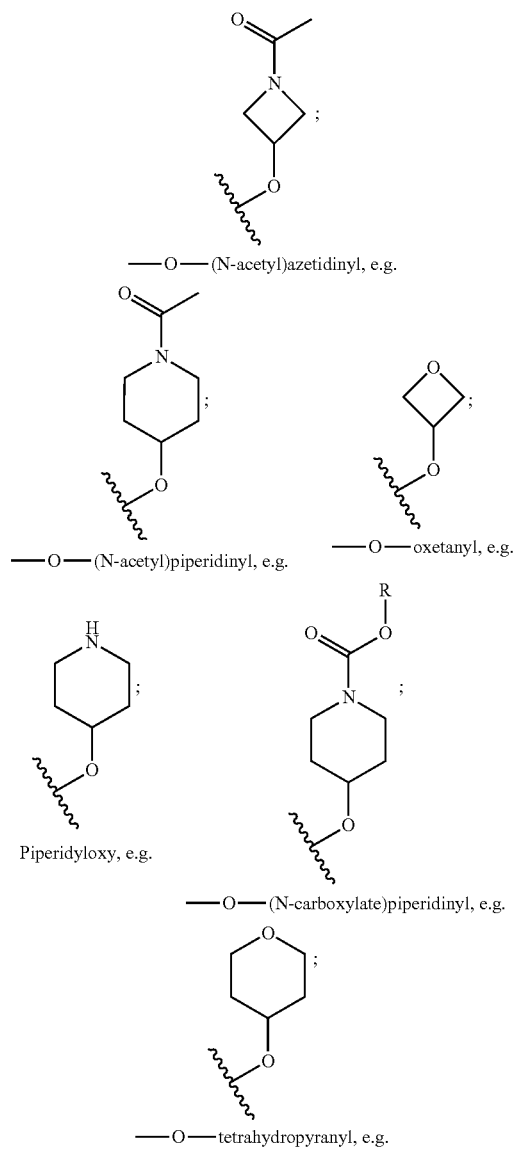

where R is methyl, isopropyl, isobutyl;

The term "$C_{1-4}$ alkyloxy" refers to the group —OP, where P is $C_{1-4}$ alkyl.

Amino: —NPP', wherein P and P' are independently chosen from H, $C_{1-4}$ alkyl, $C_{4-6}$ heterocyclyl, phenyl and $C_{5-6}$ heteroaryl as defined above. Examples of an amine include, but are not limited to, —NH$_2$, —N(H)pyridazinyl,

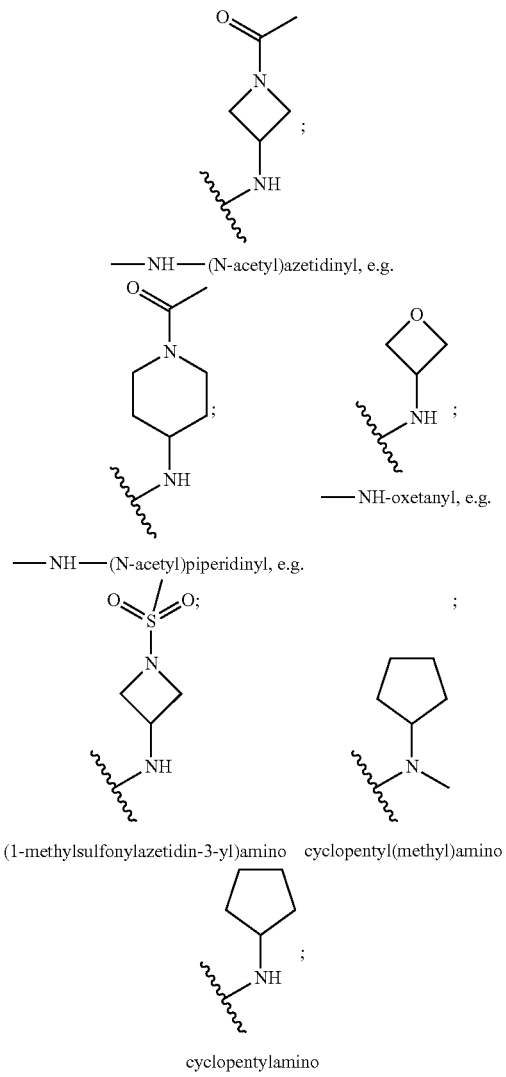

Aminomethyl: —CH$_2$-Amino, where amino is as defined above. Examples of aminomethyl include, but are not limited to, —CH$_2$—NH$_2$ and —CH$_2$—N(H)pyridazinyl.

Sulfonamido: —SO$_2$NRR' wherein R and R' are independently selected from H, $C_{1-4}$ alkyl, phenyl and $C_{5-6}$ heteroaryl as defined above. Examples of sulfonamido groups include, but are not limited to, —SO$_2$N(Me)$_2$ and —SO$_2$NPhMe.

Sulfonamino: —NHSO$_2$R wherein R is selected from $C_{1-4}$ alkyl, phenyl and $C_{5-6}$ heteroaryl as defined above. Examples of sulfonamino groups include, but are not limited, to —NHSO$_2$Me and —NHSO$_2$Ph Sulfone: —SO$_2$R, wherein R is selected from $C_{1-4}$ alkyl and $C_{1-4}$ fluoroalkyl as defined above. Example of sulfone groups includes but is not limited to SO$_2$CF$_3$.

Sulfoxide: —SOR, wherein R is selected from $C_{1-4}$ alkyl and $C_{1-4}$ fluoroalkyl as defined above. Example of sulfoxide groups includes but is not limited to SOCF$_3$.

Nitrile: —CN.
Nitrilemethyl: —CH$_2$—CN

Fused N-heterocyclic ring: where A is phenyl, it may have a $C_{5-6}$ $N_1$-containing heterocyclic ring fused to it as a substituent group. The $C_{5-6}$ $N_1$-containing heterocyclic ring may in particular be selected from:

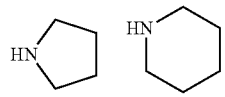

Which may be fused in any orientation, and wherein the N ring atom may be optionally substituted, for example by a $C_{1-4}$ alkylacyl group.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Compounds of the present invention have at least two stereocentres, indicated by * in the formula below:

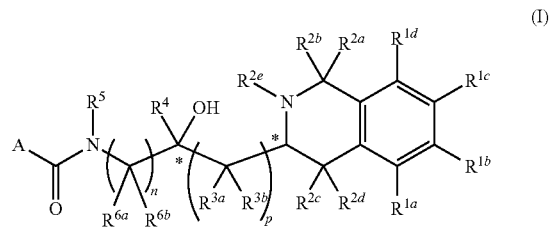

(I)

It may be preferred the compounds have the following stereochemistry:

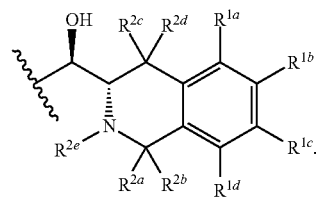

Alternatively, the compounds may have one of the following stereochemistries:

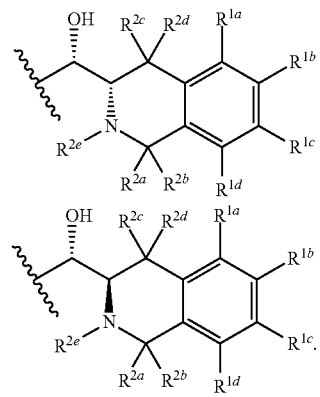

Furthermore, the compounds may have the following stereochemistry:

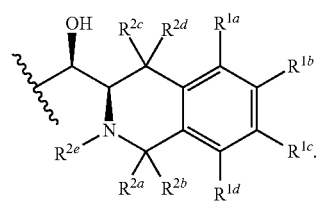

Assignment of the absolute configuration can be determined with X-ray crystallisation studies as described below.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

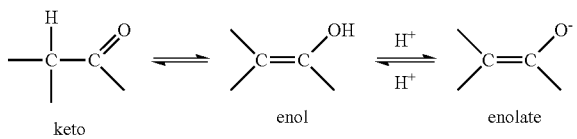

keto       enol       enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Therapeutic Indications

Compounds disclosed herein may provide a therapeutic benefit in a number of disorders, in particular, in the treatment or prevention of cancers and hemoglobinopathies.

Cancer

Modulators of PRMT5 mediated post-translational arginine methylation of p53 may regulate a pro-apoptotic p53 response, and may therefore be useful as therapeutic agents, for example in the treatment of cancer. Such agents may also be useful as therapeutic agents for the treatment of cancers which exhibit overexpression of PRMT5.

A "cancer" may be any form of cancer. In particular, a cancer can comprise any one or more of the following: leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, colon and rectal cancer, colon cancer, squamous cell carcinoma and gastric cancer.

Alternatively, the cancer may comprise adrenocortical cancer, anal cancer, bladder cancer, blood cancer, bone cancer, brain tumor, cancer of the female genital system, cancer of the male genital system, central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and/or Wilms' tumor. Cancers may be of a particular type. Examples of types of cancer include lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, sarcoma (e.g. angiosarcoma, chrondrosarcoma, osteosarcoma).

The cancer may be a PRMT5 overexpressing cancer. The cancer may over express PRMT5 protein relative to non-cancerous tissue. In some cases, the cancer overproduces PRMT5 mRNA relative to non-cancerous tissue.

Alternatively or additionally, the cancer may be a p53 overexpressing cancer. The cell may overexpress p53 protein relative to non-cancerous tissue. It may overproduce p53 mRNA as compared to non-cancerous tissue. In some cases, the level of p53 protein and/or mRNA in the cell is at a level approximately equivalent to that of a non-cancerous cell.

The agents described herein may be useful in combination with other anti-cancer therapies. They may act synergistically with chemo- or radiotherapy, and/or with p53 targeted drugs.

An inhibitor of PRMT5 would in all likelihood augment the effects of drugs (such as the nutlins) that restore p53. Inhibition of PRMT5, resulting in decreased arginine-methylated p53, may sensitize tumour cells to chemo- and radiotherapy by switching, or at least biasing, the cellular outcome to apoptosis.

Combination Therapies p53 is activated by DNA damage. PRMT5 is part of the complex of proteins that activate and modulate p53 activity in response to DNA damage. It is likely that inhibition of PRMT5, resulting in decreased arginine-methylated p53, would sensitize tumour cells to chemo- and radiotherapy by switching or at least biasing the cellular outcome to apoptosis. PRMT5 inhibition is likely to synergize well with low dose chemo- or radiotherapy, by stabilizing p53, and biasing the cellular outcome to apoptosis.

Biasing the p53 response towards apoptosis would in all likelihood be of benefit, and an agent that so biases the response would be expected to augment the effect of a p53 resurrecting drug. Thus, in some cases, a PRMT5 modulator disclosed herein may be administered in conjunction with a radiotherapeutic or chemotherapeutic regime. It may be administered in conjunction with a drug that resurrects cellular p53 activity, for example, a p53 agonist. The PRMT5 modulator may be administered simultaneously or sequentially with radio and/or chemotherapy. Suitable chemotherapeutic agents and radiotherapy protocols will be readily appreciable to the skilled person. In particular, the compound described herein may be combined with low dose chemo or radio therapy. Appropriate dosages for "low dose" chemo or radio therapy will be readily appreciable to the skilled practitioner.

Hemoglobinopathies

The compounds disclosed herein may be useful in the treatment or prevention of conditions that may benefit from the increased expression of γ-globin genes, for example, due to the release of repressive methylation of these genes. The compounds disclosed herein may be useful in the treatment or prevention of hemoglobinopathies. A hemoglobinopathy is a condition associated with the presence of abnormal hemoglobin in the blood of a subject.

Such conditions include ß-thalassemia and Sickle Cell Disease, α-thalassemia and δ-thalassemia.

Hemoglobinopathies treatable by the compounds disclosed herein may be ameliorated by the re-activation of the subjects γ-globin genes (γ genes). In such cases, the subject is not a fetal mammal.

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

As described above, the anti cancer treatment defined herein may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C5, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies Administration The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting, for example one skilled in the art may use a diverse range of synthetic methods to synthesis the desired compounds such as but not limited to methods described in literature (for example but not limited to March's Advanced Organic Chemistry: $R^{2a}$ctions, Mechanisms, and Structure, 7th Edition or Larock's Comprehensive Organic Transformations: Comprehensive Organic Transformations: A Guide to Functional Group Preparations).

Compounds of formula I, as described above, can be prepared by synthetic strategies outlined below, wherein the definitions above apply.

General Synthesis 1a

Scheme 1A

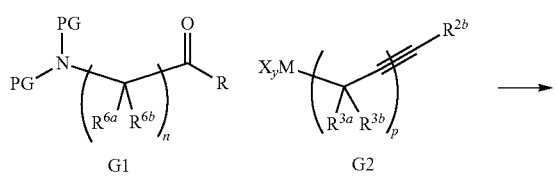

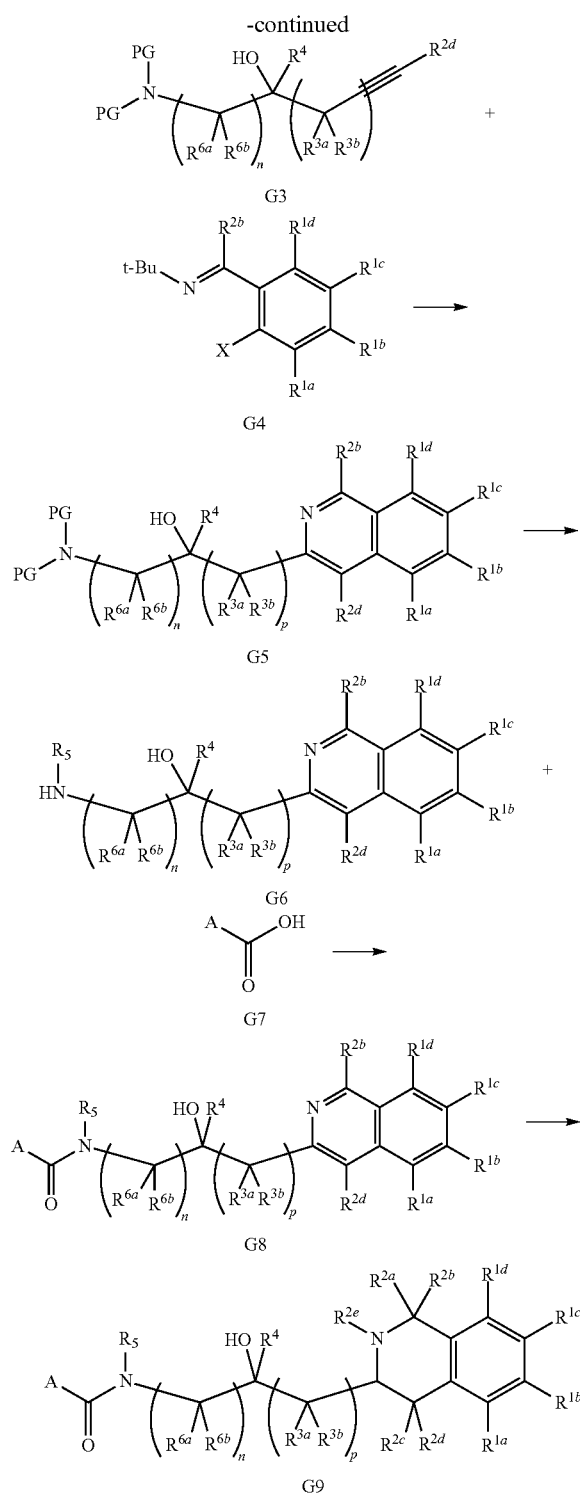

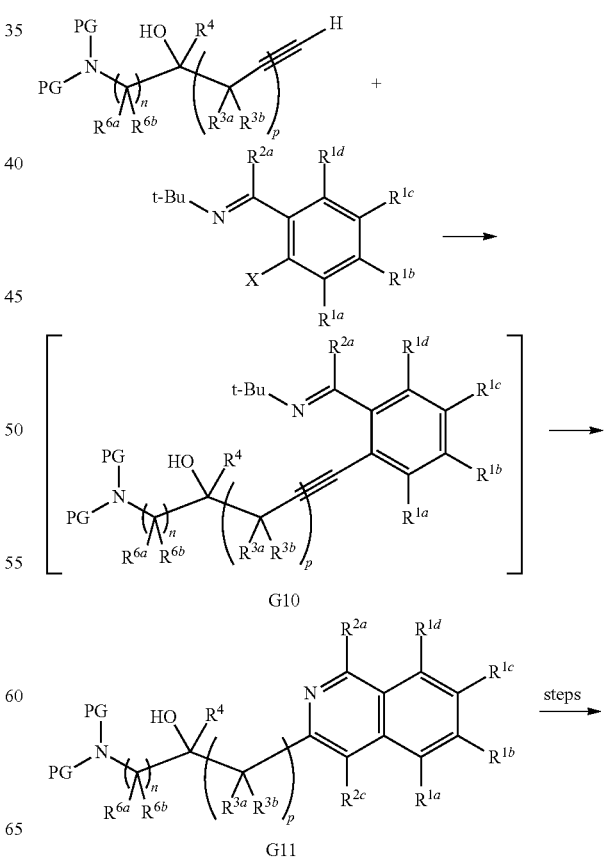

imide; and methods for the removal of said protecting groups will be known to those skilled in the art (for example *Greene's Protective Groups in Organic Synthesis*, 4th Edition). Synthesis of compounds with structure G5 is performed by reacting alkyne G3 with compounds of structure G4 in the presence of a transition metal catalyst or combination of transition metal catalysts such as but not limited to bis(triphenylphosphine)nickel(II) chloride/Zn.

After removal of the protecting group, for $R^5$=Me, methods to synthesis G6 will require an additional methylation reaction apparent to those skilled in the art, but include for example, a reductive amination with formaldehyde and a reducing agent or combination of reducing agents such as but not limited to formic acid, formic acid derivatives, $NaBH_4$, $NaCNBH_4$, $NaBH(OAc)_3$ or $NaBH_3CN$—Ti$(Oi\text{-}Pr)_4$. Methods to synthesise amides G8 will be apparent to those skilled in the art, but include for example the use of reagents such as HATU, HBTU, T3P and EDCI/HOBt, and the use of activated forms of the carboxylic acid G7 such as the corresponding acyl halide, carbamate or N-hydroxysuccinimide ester. Transformation of isoquinolines of structure G8 to give tetrahydroisoquinolines of structure G9 will be apparent to those skilled in the art and such methods include but are not limited to reduction in the presence of a transition metal catalyst. For $R^{2e}$=Me, methods to synthesis G9 will require an additional methylation reaction apparent to those skilled in the art, but include for example, a reductive amination with formaldehyde and a reducing agent or combination of reducing agents such as but not limited to formic acid, formic acid derivatives, $NaBH_4$, $NaCNBH_4$, $NaBH(OAc)_3$ or $NaBH_3CN$—Ti$(Oi\text{-}Pr)_4$.

Scheme 1A illustrates the synthesis of compounds with the structure G9 where $R^{2a}$ and $R^{2c}$=H. A coupling of a carbonyl compound of structure G1 with an organometallic compound of structure G2 to give a compound with structure G3 will be apparent to those skilled in the art. The group represented by (M) includes but is not limited to Mg, In, Zn and the group represented by (X) may be a halide where (Y) may be the number 1-3. Suitable protected amino groups represented by (PG) include but are not limited to phthal-

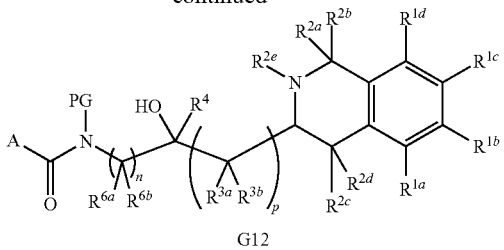

G12

Alternatively, for the synthesis of compounds with structure G12 where $R^{2b}$, $R^{2c}$, $R^{2d}$=H, a coupling of an alkyne and an aryl halide will be apparent to those skilled in the art and such methods include a coupling in the presence of a transition metal catalyst or catalyst combination such as but not limited to $PdCl_2(PPh_3)_2/CuI$ and $Pd(OAc)_2/PPh_3$. This may be followed by cyclisation either in situ or as a separate step to give isoquinoline of structure G11. The synthetic steps to give compounds with general formula G12 will be similar to those used in Scheme 1A.

General Synthesis 1b $H_2SO_4$ or $BF_3.OEt_2$ to furnish tetrahydroisoquinoline X3. Protection of the amine using a suitable protecting group will be apparent to those skilled in the art (for example *Greene's Protective Groups in Organic Synthesis,* 4th Edition) and gives intermediate X4. Reduction of the acid group to the primary alcohol X5 will be apparent to those skilled in the art and include but are not limited to the use of reagents such as $NaBH_4/CDI$, $LiBH_4$, $LiAlH_4$, and borane complexes. Oxidation of the alcohol to the corresponding aldehyde X7 will be apparent to those skilled in the art and include but are not limited to the use of reagents such as Dess-Martin periodinane, IBX or dimethylsulfoxide combined with a suitable electrophilic reagent such as but not limited to pyridine-sulfur trioxide. Alternatively, methods to form the Weinreb amide X6 will be apparent to those skilled in the art, but include for example the use of reagents such as but not limited to N,O-dimethylhydroxylamine and HATU, HBTU, T3P and EDCI/HOBt, or the use of activated forms of the carboxylic acid such as the corresponding acyl halide, mixed anhydride or N-hydroxysuccinimide ester. Reduction of the amide to the aldehyde ($R^4$=H) will be Scheme 1b

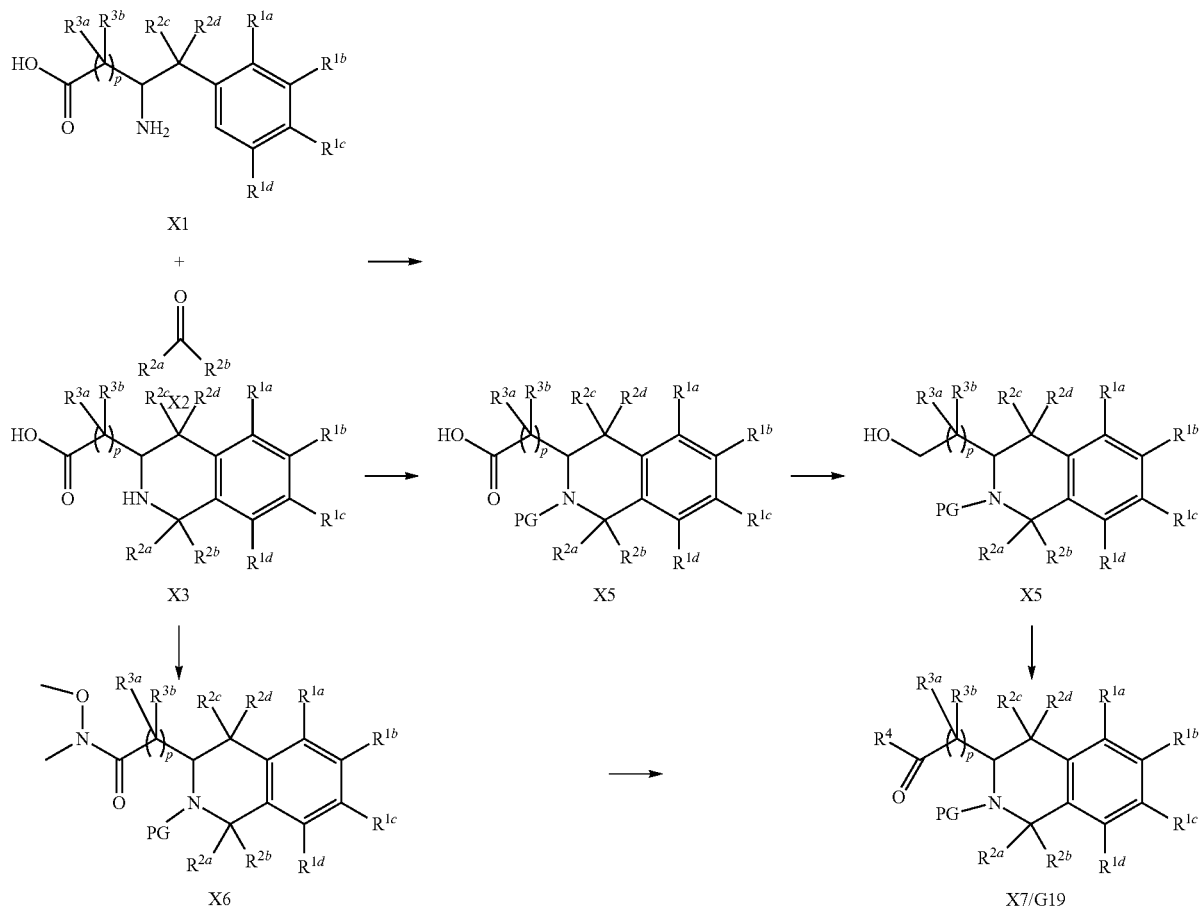

Scheme 1b illustrates the synthesis of intermediate compounds X7/G19, beginning with a Pictet-Spengler reaction between a β-arylethylamine X1 and an aldehyde (or ketone where $R^{2c}$ and $R^{2d}$ is not =H) X2 in the presence or absence of a suitable acid, such as but not limited to HCl, TFA, apparent to those skilled in the art and include but are not limited to reagents such as $LiAlH_4$. For $R^4$=Me, treatment of the intermediate amide X6 with a suitable organometallic reagent such as but not limited to MeLi or MeMgBr furnishes X7/G19.

General Synthesis 2

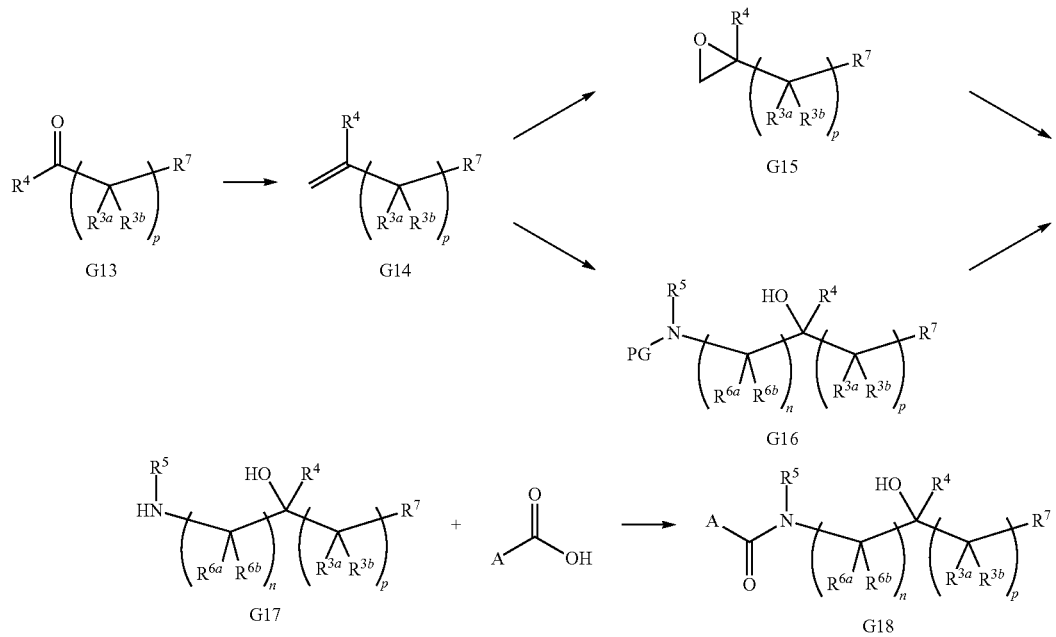

Where R[7] represents the fused ring group.

Scheme 2A illustrates the synthesis of compounds G18 from aldehyde G13 (or ketone where $R^4$=Me). Conversion of a carbonyl to an alkene will be apparent to those skilled in the art but methods include but are not limited to a Wittig reaction with $[Ph_3PMe]^+Br^-$ in the presence of a base such as KHMDS. The alkene G14 can be epoxidised with reagents such as m-CPBA and then reacted with an amine to give intermediate G16. Alternatively, an aminohydroxylation can be performed by methods such as but not limited to reaction with (PG)NHOTs in the presence of potassium osmate dihydrate. Removal of the protecting group will be apparent to those skilled in the art (for example *Greene's Protective Groups in Organic Synthesis,* 4th Edition) and gives intermediate G17. Amide bond formation to give compounds G18 can be performed by methods previously described (General synthesis 1).

General Synthesis 3

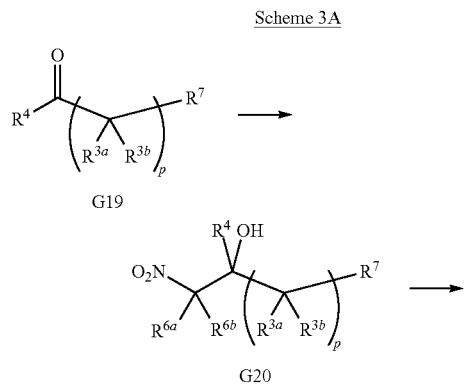

Where R[7] represents the fused ring group.

Scheme 3A illustrates the synthesis of compounds G22 beginning with a Henry reaction between an aldehyde G19 (or ketone where $R^4$=Me) and nitromethane in the presence or absence of a suitable base, such as but not limited to DBU, a KF, TBAF or sodium hydroxide, in the presence or absence of a chiral or achiral transition metal compound for example but not limited to complexes of copper, cobalt or zinc to furnish a nitro-alcohol G20. Reduction of the nitro group to the primary amine G21 will be apparent to those skilled in the art and include but are not limited to using reducing conditions such as a transition metal (Fe, In, Zn) in the presence of HCl, hydrogenation in the presence of a transition metal or transition metal catalyst. Amide bond formation to give compounds G22 can be performed by methods previously described (General synthesis 1). The method can also be carried out with nitroethane and other nitroalkanes, as appropriate.

General Synthesis 4

Scheme 4A illustrates the addition of an amine ($HNR^8R^9$), as a substituent which is a part of A. This can be achieved by coupling a relevant carboxylic acid to a primary amine or a secondary amine, NHR$^8$R$^9$. Methods to form such amides will be apparent to those skilled in the art, but include for example the use of reagents such as HATU, HBTU, T3P and EDCI/HOBt, and the use of activated forms of the carboxylic acid such as the corresponding acyl halide, mixed anhydride or N-hydroxysuccinimide ester. The group denoted by (X) may be but not limited to halogen, tosylate or other suitable group. Conversion of (X) in G22 into an ester in G23 will be apparent to those skilled in the art, but include for example a carbonylation reaction which can be achieved by the use of carbon monoxide in the presence of an transition metal catalyst such as but not limited to PdCl$_2$dppf.DCM; and an alcoholic solvent such as but not limited to methanol, ethanol, isopropanol or tert-butyl alcohol. Formation of the carboxylic acid can be achieved by for example hydrolysis with a base such as an alkali metal hydroxide or an acid for example aqueous hydrochloric acid to form G24. The amide formation to form G25 can be achieved by the methods outline in Scheme 1A.

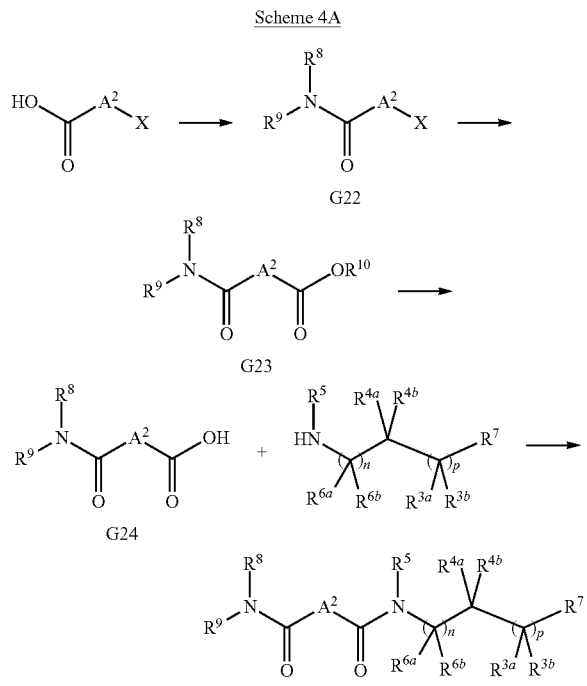

Alternatively, for the synthesis of ester G24 the order of steps can be reversed as described in Scheme 4B.

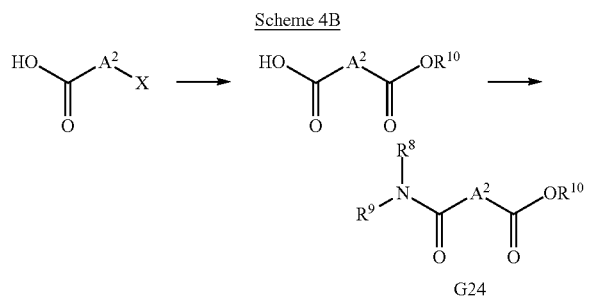

Alternatively for the synthesis of amide G25 the steps may be reordered such that the formation of the R$^8$R$^9$N amide on the A substituent occurs after the coupling of A to the primary amine G21. This may be achieved by coupling a suitable amine with an intermediate where A bears a suitable functional group for coupling, for example but not limited to a carboxylic acid or alkali metal carboxylate salt, as shown in Scheme 4C.

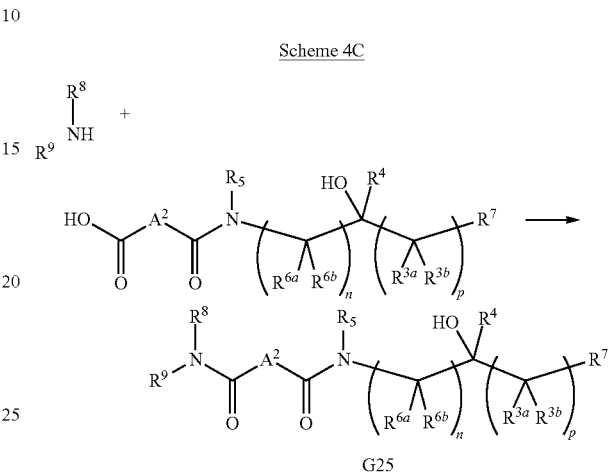

General Synthesis 5

Scheme 5A illustrates the addition of an R$^{11}$ group, as a substituent which is part of A. This can be achieved using any suitable coupling reaction known to the person skilled in the art, for example by Suzuki coupling. The groups denoted by R$^{11}$X and B$^1$ are chosen to be suitable for the coupling reaction employed. For example, in the case of a Suzuki coupling reaction (X) may be a halogen, tosylate or other suitable group and B$^1$ represents a suitable boron compound including, but not limited to, a boronic acid or boronic ester.

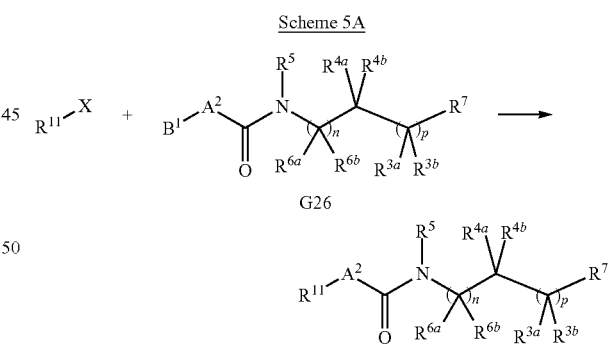

Examples of B$^1$ that can be used in the Suzuki coupling include, but are not limited to, those shown below.

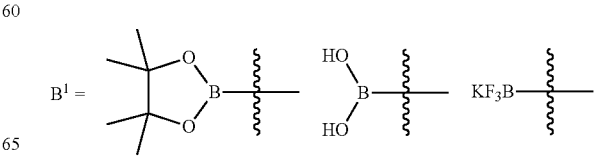

The types of R$^{11}$X compounds that can be used in the Suzuki coupling include, but are not limited to, those shown in Table 1.

TABLE 1

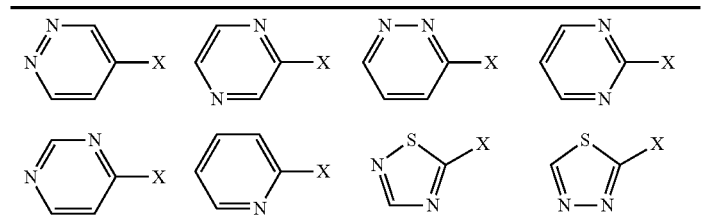

In addition to scheme 5A, the position of the (X) and (B$^1$) can be reversed as shown below in scheme 2B, to give the same final compound G27. Similarly to Scheme 2A, the groups denoted by R$^{11}$B$^1$ and (X) are chosen to be suitable for the coupling reaction employed. For example, in the case of a Suzuki coupling reaction (X) may be a halogen, tosylate or other suitable group and R$^{11}$B$^1$ represents a suitable boron compound including, but not limited to, a boronic acid or boronic ester.

groups denoted by (X) and B$^1$ are chosen to be suitable for the coupling reaction employed. For example, in the case of a Suzuki coupling reaction (X) may be a halogen, tosylate or other suitable group and B$^1$ represents a suitable boron compound including, but not limited to, a boronic acid or boronic ester.

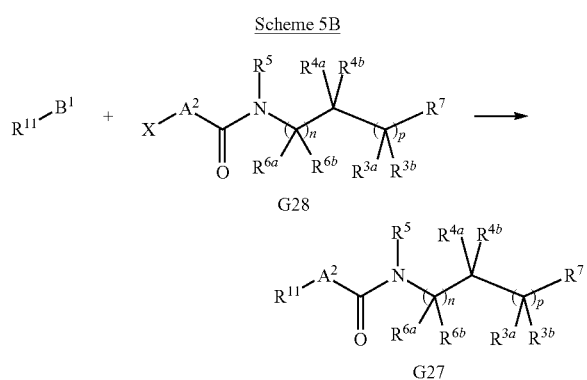

Scheme 5B

G28

G27

The types of R$^{11}$B$^1$ compounds that can be used in the Suzuki coupling include, but are not limited to, those shown in Table 2.

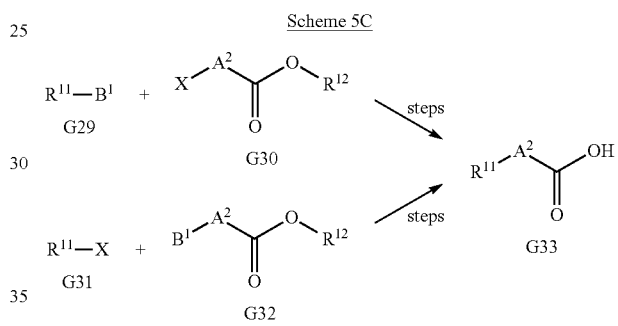

Scheme 5C

G29 + G30 → steps → G33

G31 + G32 → steps

In G30 and G32 R$^{12}$ can be a H or a carbon group for example but not limited to Me, Et, Pr, iPr, Bu, t-Bu. In these instances where R$^{12}$ is carbon group it may be necessary to form the carboxylic acid before use in the amide coupling (Scheme 1A), generally this can be achieved by for example

TABLE 2

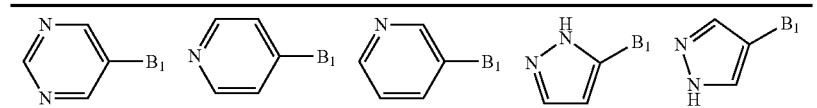

A variety of coupling reactions may be used to introduce the R$^{11}$ group other than Suzuki coupling, such as for example transition metal catalysed coupling reactions of for example tin (Stille type reaction) and zinc (Negishi type reaction) compounds. Substitution of the halogen by suitable nucleophiles in the presence or absence of other reagents such as for example transition metal compounds is also suitable.

Coupling reactions can also be used to prepare the carboxylic acids used in Scheme 1A for the amide formations, scheme 5C. In starting material G30 and G32, A as described herein, consists of -A$^2$X and -A$^2$B$^1$ respectively. In the product G33, A as described herein, consists of -A$^2$R$^{11}$. The hydrolysis with a base such as an alkali metal hydroxide or an acid for example aqueous hydrochloric acid to form G33. The same method for converting an ester to a carboxylic acid is used in other general schemes.

General Synthesis 6

Scheme 6A illustrates the addition of an R$^{13}$ group, as a substituent which is part of A. This can be achieved using any suitable coupling reaction known to the person skilled in the art, for example, by an SnAr displacement or Buchwald coupling. The group denoted by (X) may be but not limited to halogen and is chosen to be suitable for the coupling reaction employed.

Scheme 6A

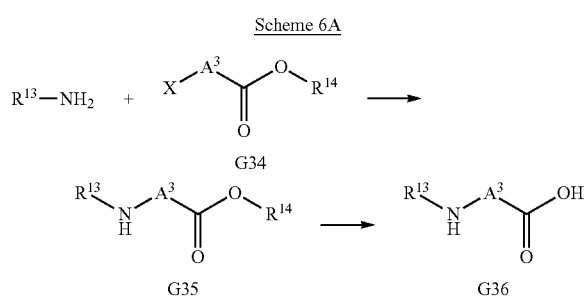

In G34 and G35 $R^{14}$ can be a H or a carbon group for example but not limited to Me, Et, Pr, iPr, Bu, t-Bu. In these instances it may be necessary to form the carboxylic acid before use in an amide coupling (Scheme 1A), generally this can be achieved by, for example, hydrolysis with a base such as an alkali metal hydroxide or an acid, for example, aqueous hydrochloric acid to form G36. The same method for converting an ester to a carboxylic acid is used in other general schemes.

This method may also be extended to the addition of secondary amines.

Alternatively, to synthesise ether linked compounds, a similar strategy can be employed as shown in Scheme 6B. This can be achieved using any suitable coupling reaction known to a person skilled in the art, for example, by an $S_NAr$ displacement or an Ullman-type coupling to give compounds with structure G37. Upon hydrolysis using methods previously described, compounds with structure G38 may be obtained and used in an amide bond formation as shown in scheme 1A.

Scheme 6B

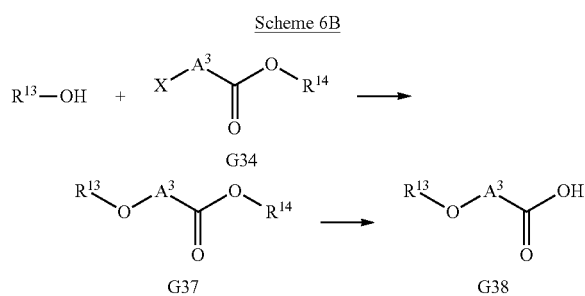

Both the above couplings may also be reversed, such that the group added is $R^{13}$—X.

Further Embodiments n

In some embodiments, n is 1. In some embodiments, n is 2.

p

In some embodiments, p is 0. In some embodiments, p is 1.

$R^{1a}$, $R^{1b}$, $R^{1c}$ and $R^{1d}$

In some embodiments, $R^{1a}$, $R^{1b}$, $R^{1c}$ and $R^{1d}$ are all H. In some embodiments, one of $R^{1a}$, $R^{1b}$, $R^{1c}$ and $R^{1d}$ is halo, $C_{1-4}$ alkoxy, $C_{1-4}$ alkyl, $C_{1-4}$ fluoroalkyl, $C_{3-4}$ cycloalkyl, NH—$C_{1-4}$ alkyl or cyano. In some of there embodiments, $R^{1b}$ or $R^{1c}$ is halo, $C_{1-4}$ alkoxy, $C_{1-4}$ alkyl, $C_{1-4}$ fluoroalkyl, $C_{3-4}$ cycloalkyl, NH—$C_{1-4}$ alkyl or cyano, and in further of these embodiments, $R^{1c}$ is halo, $C_{1-4}$ alkoxy, $C_{1-4}$ alkyl, $C_{1-4}$ fluoroalkyl, $C_{3-4}$ cycloalkyl, NH—$C_{1-4}$ alkyl or cyano. Where one of $R^{1a}$, $R^{1b}$, $R^{1c}$ and $R^{1d}$ is halo, $C_{1-4}$ alkoxy, $C_{1-4}$ alkyl, $C_{1-4}$ fluoroalkyl, $C_{3-4}$ cycloalkyl, NH—$C_{1-4}$ alkyl or cyano, it may be that the group is chloro, methoxy, methyl, ethyl, NHMe or cyano. In some embodiments, the group is methoxy.

In further embodiments, $R^{1c}$ is selected from methoxy, ethoxy, ethyl, $CHF_2$, $CF_3$ and cyano. In some of these embodiments, $R^{1c}$ is selected from methoxy, ethyl, $CHF_2$, $CF_3$ and cyano.

$R^{2a}$, $R^{2b}$, $R^{2c}$ and $R^{2d}$ $R^{2a}$, $R^{2b}$, $R^{2c}$ and $R^{2d}$ are independently selected from H, F, $CH_2OH$ and Me. In some of these embodiments, $R^{2a}$, $R^{2b}$, $R^{2c}$ and $R^{2d}$ are independently selected from H, Me and $CH_2OH$. In further of these embodiments, $R^{2a}$, $R^{2b}$, $R^{2c}$ and $R^{2d}$ are independently selected from H and Me.

In some embodiments $R^{2a}$, $R^{2b}$, $R^{2c}$ and $R^{2d}$ are all H.

In some embodiments $R^{2a}$, $R^{2b}$, $R^{2c}$ and $R^{2d}$ are comprised of three H and one Me or $CH_2OH$ group. It may be preferred in these embodiments that $R^{2a}$ is Me and $R^{2b}$, $R^{2c}$ and $R^{2d}$ are H. It may be preferred in these embodiments that $R^{2c}$ is Me or $CH_2OH$ and $R^{2a}$, $R^{2b}$ and $R^{2d}$ are H.

In some embodiments $R^{2a}$, $R^{2b}$, $R^{2c}$ and $R^{2d}$ are comprised of two H and two Me groups. It may be preferred in these embodiments that $R^{2a}$ and $R^{2c}$ are Me and $R^{2b}$ and $R^{2d}$ are H. It may be preferred in these embodiments that $R^{2a}$ and $R^{2b}$ are Me and $R^{2c}$ and $R^{2d}$ are H. It may also be preferred in these embodiments that $R^{2c}$ and $R^{2d}$ are Me and $R^{2a}$ and $R^{2b}$ are H.

In some embodiments, $R^{2c}$ and $R^{2d}$ are independently selected from H and F.

$R^{2e}$

In some embodiments, $R^{2e}$ is H. In other embodiments, $R^{2e}$ is Me.

$R^3$ $R^{3a}$ and $R^{3b}$ are independently selected from H and Me. In some embodiments $R^{3a}$ is H and $R^{3b}$ is Me. In some embodiments $R^{3a}$ and $R^{3b}$ are both H. In some embodiments $R^{3a}$ and $R^{3b}$ are both Me.

$R^4$

In some embodiments $R^4$ is H. In some embodiments $R^4$ is Me.

$R^5$

In some embodiments $R^5$ is H. In some embodiments $R^5$ is Me.

$R^6$ $R^{6a}$ and $R^{6b}$ are independently selected from H and Me. In some embodiments $R^{6a}$ is H and $R^{6b}$ is Me. In some embodiments $R^{6a}$ and $R^{6b}$ are both H. In some embodiments $R^{6a}$ and $R^{6b}$ are both Me.

Stereoisomers

The carbon to which $R^4$ is attached is a chiral centre.

In some embodiments, the compound is a mixture of stereoisomers at this centre. In some embodiments, the compound is a single stereoisomer. In some of these embodiments, the compound is the (R)-stereoisomer. In others of these embodiments, the compound is the (S)-stereoisomer.

The compound may also include further chiral centres. The carbon in the THIQ moiety is chiral. In some embodiments, the compound is a mixture of stereoisomers at this centre. In other embodiments, the compound is a single stereoisomer at this centre. In some of these embodiments, the compound is the (R)-stereoisomer at this centre. In others of these embodiments, the compound is the (S)-stereoisomer at this centre.

Thus the compound may be a single diastereomer or a mixture of diastereomers.

It may be preferred the compounds have the following stereochemistry:

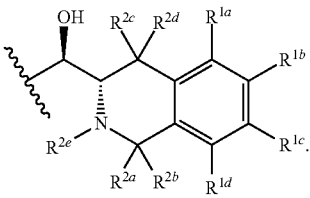

Alternatively, the compounds may have one of the following stereochemistries:

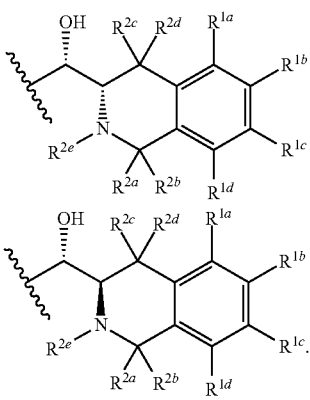

$R^1$-$R^5$, n & p

In some embodiments, $R^{1a}$, $R^{1b}$, $R^{1d}$, $R^{2a}$, $R^{2b}$, $R^{2c}$, $R^{2d}$, $R^4$, $R^5$, $R^{6a}$ and $R^{6b}$ are all H, n is 1 and p is 0, and thus the compound of formula I is of formula Ia:

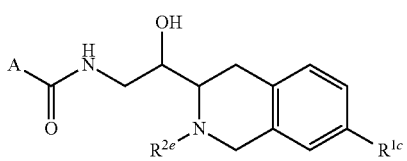

wherein $R^{1c}$ is H or $C_{1-4}$ alkoxy, $C_{2-4}$ alkyl, NH—$C_{1-4}$ alkyl or cyano (e.g. methoxy) and $R^{2e}$ is H or methyl, and one of $R^{1c}$ and $R^{2e}$ is not H.

In some embodiments, $R^{1a}$, $R^{1b}$, $R^{1d}$, $R^{2a}$, $R^{2b}$, $R^{2c}$, $R^{2d}$, $R^{3a}$, $R^{3b}$, $R^4$, $R^5$, $R^{6a}$ and $R^{6b}$ are all H, n is 1 and p is 1, and thus the compound of formula I is of formula Ib:

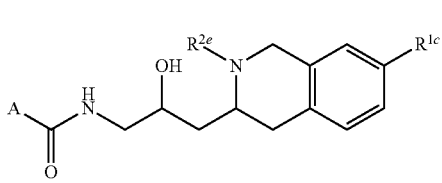

wherein $R^{1c}$ is H or $C_{1-4}$ alkoxy, $C_{2-4}$ alkyl, NH—$C_{1-4}$ alkyl or cyano (e.g. methoxy) and $R^{2e}$ is H or methyl, and one of $R^{1c}$ and $R^{2e}$ is not H.

In some embodiments, $R^{1a}$, $R^{1b}$, $R^{1d}$, $R^{2a}$, $R^{2b}$, $R^{2c}$, $R^{2d}$, $R^4$, $R^5$, $R^{6a}$ are all H, n is 1 and p is 0, and $R^{6b}$ is Me and thus the compound of formula I is of formula Ic:

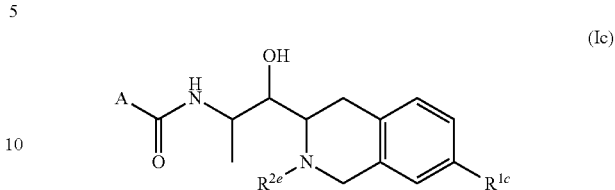

wherein $R^{1c}$ is H or $C_{1-4}$ alkoxy, $C_{2-4}$ alkyl, NH—$C_{1-4}$ alkyl or cyano (e.g. methoxy) and $R^{2e}$ is H or methyl, and one of $R^{1c}$ and $R^{2e}$ is not H.

A

Optional Substituents

When the optional substituent on A is $C_{1-4}$ alkyl, it may be preferably selected from methyl, ethyl, i-Pr, t-Bu.

When the optional substituent on A is $C_{1-4}$ fluoroalkyl, it may preferably be selected from —$CF_3$ and —$CF_2H$.

When the optional substituent on A is $C_{5-6}$ heteroaryl, it may be substituted by one or more $C_{1-4}$ alkyl groups. These groups may preferably be on one or more of the nitrogen ring atoms (if present). These groups may also preferably be methyl.

Further, when the optional substituent on A is $C_{5-6}$ heteroaryl, it may be substituted by a $C_{3-4}$ alkylene group which is bound to the ring in two places to form a fused ring structure.

When the optional substituent on A is $C_{5-6}$ heteroaryl, it may preferably be selected from pyridizinyl, pyrimidinyl, pyridinyl, pyrazolyl, pyrazinyl, oxadiazolyl, isoxazolyl, triazolyl, imidazolyl, benzimidazolyl and thiadiazolyl.

When the optional substituent on A is $C_{5-6}$ heteroaryl methyl, it may preferably be selected from —$CH_2$-imidazolyl and —$CH_2$-triazolyl.

When the optional substituent on A is $C_{5-6}$ heterocyclyl, it may preferably be morpholino.

When the optional substituent on A is $C_{5-6}$ heterocyclyl methyl, it may preferably be selected from —$CH_2$-morpholino and —$CH_2$-piperazinyl.

When the optional substituent on A is phenyl, it may be substituted by one or more $C_{1-4}$ alkyl groups. These groups may preferably be methyl.

When the optional substituent on A is phenyl, it may be substituted by one or more $C_{1-4}$ fluoroalkyl groups. These groups may preferably be trifluoromethyl.

When the optional substituent on A is phenyl, it may be substituted by one or more $C_{1-4}$ alkoxy groups. These groups may preferably be methoxy.

When the optional substituent on A is phenyl, it may be substituted by one or more halo substituents. These groups may preferably be fluoro or chloro, more preferably fluoro.

When the optional substituent on A is phenyl, it may be substituted by one or more cyano groups. It may be preferred that there is a single cyano substituent.

When the optional substituent on A is halo, it may preferably be selected from F, Cl and Br.

When the optional substituent on A is amido, the amido substituent groups R and R' may preferably form a ring, which ring may also be bridged or substituted. If the amido group is not cyclic, it may preferably be selected from —C(═O)$NH_2$, —C(═O)NMeH, —C(═O)$NMe_2$ and —C(═O)$N^iPrH$. If the amido group is cyclic, it may preferably be selected from —C(═O)-piperidinyl, —C(═O)- hydroxypiperidinyl, —C(=O)-methoxypiperidinyl, —C(=O)-pyrrolidinyl, —C(=O)-morpholino, —C(=O)-methylmorpholino, —C(=O)-dimethylmorpholino and —C(=O)-azetidinyl. Further cyclic amido groups include:

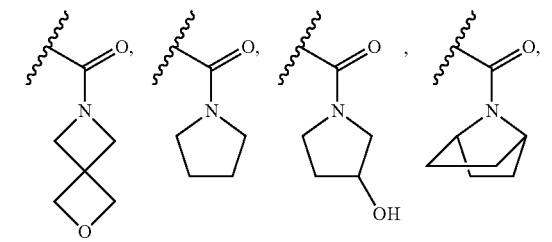

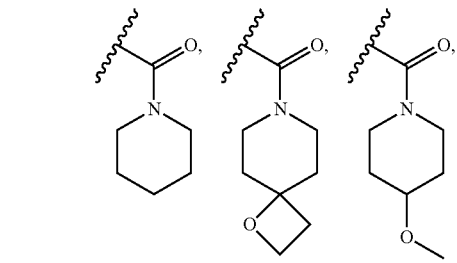

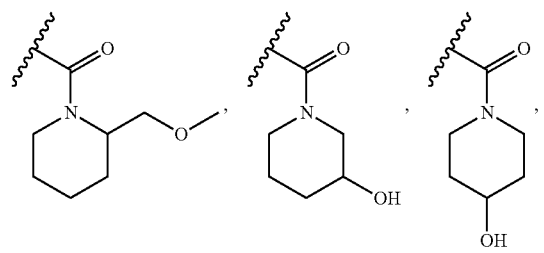

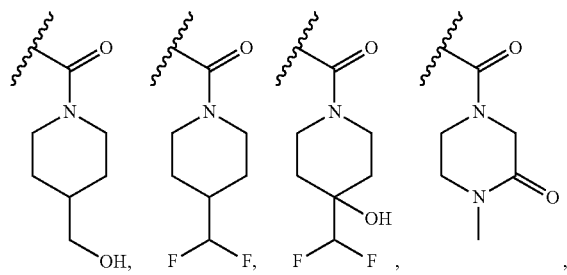

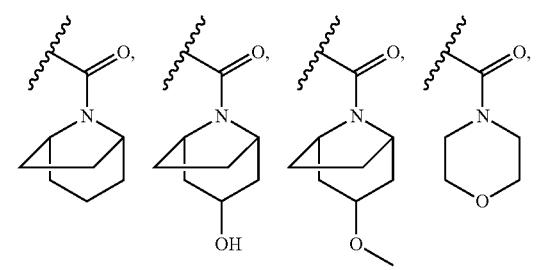

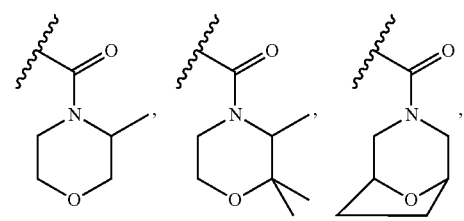

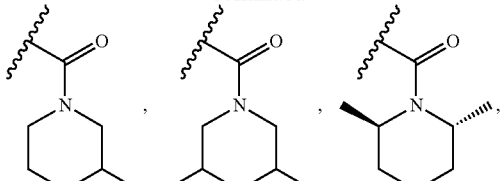

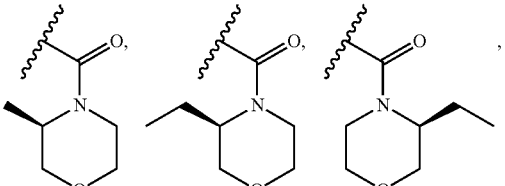

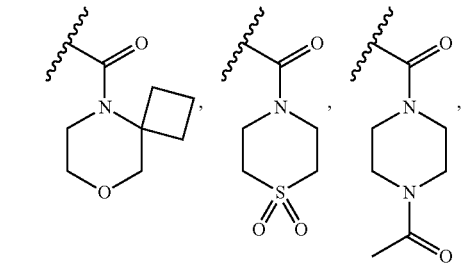

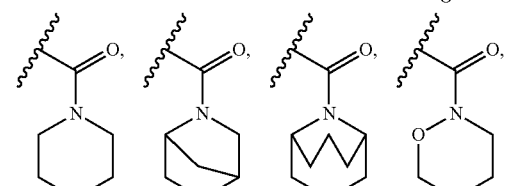

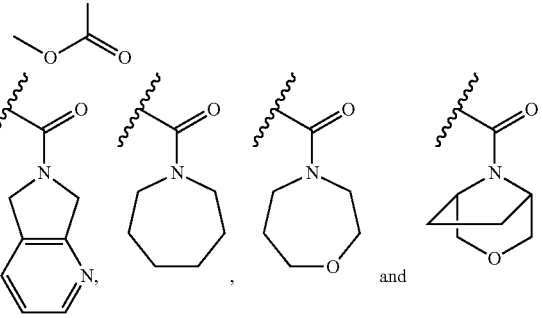

When the optional substituent on A is amidomethyl, the amido substituent groups R and R' may preferably form a ring, which ring may also be bridged or substituted. If the amido group is not cyclic, the amidomethyl group may preferably be selected from —CH₂C(=O)NH₂, —CH₂C(=O)NMeH and —CH₂C(=O)N'PrH. If the amido group is cyclic, the amidomethyl group may preferably be selected from —CH₂C(=O)-pyrrolidinyl-CH₂C(=O)-morpholino, —C(=O)-hydroxypiperidinyl, —C(=O)-methoxypiperidinyl, —C(=O)-methylmorpholino and CH₂C(=O)-azetidinyl. Further cyclic amidomethyl groups include:

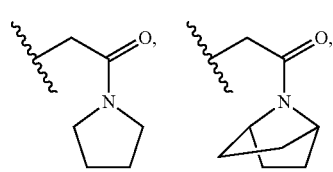

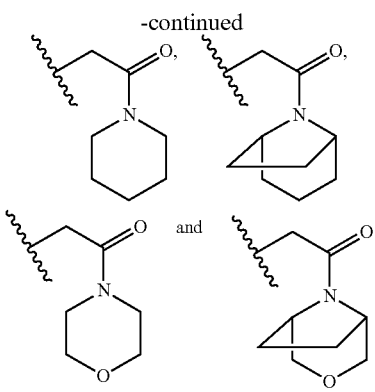

When the optional substituent on A is acylamido, it may preferably be γ-lactam.

When the optional substituent on A is acylamidomethyl, it may preferably be selected from —CH$_2$NHC(=O)Me, —CH$_2$NHC(=O)CF$_3$.

When the optional substituent on A is C$_{1-4}$ alkyl ester, it may preferably be —C(=O)—OMe.

When the optional substituent on A is C$_{1-4}$ alkyl ester methyl, it may preferably be —CH$_2$—C(=O)—OMe.

When the optional substituent on A is C$_{1-4}$ alkyl carbamoyl methyl, it may preferably be —CH$_2$NHC(=O)OMe.

When the optional substituent on A is C$_{1-4}$ alkylacyl, it may preferably be selected from —C(=O)Me and —C(=O)Et.

When the optional substituent on A is C$_{1-4}$ alkylacylmethyl, it may preferably be —CH$_2$C(=O)Me.

When the optional substituent on A is phenylcarbonyl, it may preferably be —C(=O)-Ph.

When the optional substituent on A is ether, it may preferably be selected from methoxy, ethoxy, —OBn, —OPh, —OCF$_3$, —OCF$_2$H, —O—(C$_6$H$_4$)—CN, —O-oxanyl, —OCH$_2$pyridinyl, —OCH$_2$oxadiazolyl, —OCH$_2$-isoxazole, When the optional substituent on A is amino, the amino substituent may be a C$_{5-6}$ heteroaryl group, in which case the amino group may preferably be selected from —NH-pyrazinyl, —NH-pyrimidine. In other embodiments, the amino substituent may be a C$_{4-6}$ heterocyclyl group, such as optionally N-substituted azetidinyl, optionally N-substituted piperidinyl and oxetanyl. A further amino group may be:

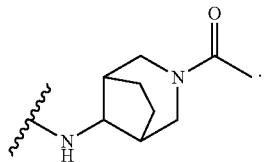 [SMILES: *NC1C2CCC1CN(C(C)=O)C2]

When the optional substituent on A is aminomethyl, it may preferably be —CH$_2$NH$_2$. Alternatively, the amino substituent may be as defined above.

When the optional substituent on A is sulfonamido it may preferably be selected from —SO$_2$NMePh, —SO$_2$NMe$_2$, and —SO$_2$NHEt.

When the optional substituent on A is sulfonamino, it may preferably be selected from —NHSO$_2$Ph and —NHSO$_2$Me.

When the optional substituent on A is sulfone, it may preferably be —SO$_2$CF$_3$.

Optionally Substituted Phenyl

In some embodiments A may be an optionally substituted phenyl.

In some of these embodiments, A is unsubstituted phenyl.

In some of these embodiments, the phenyl of A has 1, 2, 3, 4 or 5 substituents.

In some of these embodiments, the phenyl of A has 1 or 2 substituents.

It may be preferred in some of these some of these embodiments that R$^{1-6}$ and n and p are such that the compound is of formula Ia, Ib or Ic.

It may be preferred in these embodiments that the optional substituents are independently selected from the following: C$_{1-4}$ alkyl; C$_{1-4}$ fluoroalkyl; C$_{3-6}$cycloalkyl; C$_{5-6}$ heteroaryl; C$_{5-6}$ heteroaryl methyl; C$_{4-6}$ heterocyclyl; C$_{4-6}$ heterocyclyl methyl; phenyl; benzyl; halo; amido; amidomethyl; acylamido; acylamidomethyl; C$_{1-4}$ alkyl ester; C$_{1-4}$ alkyl ester methyl; C$_{1-4}$ alkyl carbamoyl; C$_{1-4}$ alkyl carbamoyl methyl; C$_{1-4}$ alkylacyl; C$_{1-4}$ alkyl acyl methyl; phneylcarbonyl; carboxy; carboxymethyl; ether; amino; aminomethyl; sulfonamido; sulfonamino; sulfone; nitrile; and nitrilemethyl.

It may be preferred in these embodiments that the optional substituents are selected from: C$_{1-4}$ alkyl, fluoro, chloro, bromo, acetyl, methoxy, ethoxy, —C(=O)Me, —C(=O)Et, —CH$_2$C(=O)Me, phenyl, —CF$_3$, —CF$_2$H, —CN, —CH$_2$CN, —OBn, —OPh, —OCF$_3$, —OCF$_2$H, —O—(C$_6$H$_4$)—CN, —COOH, —CH$_2$COOH, —C(=O)OMe, —C(=O)NH$_2$, —C(=O)NMeH, —C(=O)NMe$_2$, —C(=O)N$^i$PrH, —C(=O)-piperidinyl, —C(=O)-pyrrolidinyl, —C(=O)-morpholino (which may be bridged or substituted by one of two methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl, —CH$_2$C(=O)-morpholino, —CH$_2$-morpholino, —CH$_2$-methylpiperazinyl, —OCH$_2$pyridinyl, —OCH$_2$-methyloxadiazolyl, —CH$_2$-imidazolyl, —O-tetrahydropyranyl, —CH$_2$-tetrahydropyranyl, —NH-methylpyrazinyl, —CH$_2$-triazolyl, —NHSO$_2$Ph, —NHSO$_2$Me, —SO$_2$NMePh, —SO$_2$NMe$_2$, —SO$_2$NHEt, —SO$_2$CF$_3$, —γ-lactam, —CH$_2$NHC(=O)Me, —CH$_2$NHC(=O)OMe, —CH$_2$NHC(=O)CF$_3$, morpholino, —CH$_2$NH$_2$, —C(=O)Ph, —OCH$_2$-isoxazolyl, —NH-pyrimidinyl, pyridizinyl, pyrimidinyl, pyridinyl, pyrazolyl, methylpyrazolyl, dimethylpyrazolyl, pyrazinyl, pyridazinyl, methyloxadiazolyl, oxadiazolyl, dimethyloxadiazolyl, isoxazolyl, dimethyltriazolyl, imidazolyl, benzimidazolyl and thiadiazolyl.

It may be further preferred in these embodiments that the optional substituents are selected from: ethoxy, —C(=O)-morpholino (which may be bridged or substituted by one of two methyl groups), methyloxadiazolyl, cyclopropyloxadiazolyl, t-butyloxadiazolyl, cyclopropyltriazolyl, and 5,6,7,8-tetrahydroimidazo[1,5-a]pyridin-3-yl.

It may be preferred in these embodiments that, when the optional substituent is a C$_{5-6}$ heteroaryl group, the heteroaryl ring itself is substituted with one or more C$_{1-4}$ alkyl groups.

It may be preferred in the above embodiments that 1 substituent is present. In may be preferred in the above embodiments that 2 substituents are present.

Halo and methoxy (including CF$_3$O) substituents may be preferred in the ortho position of the phenyl group. Ethoxy and alkyl (e.g. methyl, CF$_2$H and CF$_3$) substituents may also be preferred in the ortho position of the phenyl group. Alkyl and C$_{5-6}$ heteroaryl may be preferred in the meta position of the phenyl group. Amido and amidomethyl substituents may be preferred in the para position of the phenyl group. Particular favoured groups in the ortho position are ethoxy, methoxy, Cl, F and CF$_2$H.

In some embodiments, the phenyl group bears a halo or methoxy substituent in the ortho position, and an amido or amidomethyl substituent in the para position of the phenyl group.

In some embodiments, the phenyl group bears an amino substituent in the meta position.

Where the substituent on phenyl is a fused $C_{5-6}$ $N_1$-containing heterocyclic ring, A may have a core structure selected from:

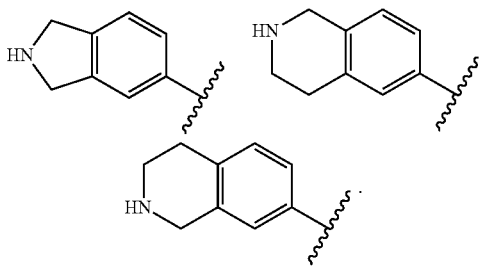

Particular A groups of interest include:

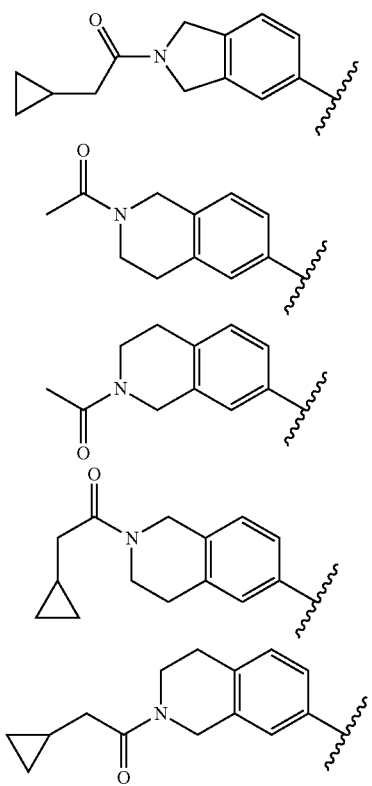

Optionally Substituted Naphthyl

When A is naphthyl, it may be in any orientation, e.g. naphth-1-yl, naphth-2-yl.

In some embodiments A may be optionally substituted naphthyl.

In some of these embodiments, A is unsubstituted naphthyl.

In some of these embodiments, the naphthyl ring of A has 1, 2, 3, 4 or 5 substituents.

In some of these embodiments, the naphthyl ring of A has 1 or 2 substituents.

It may be preferred in some of these some of these embodiments that $R^{1-6}$ and n and p are such that the compound is of formula Ia, Ib or Ic.

It may be preferred in these embodiments that the optional substituents refers to 0-2 substituents independently selected from the following: $C_{1-4}$ alkyl; $C_{1-4}$ fluoroalkyl; $C_{3-6}$ cycloalkyl; $C_{5-6}$ heteroaryl; $C_{5-6}$ heteroaryl methyl; $C_{4-6}$ heterocyclyl; $C_{4-6}$ heterocyclyl methyl; phenyl; benzyl; halo; amido; amidomethyl; acylamido; acylamidomethyl; $C_{1-4}$ alkyl ester; $C_{1-4}$ alkyl ester methyl; $C_{1-4}$ alkyl carbamoyl; $C_{1-4}$ alkyl carbamoyl methyl; $C_{1-4}$ alkylacyl; $C_{1-4}$ alkyl acyl methyl; phenylcarbonyl; carboxy; carboxymethyl; ether; amino; aminomethyl; sulfonamido; sulfonamino; sulfone; nitrile; and nitrilemethyl.

It may be preferred in these embodiments that 1 substituent is present. In may be preferred in these embodiments that 2 substituents are present.

Optionally Substituted $C_{5-12}$ Heteroaryl

In some embodiments A may be an optionally substituted $C_{5-12}$ heteroaryl group.

In some of these embodiments, A is unsubstituted $C_{5-12}$ heteroaryl group.

In some of these embodiments, the $C_{5-12}$ heteroaryl of A has 1, 2, 3, 4 or 5 substituents. In some of these embodiments, the $C_{5-12}$ heteroaryl of A has 1 or 2 substituents.

It may be preferred in these embodiments that the $C_{5-12}$ heteroaryl ring is selected from one of the following: pyridinyl, pyrimidinyl, pyrazinyl, isoxazolyl, oxazolyl, thiophenyl, thiazolyl, thiadiazolyl, pyrazolyl, pyridonyl, imidazolyl, benzimidazolyl, imidazopyridinyl and quinolinyl. The heteroatoms may be in any location in the ring, which may be joined to the remainder of the molecule via a ring carbon atom. It may be further preferred that the $C_{5-12}$ heteroaryl ring is either pyridinyl or pyrimidinyl. It may also be further preferred that the $C_{5-12}$ heteroaryl is selected from pyridyl, pyrimidinyl, oxazolyl, oxadiazolyl, pyrazolyl and thiazolyl and in particular:

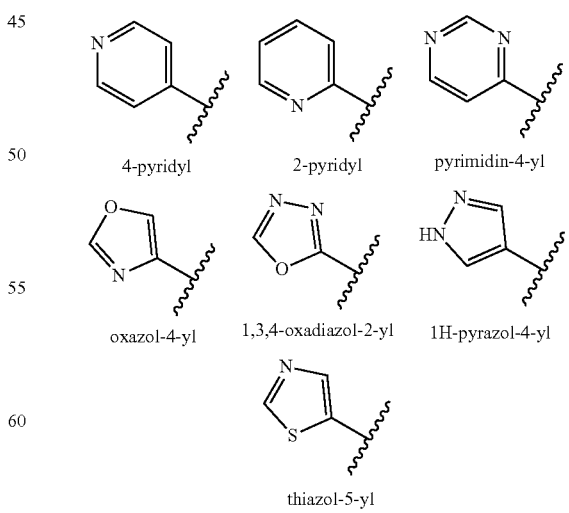

Further preferred groups may include benzothiazolyl and benzimidazolyol and in particular:

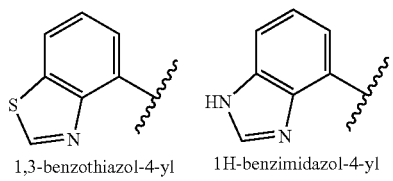 [SMILES: *c1cccc2scnc12 ; *c1cccc2[nH]cnc12]

1,3-benzothiazol-4-yl    1H-benzimidazol-4-yl

It may be preferred in some of these some of these embodiments that $R^{1-6}$ and n and p are such that the compound is of formula Ia, Ib or Ic.

It may be preferred in these embodiments that the optional substituents are independently selected from the following: $C_{1-4}$ alkyl; $C_{1-4}$ fluoroalkyl; $C_{3-6}$ cycloalkyl; $C_{5-6}$ heteroaryl; $C_{5-6}$ heteroaryl methyl; $C_{4-6}$ heterocyclyl; $C_{4-6}$ heterocyclyl methyl; phenyl; benzyl; halo; amido; amidomethyl; acylamido; acylamidomethyl; $C_{1-4}$ alkyl ester; $C_{1-4}$ alkyl ester methyl; $C_{1-4}$ alkyl carbamoyl; $C_{1-4}$ alkyl carbamoyl methyl; $C_{1-4}$ alkylacyl; $C_{1-4}$ alkyl acyl methyl; phneylcarbonyl; carboxy; carboxymethyl; ether; amino; aminomethyl; sulfonamido; sulfonamino; sulfone; nitrile; and nitrilemethyl.

It may be preferred in these embodiments that the optional substituents are selected from: $C_{1-4}$ alkyl; $C_{1-4}$ fluoroalkyl; $C_{5-6}$ heteroaryl, $C_{4-6}$ heterocyclyl; phenyl; halo; and ether.

It may be preferred in these embodiments that the optional substituent are selected from; methyl, ethyl, butyl, chloro, bromo, fluoro, morpholino, pyrrolidinyl, —OBn, —OPh, phenyl, para-bromophenyl, pyrazolyl, pyrimidinyl, imidazolyl and —$CF_3$.

In may be preferred in these embodiments that 1 substituent is present. In may be preferred in these embodiments that 2 substituents are present.

Halo and methoxy substituents may be preferred in the ortho position of a $C_6$ heteroaryl group, or α-position of $C_5$ and $C_{7-12}$ heteroaryl group. Amido and amidomethyl substituents may be preferred in the para position of a $C_6$ heteroaryl group, or γ-position of $C_5$ and $C_{7-12}$ heteroaryl group.

In some embodiments, a $C_6$ heteroaryl group bears a halo or methoxy substituent in the ortho position, and an amido or amidomethyl substituent in the para position.

In some embodiments, a $C_6$ heteroaryl group bears an amino substituent in the meta position. In some embodiments, a $C_5$ or $C_{7-12}$ heteroaryl group bears an amino substituent in the β-position.

Where the $C_6$ heteroaryl group is 4-pyridyl, it may bear an ether substituent, for example in the 3-position. In some of these embodiments, the ether substituent may be —O—$C_{4-6}$ heterocyclyl, wherein the $C_{4-6}$ heterocyclyl may itself bear an ester group (e.g. methoxy ester). It may alternatively bear an amino substituent, for example in the 3-position. In some of these embodiments, the amino substituent may be —NH—$C_{4-6}$ heterocyclyl, wherein the $C_{4-6}$ heterocyclyl may itself bear an ester group (e.g. —C(=O)OMe).

Where the $C_6$ heteroaryl group is 2-pyridyl, it may bear an amido substituent, for example in the 4-position.

Where the $C_6$ heteroaryl group is 4-pyrimidinyl, it may bear an amino substituent, for example in the 3-position. In some of these embodiments, the amino substituent may be —NH—$C_{4-6}$ heterocyclyl, wherein the $C_{4-6}$ heterocyclyl may itself bear an acyl group (e.g. —C(=O)Me).

Where A is a $C_5$ heteroaryl group (e.g. oxazolyl, oxadiazolyl, pyrazolyl and thiazolyl), it may bear an amino, phenyl or $C_6$ heteroaryl substituent in the β-position.

In some embodiments A is selected from one of the following groups:

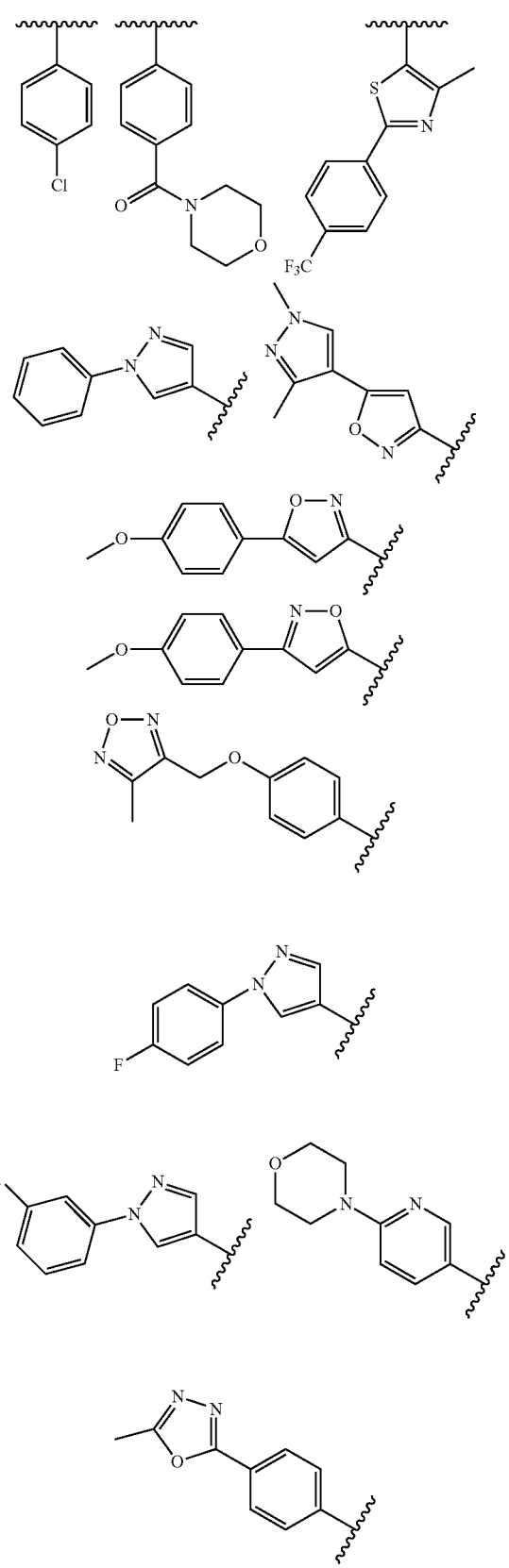

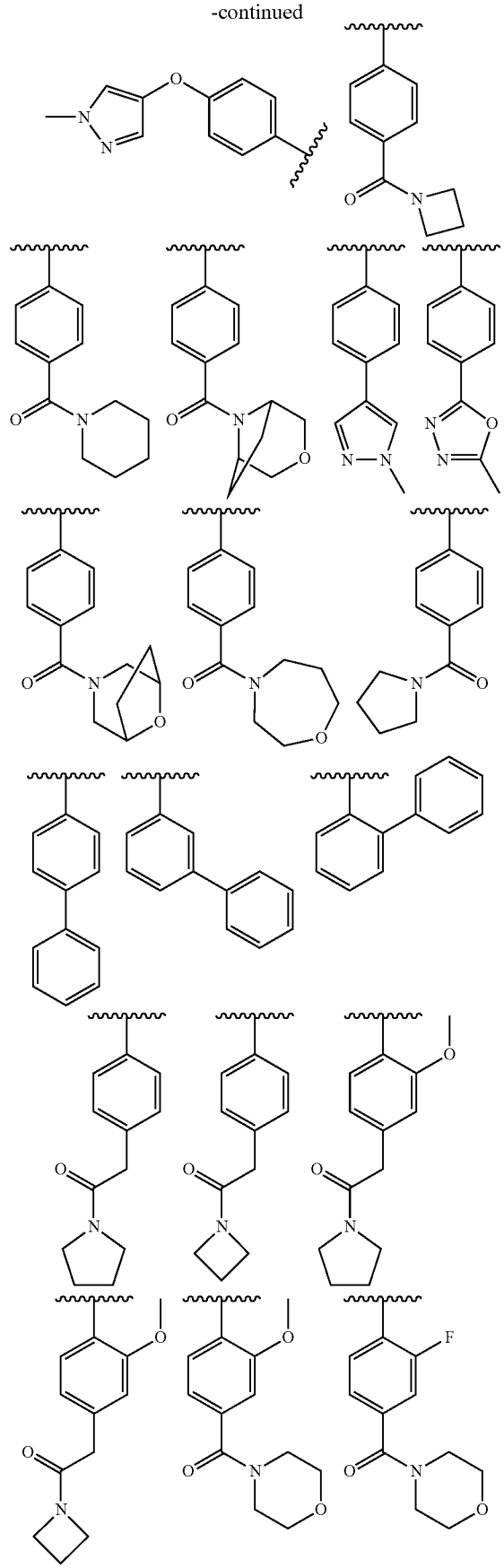
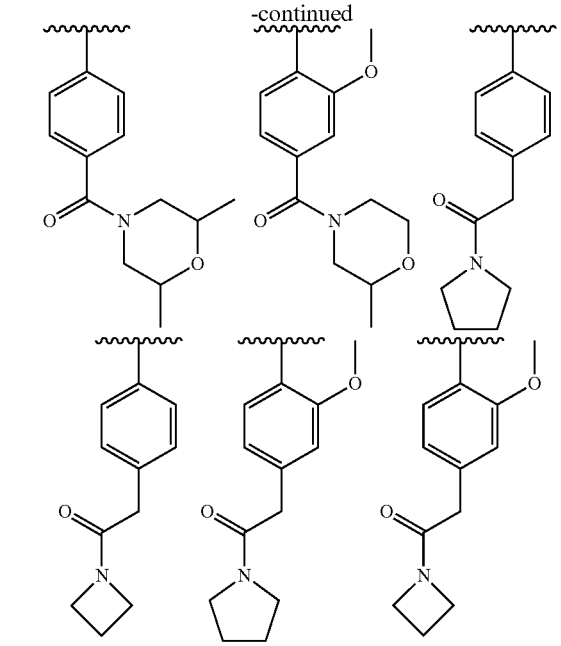
In some embodiments A may be selected from one of the following groups:
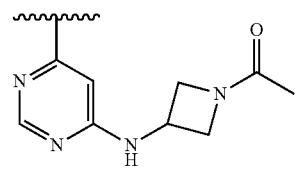
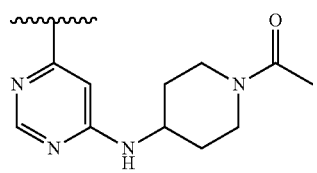
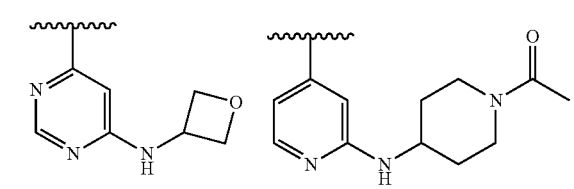
In further embodiments, it may be preferred that A is selected from one of the following groups:
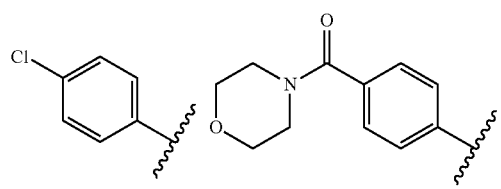

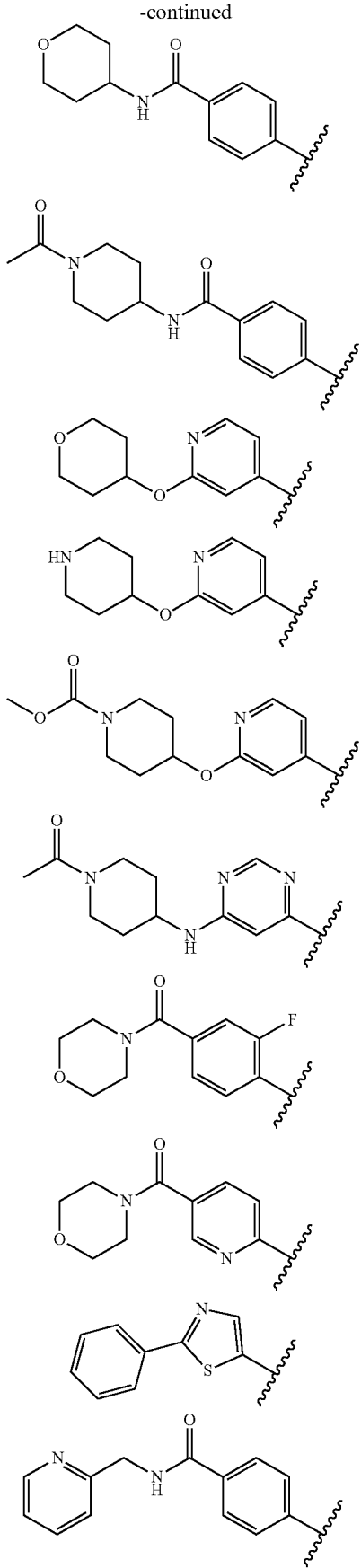
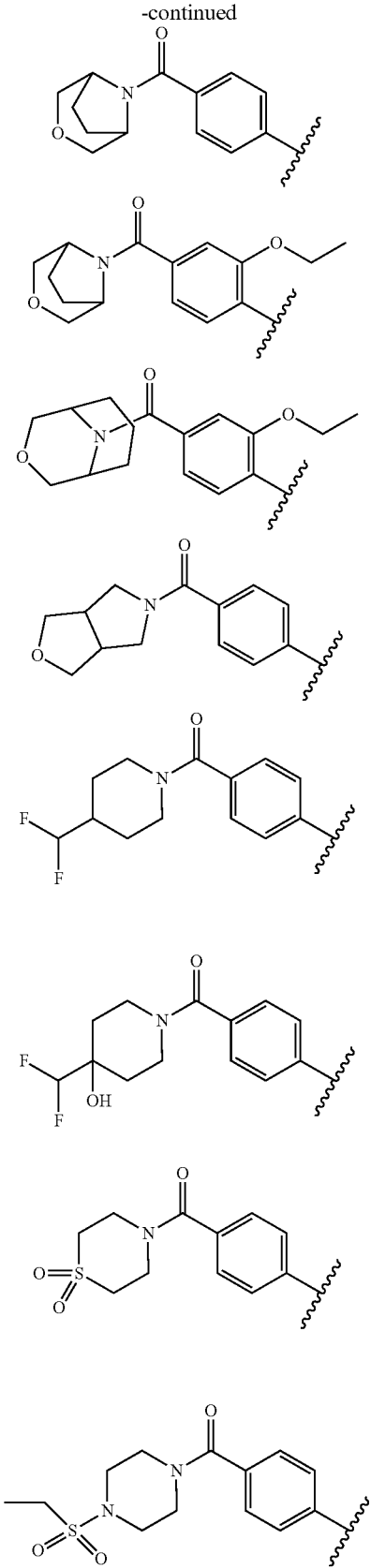
In further embodiments, it may be preferred that A is selected from one of the following groups:

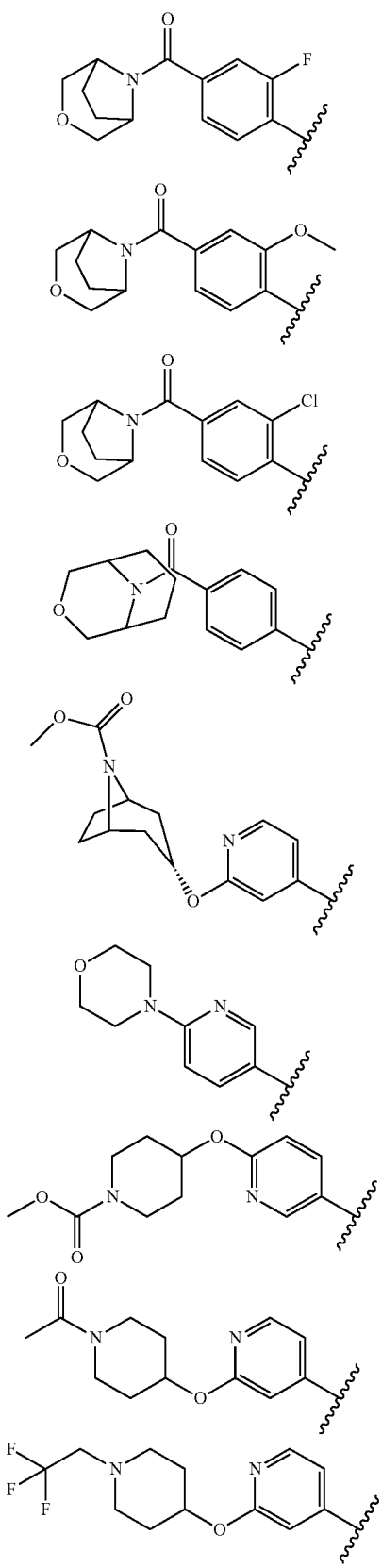

phenyl with a para-amido substituent;

phenyl with a para-amido substituent, and an ortho-ethoxy group;

pyridyl with para ether or amino group, where the ether or amino substituent is a $C_{5-6}$ heterocyclic group—in these groups, the pyridyl N may be in the meta position; these groups may also have (in some embodiments) an ortho-ethoxy group; and pyridyl with a meta ether group, where the pyridyl N is in the para position.

In further embodiments, it may be preferred that A is selected from:

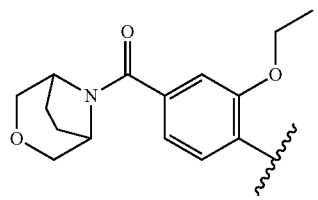

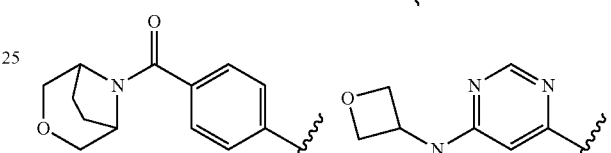

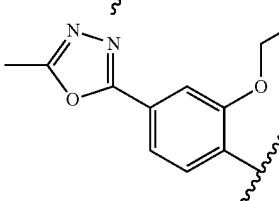

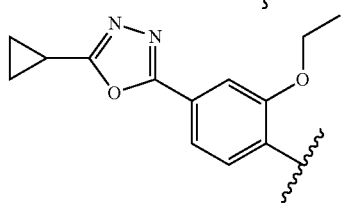

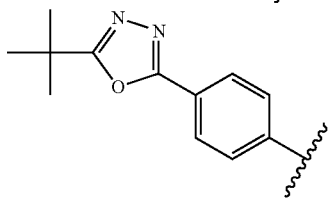

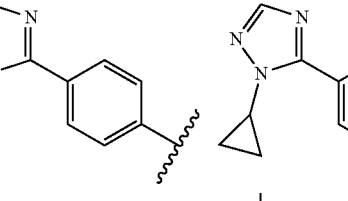

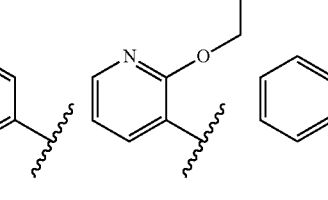

In other further embodiments, the A group may be selected from:

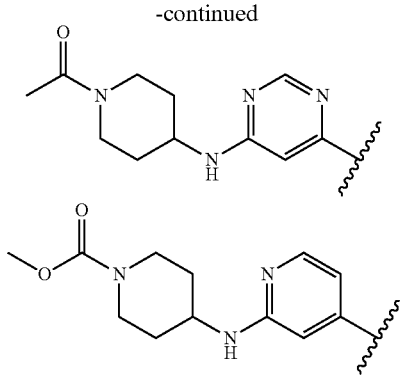

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), isopropyl (iPr), n-butyl (nBu), tert-butyl (tBu), phenyl (Ph), benzyl (Bn), methoxy (MeO), ethoxy (EtO), trimethylsilyl (TMS), and acetyl (Ac).

For convenience, many chemical compounds are represented using well known abbreviations, including but not limited to, methanol (MeOH), deuterated methanol ($d_4$-MeOD, $CD_3OD$), ethanol (EtOH), isopropanol (i-PrOH), ether or diethyl ether ($Et_2O$), ethyl acetate (EtOAc), acetic acid (AcOH), acetonitrile (MeCN, ACN), dichloromethane (methylene chloride, DCM), trifluoroacetic acid (TFA), N,N-dimethylformamide (DMF), tetrahydrofuran (THF), dimethylsulfoxide (DMSO), deuterated chloroform ($CDCl_3$), diethylamine (DEA), deuterated dimethylsulfoxide ($d_6$-DMSO), N-ethyl-N'-(3-dimethylaminopropyl)carbodiimide (EDC), N-ethyl-N'-(3-dimethylaminopropyl)carbodiimide hydrochloride (EDCI.HCl, EDCI), meta-chloroperoxybenzoic acid (mCPBA), 1,1'-bis(diphenylphosphino)ferrocene (dppf), tert-butyloxycarbonyl (Boc, BOC), 2-(trimethylsilyl)ethoxymethyl (SEM), triethylamine ($Et_3N$), 2-(1H-7-azabenzotriazol-1-yl)-1,1,3,3-tetramethyluronium hexafluorophosphate (HATU), 4-dimethylaminopyridine (DMAP), N,N-diisopropylethylamine (DIEA, DIPEA), 1,1'-bis(diphenylphosphino)ferrocene dichloropalladium (II) ($PdCl_2(dppf)$), trans-dichlorobis(triphenylphosphine)palladium(II) ($PdCl_2(PPh_3)_2$), tris(dibenzylideneacetone) dipalladium(0) ($Pd_2(dba)_3$), tetrakis(triphenylphosphine)palladium(0) ($Pd(PPh_3)_4$), propylphosphonic anhydride (T3P), and 1-hydroxybenzotriazole (HOBt), hexamethylphosphoramide (HMPA), triethylamine (TEA), dichloroethane (DCE), N-bromosuccinimide (NBS), N-N'-dicyclohexylcarbodiimide (DCC), p-toluenesulfonic acid (TsOH), 1,1'-carbonyldiimidazole (CDI), carbon monoxide (CO), dithiothreitol (DTT), fluorenylmethyloxycarbonyl (Fmoc), hydrochloric acid (HCl), methyl tert-butyl ether (MTBE), ammonium bicarbonate ($NH_4HCO_3$), phosphorus (V) oxychloride ($POCl_3$), thionyl chloride ($SOCl_2$).

For convenience, many further terms are represented using well known abbreviations, including but not limited to, bovine serum albumin (BSA), degree Celsius (° C.), gram (g), hour (h), high performance liquid chromatography (HPLC), liquid chromatography and mass spectrometry (LCMS), molar (M), mass spectrometry (MS), millimole (mmol), milligram (mg), minute (min), milliliter (mL), nanomolar (nM), normal (N), nuclear magnetic resonance (NMR), pound per square inch (psi), thin layer chromatography (TLC), preparative thin layer chromatography (prep-TLC), microliter (μL).

General Experimental Details for Intermediate Preparations and Examples 1 to 3

Unless otherwise stated the following generalisations apply. $^1H$ NMR spectra were recorded on a Bruker Ultrashield Plus (400 MHz) or a Bruker AVANCE (400 MHz). The multiplicity of a signal is designated by the following abbreviations: s, singlet; d, doublet; t, triplet; q, quartet; dd, doublet of doublets; dt, doublet of triplets; tt, triplet of triplets; br, broad; m, multiplet. All observed coupling constants, J, are reported in Hertz.

LCMS data was generated using either an Agilent 6100 Series Single Quad LCMS (LCMS-A), an Agilent 1260 Infinity Series UPLC/MS (LCMS-B), an Agilent 1200 Series G6110A Quadrupole LCMS or Waters 2695 alliance (LCMS-C). Chlorine isotopes are reported as $^{35}Cl$, Bromine isotopes are reported as either $^{79}Br$ or $^{81}Br$ or both $^{79}Br/^{81}Br$.

LCMS Method A (LCMS-A):
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC conditions:
Reverse Phase HPLC analysis
Column: Luna C8 (2) 5 μm 50×4.6 mm 100 Å
Column temperature: 30° C.
Injection Volume: 5 μL
Solvent A: Water 0.1% Formic Acid
Solvent B: MeCN 0.1% Formic Acid
Gradient: 5-100% solvent B over 10 min
Detection: 254 nm or 214 nm
MS conditions:
Ion Source: Quadrupole
Ion Mode: Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min
LCMS Method B (LCMS-B):
Instrument: Agilent 1260 Infinity Series UPLC/MS
Pump: 1260 Infinity G1312B Binary pump
Autosampler: 1260 Infinity G1367E 1260 HiP ALS
Detector: 1290 Infinity G4212A 1290 DAD
LC conditions:
Reverse Phase HPLC analysis
Column: Poroshell 120 EC-C18 2.7 μm 50×3.0 mm
Column temperature: 35° C.
Injection Volume: 1 μL
Solvent A: Water 0.1% Formic Acid
Solvent B: MeCN 0.1% Formic Acid
Gradient: 5-100% solvent B over 3.8 min
Detection: monitored at 254 nm and 214 nm
MS conditions:
Ion Source: Quadrupole Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min
LCMS Method C (LCMS-C):
Instrument: Agilent 1200 Series G6110A Quadrupole
Pump: Binary pump
Detector: DAD
LC conditions:
Reverse Phase HPLC analysis
Column: Xbridge-C18, 2.5 μm, 2.1×30 mm
Column temperature: 30° C.
Injection Volume: 1-10 μL
Solvent A: Water 0.07% Formic acid
Solvent B: Methanol
Gradient: 30-95% solvent B over 3.5 min (for medium polarity samples) or 10-95% solvent B over 3.7 min (for large polarity samples)
Detection: monitored at 254 nm and 214 nm
MS conditions:
Ion Source: Quadrupole
Ion Mode: ES+
Drying gas temp: 350° C.
Drying gas flow: 10 L/min
Nebulizer pressure: 35 psi
Capillary voltage (V): 3500 (positive)
Scan Range: 50-900
Or
Instrument: Waters 2695 alliance
Pump: Quaternary Pump
Detector: 2996 Photodiode Array Detector
MS model: Micromass ZQ
LC conditions:
Column: Xbridge-C18, 3.5 μm, 2.1×50 mm
Column temperature: 30° C.
Injection volume: 1-10 μL
Acquisition of wavelength: 214 nm, 254 nm
Solvent A: 0.07% HCOOH aqueous solution
Solvent B: MeOH
Run time: 8 min
Gradient: 20-95% solvent B over 5 min
Detection: 254 nm and 214 nm
MS condition:
Ion source: ES+ (or ES−) MS range: 50~900 m/z
Capillary: 3 kV Cone: 3 V Extractor: 3 V
Drying gas flow: 600 L/hr cone: 50 L/hr
Desolvation temperature: 300° C.
Source temperature: 100° C.
Sample Preparation:
The sample was dissolved in methanol, the concentration about 0.1-1.0 mg/mL, then filtered through the syringes filter with 0.22 μm.
Preparative RP-HPLC:
Agilent 1260 Infinity HPLC system
UV detection at 210 nm and 254 nm
Gradient or isocratic elution through a Phenomenex Luna C8 (2) column 100 Å Axia (250×21.2 mm; particle size 5 μm)
Flow rate: 10 mL/min
Gradients are as specified in the individual examples.
Analytical thin-layer chromatography was performed on Merck silica gel 60 F254 aluminium-backed plates which were visualised using fluorescence quenching under UV light or a basic $KMnO_4$ dip or Ninhydrin dip.

Preparative thin-layer chromatography (prep TLC) was performed using Tklst (China), grand grade: (HPTLC): 8±2 μm>80%; (TLC): 10-40 μm. Type: GF254. Compounds were visualised by UV (254 nm).
Preparative LCMS (Method A)
Instrument:
Agilent 1200 series LC
Agilent 6120 Quadrupole Mass Detector
Agilent G1968D Active Splitter
LC conditions:
Reverse Phase HPLC analysis
Column: Zorbax SB-C18 5 μm 9.4×50 mm
Injection loop volume: 900 μL
Solvent A: Water plus 0.1% TFA
Solvent B: Acetonitrile plus 0.1% TFA
Gradient: 5-100% B over 6 min, hold 100% B for 1.5 min
Flow rate: 4 mL/min
Detection: 254 nm
MS conditions:
Ion Source: Quadrupole
Ion Mode: ES
Vaporiser Temp: 200° C.
Gas Temp: 300° C.
Capillary voltage positive (V): 4000
Capillary voltage negative (V): 4000
Scan Range: 100-700 Amu
Acquisition time: 10 min
Isocratic Pump (make-up flow):
Flow rate: 0.5 mL/min
Solvent: 50:50 water:acetonitrile plus 0.1% formic acid
Flash chromatography was performed using a Biotage Isolera purification system using either Grace or RediSep® silica cartridges.
Column chromatography was performed using Tklst (China), grand grade, 100-200 meshes silica gel.
Microwave irradiation was achieved using a CEM Explorer SP Microwave $R^{2a}$ctor.
Where necessary, anhydrous solvents were purchased from Sigma-Aldrich or dried using conventional methods. Solutions of inorganic acids or bases where made up as aqueous solutions unless stated otherwise.
Additional Cartridges used are as follows:
Phase Separator:
Manufacturer: Biotage
Product: ISOLUTE® Phase Separator (3 mL unless otherwise stated)
SCX and SCX-2 Cartridges:
Manufacturer: Biotage
Product: ISOLUTE® SCX 1 g, (6 mL SPE Column unless otherwise stated)
Manufacturer: Biotage
Product: ISOLUTE® SCX-2 1 g (6 mL Column)
Manufacturer: Silicycle
Product: SCX-2 500 mg or 5 g
Manufacturer: Agilent
Product: Bond Elut® SCX 10 g Sample Extraction Cartridge:
Manufacturer: Waters
Product: Oasis® HLB 35 cc (6 g) LP extraction cartridge
Intermediate Preparations (i) 4-(3-Oxa-8-azabicyclo[3.2.1]octane-8-carbonyl)-2-ethoxybenzoic acid I4

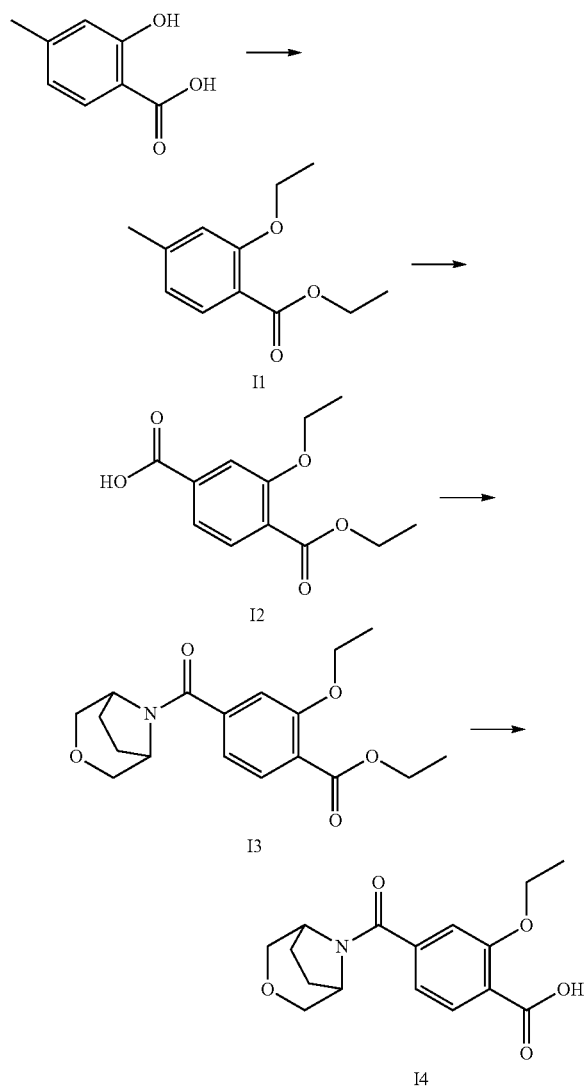

(a) Ethyl-2-ethoxy-4-methylbenzoate I1

To a mixture of 2-hydroxy-4-methylbenzoic acid (8.2 g, 53.9 mmol) and $K_2CO_3$ (22.4 g, 161.7 mmol) in dimethylsulfoxide (70 mL) at 40° C. was added and ethyl iodide (12.6 g, 80.8 mmol) dropwise over a period of 30 min. The reaction was stirred for 2 h then further ethyl iodide (12.6 g, 80.8 mmol) was added over 30 min. The resulting mixture was stirred a further 8 h at 40° C., then diluted with $CH_2Cl_2$ (150 mL) and filtered. The filtrate was washed with water (200 mL×10) and brine (200 mL×2), dried ($Na_2SO_4$) and concentrated to give the desired compound as a yellow liquid (10.1 g, 90%): LCMS: RT 2.70 min; m/z 209.1 $[M+H]^+$.

(b) 3-Ethoxy-4-(ethoxycarbonyl)-benzoic acid I2

To a solution of ethyl 2-ethoxy-4-methylbenzoate I1 (10.0 g, 48.1 mmol) in a mixture of pyridine (25 mL) and water (75 mL) was added $KMnO_4$ (22.8 g, 144.2 mmol). The resulting mixture was heated at 50° C. for 48 h, then cooled and allowed to stir at room temperature for 24 h. The mixture was filtered and the filter cake washed with hot water. The combined aqueous filtrates were washed with EtOAc (75 mL×3) and acidified with 2M aqueous HCl solution. The mixture was extracted with $CH_2Cl_2$ (150 mL×3). The combined organic layers were washed with brine, dried ($Na_2SO_4$) and concentrated to give the desired compound as a white solid (5.0 g, 44%): LCMS: RT 0.25 min; m/z 239.0 $[M+H]^+$.

(c) Ethyl 4-(3-oxa-8-azabicyclo[3.2.1]octane-8-carbonyl)-2-ethoxybenzoate I3

To a solution of 3-ethoxy-4-(ethoxycarbonyl)benzoic acid I2 (2.5 g, 10.4 mmol) in $CH_2Cl_2$ (20 mL) was added 3-oxa-8-azabicyclo[3.2.1]octane hydrochloride (1.42 g, 9.5 mmol), HOBt (135.1 mg, 1.0 mmol), DIPEA (2.5 g, 19.0 mmol) and EDCI (2.2 g, 11.4 mmol). The resulting mixture was stirred at room temperature overnight. The mixture was partitioned with saturated aqueous $NaHCO_3$, and extracted with $CH_2Cl_2$ (20 mL×2). The combined organic layers were washed with brine, dried ($Na_2SO_4$) and concentrated. The residue was purified by column chromatography (1% methanol in dichloromethane) to give the desired compound as a yellow oil (2.5 g, 80%): LCMS: RT 2.40 min; m/z 334.1 $[M+H]^+$.

(d) 4-(3-Oxa-8-azabicyclo[3.2.1]octane-8-carbonyl)-2-ethoxybenzoic acid I4

To a solution of ethyl-4-(3-oxa-8-azabicyclo-[3.2.1]-octane-8-carbonyl)-2-ethoxybenzoate I3 (2.4 g, 7.2 mmol) in a mixture of THF (20 mL), methanol (2 mL) and water (2 mL) was added LiOH $H_2O$ (1.5 g, 36 mmol). The resulting mixture was stirred at room temperature for 24 h. The solvent was removed, and the residue obtained diluted with water (20 mL). The pH of the aqueous mixture was adjusted to 6 by addition of a 2 M aqueous HCl solution. The mixture was extracted with $CH_2Cl_2$ (20 mL×3) and the combined organic layers washed with brine (10 mL×2), dried ($Na_2SO_4$) and concentrated to give the desired compound as a yellow oil (1.7 g, 79%): $^1$H NMR (400 MHz, $d_4$-MeOD) δ 7.83 (d, J=7.8 Hz, 1H), 7.19 (d, J=1.0 Hz, 1H), 7.10 (dd, J=7.8, 1.3 Hz, 1H), 4.65 (br s, 1H), 4.20 (q, J=7.0 Hz, 2H), 3.97 (br s, 1H), 3.82 (d, J=10.8 Hz, 1H), 3.72 (d, J=11.0 Hz, 2H), 3.59 (d, J=10.9 Hz, 1H), 2.13-1.94 (m, 4H), 1.45 (t, J=7.0 Hz, 3H). LCMS: RT 1.20 min; m/z 306.1 $[M+H]^+$.

(ii) 4-(3-Oxa-8-azabicyclo[3.2.1]octane-8-carbonyl)benzoic acid I6

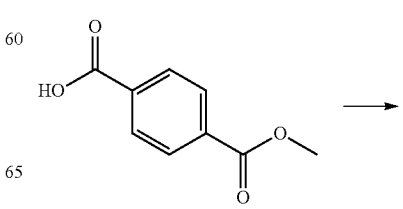

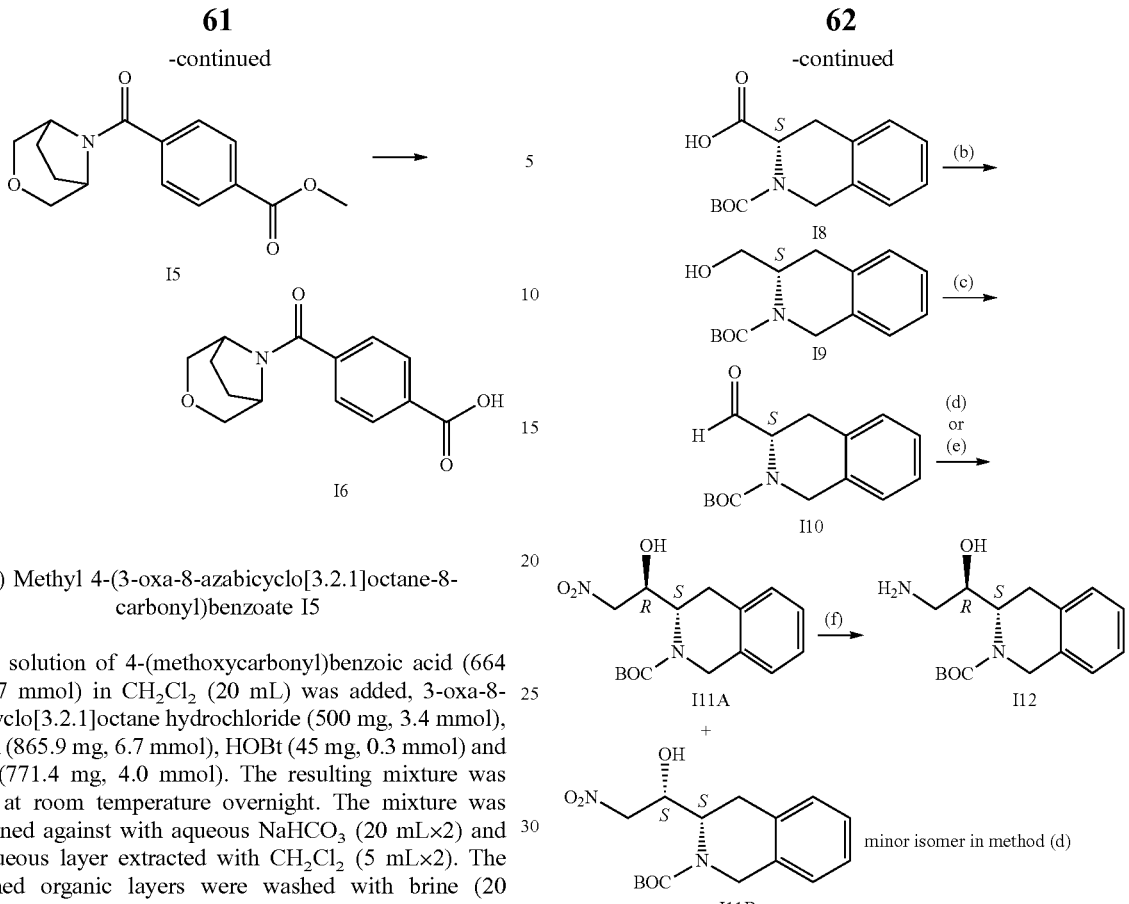

(a) Methyl 4-(3-oxa-8-azabicyclo[3.2.1]octane-8-carbonyl)benzoate I5

To a solution of 4-(methoxycarbonyl)benzoic acid (664 mg, 3.7 mmol) in CH$_2$Cl$_2$ (20 mL) was added, 3-oxa-8-azabicyclo[3.2.1]octane hydrochloride (500 mg, 3.4 mmol), DIPEA (865.9 mg, 6.7 mmol), HOBt (45 mg, 0.3 mmol) and EDCI (771.4 mg, 4.0 mmol). The resulting mixture was stirred at room temperature overnight. The mixture was partitioned against with aqueous NaHCO$_3$ (20 mL×2) and the aqueous layer extracted with CH$_2$Cl$_2$ (5 mL×2). The combined organic layers were washed with brine (20 mL×2), dried (Na$_2$SO$_4$) and concentrated. The crude residue obtained was purified by column chromatography (1% methanol in CH$_2$Cl$_2$) to give the desired compound as a white solid (786.9 mg, 85%): LCMS: RT 0.61 min; m/z 276.1 [M+H]$^+$.

(b) 4-(3-Oxa-8-azabicyclo[3.2.1]octane-8-carbonyl)benzoic acid I6

To a solution of methyl 4-(3-oxa-8-azabicyclo[3.2.1]octane-8-carbonyl)benzoate I5 (770 mg, 2.8 mmol) in a mixture of THF (20 mL), methanol (2 mL) and water (2 mL) was added LiOH.H$_2$O (587.8 mg, 14.0 mmol). The resulting mixture was stirred at room temperature overnight, then the solvent removed and the residue obtained diluted with water (20 mL). The pH of the aqueous solution was adjusted to 6 by addition of a 2 M aqueous HCl solution. The aqueous layer was extracted with CH$_2$Cl$_2$ (20 mL×3) and the combined organic layers washed with brine (20 mL×2), dried (Na$_2$SO$_4$) and concentrated to give the desired compound (460 mg, 63%) as a white solid: LCMS: RT 0.83 min; m/z 262.1 [M+H]$^+$.

(iii) tert-Butyl (S)-3-((R)-2-amino-1-hydroxyethyl)-3,4-dihydroisoquinoline-2(1H)-carboxylate (I12)

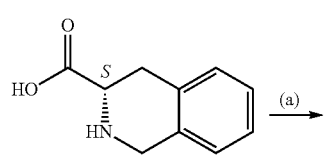

(a) (S)-2-(tert-Butoxycarbonyl)-1,2,3,4-tetrahydroisoquinoline-3-carboxylic acid (I8)

(S)-1,2,3,4-Tetrahydroisoquinoline-3-carboxylic acid (5.00 g, 28.2 mmol) was vigorously stirred in 1,4-dioxane (100 mL) and water (50 mL). Sodium bicarbonate (4.74 mg, 56.4 mmol) and Boc anhydride (6.77 g, 31.0 mmol) were added and the mixture was stirred vigorously at room temperature. After 17 hours the mixture was concentrated in vacuo and the residue dissolved in water (200 mL). A 30% w/v aqueous solution of sodium hydrogen sulfate monohydrate (30 mL) was added and the mixture extracted with chloroform (3×200 mL). The pooled organic extracts were washed with brine, dried over sodium sulfate and concentrated in vacuo to give the desired compound (7.50 g, 96% yield) as a thick syrup. LCMS-B: RT 3.64 min; m/z 178.1 [M-Boc+2H]$^+$; m/z 276.1 [M-H]$^-$

(b) tert-Butyl (S)-3-(hydroxymethyl)-3,4-dihydroisoquinoline-2(1H)-carboxylate (I9)

(S)-2-(tert-Butoxycarbonyl)-1,2,3,4-tetrahydroisoquinoline-3-carboxylic acid (I8) (7.50 g, 27.0 mmol) was dissolved in THF (150 mL) and CDI (8.77 g, 54.1 mmol) was added. The mixture was stirred for 30 minutes at room temperature then cooled to 0° C. A solution of sodium borohydride (1.16 g, 30.5 mmol) in water (15 mL) was added dropwise. After 40 minutes the mixture was quenched with acetone (25 mL) and concentrated in vacuo. The residue was partitioned between water (250 mL) and ethyl acetate (200 mL). The separated aqueous phase was extracted with ethyl acetate (2×250 mL), the combined organic extracts washed with 5% w/v aqueous NaHSO$_4$ (250 mL), brine (200 mL), dried over sodium sulfate and concentrated in vacuo. The residue was loaded in diethyl ether (50 mL) onto a plug of basic alumina and silica (50 mL each). The plug was eluted with diethyl ether (250 mL) and the eluate evaporated to give the desired compound (5.93 g, 83% yield) as a colourless syrup. $^1$H NMR (400 MHz, CDCl$_3$) δ 7.25-7.06 (m, 4H), 4.82-4.59 (m, 1H), 4.57-4.38 (m, 1H), 4.37-4.19 (m, 1H), 3.57-3.40 (m, overlaps with trace solvent), 3.03 (dd, J=16.1, 5.7 Hz, 1H), 2.80 (d, J=16.1 Hz, 1H), 1.50 (s, 9H). LCMS-B: RT 3.66 min; m/z 164.2 [M-Boc+2H]$^+$, 286.2 [M+Na]$^+$ (c) tert-Butyl (S)-3-formyl-3,4-dihydroisoquinoline-2(1H)-carboxylate (I10)

tert-Butyl (S)-3-(hydroxymethyl)-3,4-dihydroisoquinoline-2(1H)-carboxylate (I9) (1.50 g, 5.70 mmol), DCM (25 mL) and DMSO (5 mL) were cooled to 0° C. Triethylamine (2.38 mL, 17.1 mmol) was added, followed by pyridine-sulfur trioxide complex (2.72 g, 17.1 mmol). The mixture was stirred at 0° C. for 10 minutes then allowed to come to room temperature. After 2 hours, saturated sodium bicarbonate (75 mL) and water (75 mL) were added, and the mixture extracted with diethyl ether (3×150 mL). The pooled ether extracts were washed with 1:1 water:saturated aqueous NH$_4$Cl (200 mL), brine (200 mL), dried over sodium sulfate and concentrated in vacuo to give the desired compound as a colourless oil which was used without further purification.

(d) tert-Butyl (S)-3-((R)-1-hydroxy-2-nitroethyl)-3,4-dihydroisoquinoline-2(1H)-carboxylate (I11A) and tert-butyl (S)-3-((S)-1-hydroxy-2-nitroethyl)-3,4-dihydroisoquinoline-2(1H)-carboxylate (I11B)

A solution of tert-butyl (S)-3-formyl-3,4-dihydroisoquinoline-2(1H)-carboxylate (I10) (5.70 mmol @100% conversion) in i-propanol (50 mL) was cooled to 0° C. Nitromethane (1.22 mL, 22.8 mmol) and potassium fluoride (331 mg, 5.70 mmol) were added and the mixture stirred for 18 hours, allowing the temperature to come to room temperature as the ice bath thawed. The mixture was diluted with water (200 mL) and extracted with DCM (3×200 mL). The pooled DCM extracts were washed with brine, dried over sodium sulfate and concentrated in vacuo. Chromatography (40 g silica cartridge, 0-20% ethyl acetate/hexanes) gave two partly overlapping peaks, which were split into early (11A major, colourless syrup, 697 mg, 37% yield) and late (11B minor, colourless syrup, 170 mg, 9% yield) fractions. Overall: 867 mg, 47% yield.

Data for major isomer tert-butyl (S)-3-((R)-1-hydroxy-2-nitroethyl)-3,4-dihydroisoquinoline-2(1H)-carboxylate I11A:

$^1$H NMR (400 MHz, d$_4$-MeOD) δ 7.25-7.14 (m, 4H), 4.85-4.49 (m, 5H), 4.44 (dd, J=12.6, 9.3 Hz, 1H), 4.37-3.99 (m, overlaps with solvent), 3.19 (dd, J=15.9, 3.2 Hz, 1H), 2.92 (dd, J=15.8, 5.6 Hz, 1H), 1.51 (s, 9H). LCMS-B: RT 3.71 min; m/z 223.2 [M-Boc+2H]$^+$, 345.2 [M+Na]$^+$; m/z 321.2 [M-H]$^-$ Data for minor isomer tert-butyl (S)-3-((S)-1-hydroxy-2-nitroethyl)-3,4-dihydroisoquinoline-2(1H)-carboxylate I11B:

$^1$H NMR (400 MHz, d$_4$-MeOD) δ 7.25-7.11 (m, 4H), 4.75 (d, J=16.5 Hz, 1H), 4.68-4.48 (m, 4H), 4.42-4.23 (m, overlaps with residual nitromethane), 3.06 (dd, J=16.3, 6.1 Hz, 1H), 2.91 (d, J=16.1 Hz, 1H), 1.50 (s, 9H). LCMS-B: RT 3.70 min; m/z 223.2 [M-Boc+2H]$^+$, 345.2 [M+Na]$^+$; m/z 321.2 [M-H]$^-$ (e) tert-Butyl (S)-3-((R)-1-hydroxy-2-nitroethyl)-3,4-dihydroisoquinoline-2(1H)-carboxylate (I11A)

Copper Catalyst Used:

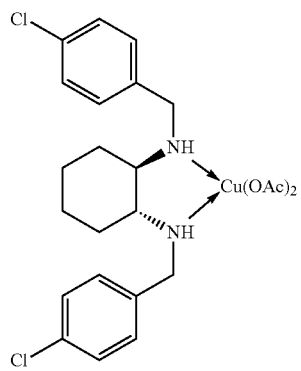

tert-Butyl (S)-3-formyl-3,4-dihydroisoquinoline-2(1H)-carboxylate (I10) (1.9 mmol @100% conversion), absolute ethanol (5 mL), nitromethane (1.02 mL, 19.0 mmol) and the copper catalyst (91 mg, 10 mol %) (see above figure, prepared according to Tetrahedron: Asymmetry (2008) 2310-2315) were stirred at room temperature. After 90 hours the mixture was concentrated in vacuo, chromatography (40 g silica cartridge, 0-15% ethyl acetate/hexanes) gave the desired compound (352 mg, 58% yield over two steps). $^1$H NMR (400 MHz, d$_4$-MeOD) δ 7.25-7.13 (m, 4H), 4.85-4.68 (m, 1H), 4.65-4.49 (m, 1H), 4.49-4.39 (m, 1H), 4.36-3.96 (m, overlaps with trace solvent), 3.19 (dd, J=15.9, 3.2 Hz, 1H), 2.92 (dd, J=15.9, 5.6 Hz, 1H), 1.51 (s, 9H). LCMS-B: RT 3.25 min; m/z 321.1 [M-H]$^-$ (f) tert-Butyl (S)-3-((R)-2-amino-1-hydroxyethyl)-3,4-dihydroisoquinoline-2(1H)-carboxylate (I12)

tert-Butyl (S)-3-((R)-1-hydroxy-2-nitroethyl)-3,4-dihydroisoquinoline-2(1H)-carboxylate (I11A) (1.54 g, 4.78 mmol), absolute ethanol (75 mL) and 10% Pd/C (53% wetted with water, 1.5 g) were stirred under hydrogen (balloon). After 3 hours the mixture was filtered through celite, the celite was washed with absolute ethanol (100 mL) and the combined filtrates concentrated in vacuo to give the desired compound (1.34 g, 96% yield) as a pale grey-green syrup. LCMS-B: RT 3.27 min, m/z 293.2 [M+H]$^+$ Alternate Synthesis Method (a) (S)-2-(tert-Butoxycarbonyl)-1,2,3,4-tetrahydroisoquinoline-3-carboxylic acid (I8)

(S)-1,2,3,4-Tetrahydroisoquinoline-3-carboxylic acid (50.0 g, 282 mmol) was vigorously stirred in a mixture of 1,4-dioxane (1000 mL) and water (500 mL). Sodium bicarbonate (47.4 g, 564 mmol) and Boc anhydride (67.7 g, 310 mmol) were added and the reaction was stirred vigorously at room temperature for 6 days. The mixture was concentrated in vacuo and the residue dissolved in water (2000 mL). A 30% w/v aqueous solution of sodium hydrogen sulfate monohydrate (300 mL) was added and the mixture extracted with chloroform (3×1000 mL). The pooled organic extracts were washed with brine, dried over sodium sulfate and concentrated in vacuo to give the desired compound (90.0 g, quantitative) as a thick syrup. LCMS-B: RT 3.64 min; m/z 178.1 [M–Boc+2H]$^+$; m/z 276.1 [M–H]$^-$ (b) tert-Butyl (S)-3-(hydroxymethyl)-3,4-dihydroisoquinoline-2(1H)-carboxylate (I9)

(S)-2-(tert-Butoxycarbonyl)-1,2,3,4-tetrahydroisoquinoline-3-carboxylic acid (I8) (54.0 g, 195 mmol) was dissolved in THF (1000 mL) and CDI (63.2 g, 390 mmol) was added. The mixture was stirred for 2 hours at 30° C. then cooled to 0° C. A solution of sodium borohydride (14.7 g, 390 mmol) in water (120 mL) was added dropwise. After 3 hours the mixture was quenched with acetone (300 mL) and concentrated in vacuo. The residue was partitioned between water (1000 mL) and ethyl acetate (1000 mL). The separated aqueous phase was extracted with ethyl acetate (4×500 mL) and the combined organic extracts washed with 5% w/v aqueous NaHSO$_4$ (1000 mL), brine (500 mL), dried over sodium sulfate and concentrated in vacuo. The residue was purified by chromatography (5-20% ethyl acetate/petroleum ether) to give the desired compound (30.4 g, 59% yield) as a yellow syrup. $^1$H NMR (400 MHz, CDCl$_3$) δ 7.25-7.06 (m, 4H), 4.82-4.59 (m, 1H), 4.57-4.38 (m, 1H), 4.37-4.19 (m, 1H), 3.57-3.40 (m, overlaps with trace solvent), 3.03 (dd, J=16.1, 5.7 Hz, 1H), 2.80 (d, J=16.1 Hz, 1H), 1.50 (s, 9H). LCMS-B: RT 3.66 min; m/z 164.2 [M–Boc+2H]$^+$, 286.2 [M+Na]$^+$ (c) tert-Butyl (S)-3-formyl-3,4-dihydroisoquinoline-2(1H)-carboxylate (I10)

tert-Butyl (S)-3-(hydroxymethyl)-3,4-dihydroisoquinoline-2(1H)-carboxylate (I9) (16 g, 0.06 mol), DCM (250 mL) and DMSO (75 mL) were cooled to 0° C. Triethylamine (25.1 mL, 0.18 mol) was added, followed by pyridine-sulfur trioxide complex (28.6 g, 0.18 mol). The mixture was stirred at 0° C. for 30 minutes then allowed to come to room temperature and stirred at room temperature overnight. Saturated sodium bicarbonate (200 mL) and water (200 mL) were added, and the mixture extracted with diethyl ether (3×300 mL). The pooled ether extracts were washed with 1:1 water:saturated aqueous NH$_4$Cl (200 mL), dried over sodium sulfate and concentrated in vacuo to give the desired compound (16.0 g) as an orange oil which was used without further purification.

(e) tert-Butyl (S)-3-((R)-1-hydroxy-2-nitroethyl)-3,4-dihydroisoquinoline-2(1H)-carboxylate (I11A)

To a solution of tert-butyl (S)-3-formyl-3,4-dihydroisoquinoline-2(1H)-carboxylate (I10) (0.06 mol @100% conversion) in absolute ethanol (50 mL) was added a solution of the copper catalyst (6.8 g, 20 mol %) (see above figure, prepared according to Tetrahedron: Asymmetry (2008) 2310-2315) in absolute ethanol (10 mL). The mixture was cooled to 0° C. and nitromethane (36.0 g, 0.6 mol) was added. The reaction was stirred at 0° C. for 3 days, the mixture was concentrated in vacuo and purified by chromatography (5% ethyl acetate/petroleum ether) to give the desired compound (7.5 g, 39% yield over two steps). $^1$H NMR (400 MHz, d$_4$-MeOD) δ 7.25-7.13 (m, 4H), 4.85-4.68 (m, 1H), 4.65-4.49 (m, 1H), 4.49-4.39 (m, 1H), 4.36-3.96 (m, overlaps with trace solvent), 3.19 (dd, J=15.9, 3.2 Hz, 1H), 2.92 (dd, J=15.9, 5.6 Hz, 1H), 1.51 (s, 9H). LCMS-B: RT 3.25 min; m/z 321.1 [M–H]$^-$ (f) tert-Butyl (S)-3-((R)-2-amino-1-hydroxyethyl)-3,4-dihydroisoquinoline-2(1H)-carboxylate (I12)

To a solution of tert-butyl (S)-3-((R)-1-hydroxy-2-nitroethyl)-3,4-dihydroisoquinoline-2(1H)-carboxylate (I11A) (7.5 g, 23.3 mmol) in absolute ethanol (100 mL) was added 10% Pd/C (7.5 g) and the reaction was stirred under an atmosphere of hydrogen. After 3 hours, the mixture was filtered through Celite, the Celite was washed with absolute ethanol (200 mL) and the combined filtrates concentrated in vacuo to give the desired compound (5.3 g, 78% yield) as a pale grey solid. LCMS-B: RT 3.27 min, m/z 293.2 [M+H]$^+$ Example 1

4-(3-Oxa-8-azabicyclo[3.2.1]octane-8-carbonyl)-2-ethoxy-N—((R)-2-hydroxy-2-((S)-7-methoxy-1,2,3,4-tetrahydroisoquinolin-3-yl)ethyl)benzamide (1)

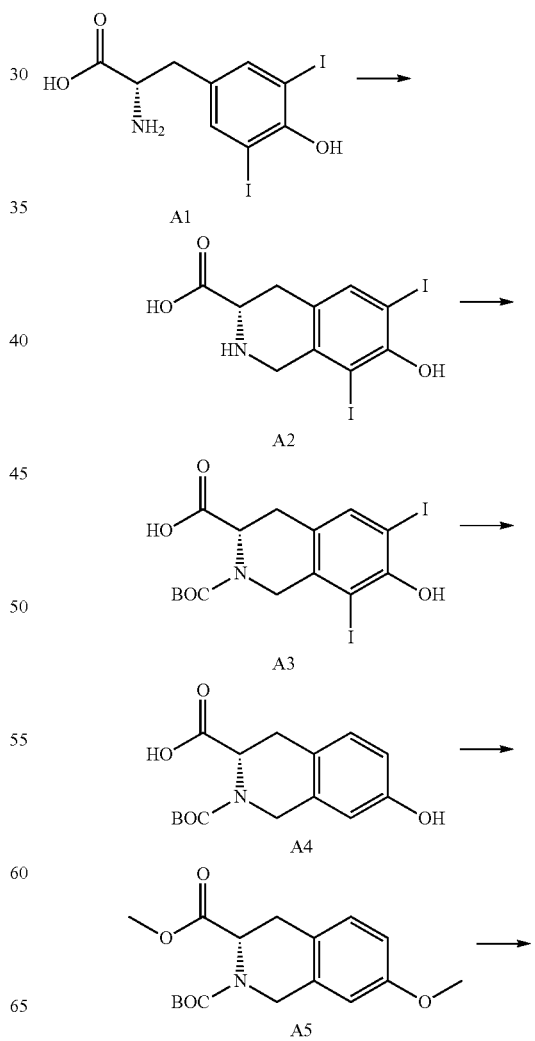

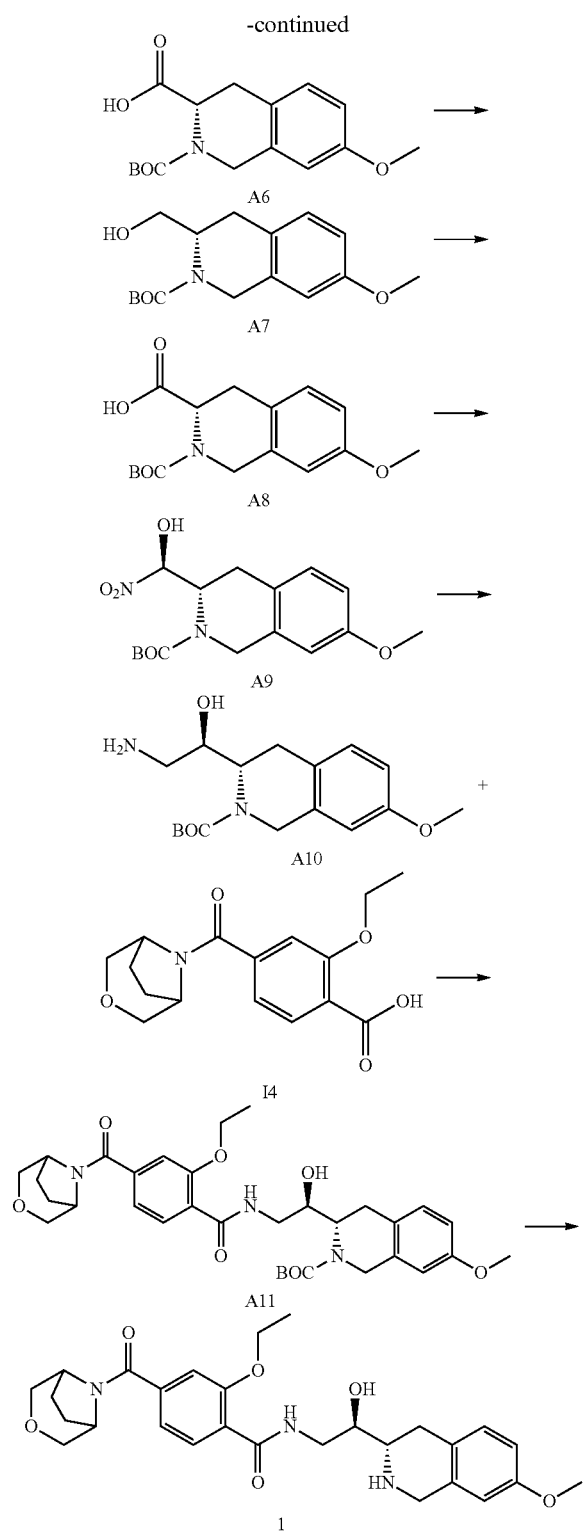

(a) (S)-7-Hydroxy-6,8-diiodo-1,2,3,4-tetrahydroisoquinoline-3-carboxylic acid A2

To a solution of (S)-2-amino-3-(4-hydroxy-3,5-diiodophenyl)propanoic acid A1 (3.0 g, 6.9 mmol) in concentrated aqueous HCl (25 mL) was added 1,2-dimethoxyethane (2 mL) and paraformaldehyde (0.78 g, 26 mmol). The mixture was stirred vigorously and slowly heated to 72° C. After 30 min, further concentrated aqueous HCl (5 mL), 1,2-dimethoxyethane (1 mL) and paraformaldehyde (0.52 g, 17.3 mmol) were added and heating continued at 72° C. for 18 h. The suspension was then cooled in an ice bath and the solids collected by filtration, washed thoroughly with 1,2-dimethoxyethane and dried under vacuum to give the title compound as a brown solid (1.7 g, 57%. LCMS: RT 2.45 min; m/z 466.8 [M+Na]$^+$.

(b) (S)-2-(tert-Butoxycarbonyl)-7-hydroxy-6,8-diiodo-1,2,3,4-tetrahydroisoquinoline-3-carboxylic acid A3

To a solution of (S)-7-hydroxy-6,8-diiodo-1,2,3,4-tetrahydroisoquinoline-3-carboxylic acid A2 (1.7 g, 3.8 mmol) in 1 M aqueous NaOH (10 mL) was added a solution of (Boc)$_2$O (917.1 mg, 4.2 mmol) in THF (2 mL). The solution was kept between pH 9 and 11 by addition of 1 M aqueous NaOH solution. The resulting mixture was stirred at room temperature for 6 hours. The solvent was removed and the residue taken up in water. The pH of the solution was adjusted to 4-5 by addition of 30% w/v aqueous NaHSO$_4$. The aqueous phase was extracted with EtOAc (3×10 mL) and the combined organic fractions were washed with brine (2×10 mL), dried (Na$_2$SO$_4$) and concentrated to give the title compound as a brown solid (1.61 g, 77%). LCMS: RT 2.93 min; m/z 567.9 [M+Na]$^+$.

(c) (S)-2-(tert-Butoxycarbonyl)-7-hydroxy-1,2,3,4-tetrahydroisoquinoline-3-carboxylic acid A4

A mixture of (S)-2-(tert-butoxycarbonyl)-7-hydroxy-6,8-diiodo-1,2,3,4-tetrahydroisoquinoline-3-carboxylic acid A3 (500 mg, 0.92 mmol), triethylamine (204.3 mg, 2.02 mmol) and Pd/C (50 mg, 10%) in methanol (6 mL) was stirred at room temperature under a hydrogen atmosphere for 24 hours. The reaction mixture was filtered through Celite and the filtrate concentrated. The crude product was resubjected to the same conditions above for a further 24 h, then filtered through Celite and concentrated. The residue obtained was diluted with water and acidified to pH 4-5 with 1 M aqueous HCl, then extracted with EtOAc (2×10 mL). The combined organic fractions were washed with brine (10 mL), dried (Na$_2$SO$_4$) and concentrated to give the title compound as a brown oil (310.7 mg, 100%). LCMS: RT 2.48 min; m/z 316.1 [M+Na]$^+$.

(d) (S)-2-tert-Butyl 3-methyl 7-methoxy-3,4-dihydroisoquinoline-2,3(1H)-dicarboxylate A5

To a solution of (S)-2-(tert-butoxycarbonyl)-7-hydroxy-1,2,3,4-tetrahydroisoquinoline-3-carboxylic acid A4 (300 mg, 1.02 mmol) in dimethyl sulfoxide (6 mL) was added K$_2$CO$_3$ (424.4 mg, 3.07 mmol) and iodomethane (435.7 mg, 3.07 mmol). The resulting mixture was stirred at room temperature overnight. The reaction was quenched by addition of saturated aqueous NaHCO$_3$ (5 mL) and the aqueous layer extracted with EtOAc (2×8 mL). The combined organic fractions were washed with brine (2×8 mL), dried (Na$_2$SO$_4$), filtered and concentrated. The residue obtained was purified by column chromatography (6% EtOAc/petroleum ether) to give the title compound as a yellow oil (140 mg, 43%). LCMS: RT 2.87 min; m/z 344.1 [M+Na]$^+$.

(e) (S)-2-(tert-Butoxycarbonyl)-7-methoxy-1,2,3,4-tetrahydroisoquinoline-3-carboxylic acid A6

To a solution of (S)-2-tert-butyl 3-methyl 7-methoxy-3,4-dihydroisoquinoline-2,3(1H)-dicarboxylate A5 (130 mg, 0.4 mmol) in a mixture of THF (5 mL), methanol (0.5 mL) and H$_2$O (0.5 mL) was added LiOH.H$_2$O (85 mg, 2.02 mmol). The resulting mixture was stirred at room temperature overnight then concentrated. The residue obtained was diluted with water (4 mL) and adjusted to pH 3-4 by addition of 2M HCl. The aqueous phase was extracted with EtOAc (3×5 mL) and the combined organic layers washed with brine (2×5 mL), dried (Na$_2$SO$_4$), filtered and concentrated to give the title compound as a pale yellow oil (250 mg, 100%). LCMS: RT 2.68 min; m/z 330.1 [M+Na]$^+$.

(f) (S)-tert-Butyl 3-(hydroxymethyl)-7-methoxy-3,4-dihydroisoquinoline-2(1H)-carboxylate A7

To a solution of (S)-2-(tert-butoxycarbonyl)-7-methoxy-1,2,3,4-tetrahydroisoquinoline-3-carboxylic acid A6 (250 mg, 0.81 mmol) in THF (4 mL) was added CDI (265.5 mg, 1.6 mmol). The mixture was stirred at room temperature for 2 hours, then cooled to 0° C. A solution of NaBH$_4$ (61.5 mg, 1.6 mmol) in water (1 mL) was added dropwise and the resulting mixture stirred at room temperature for 3 hours. The solvent was removed in vacuo and the residue obtained was partitioned between water (4 mL) and EtOAc (5 mL). The aqueous layer was extracted with EtOAc (3×8 mL) and the combined organic fractions washed with saturated aqueous NaHSO$_4$ (2×8 mL) and brine (2×8 mL), dried (Na$_2$SO$_4$) and concentrated. The residue was purified by preparative TLC (25% EtOAc/petroleum ether) to give the title compound as a pale yellow oil (128.2 mg, 54%). LCMS: RT 2.67 min; m/z 316.2 [M+Na]$^+$.

(g) (S)-tert-Butyl 3-formyl-7-methoxy-3,4-dihydroisoquinoline-2(1H)-carboxylate A8

To a solution of (S)-tert-butyl 3-(hydroxymethyl)-7-methoxy-3,4-dihydroisoquinoline-2(1H)-carboxylate A7 (170 mg, 0.55 mmol) in a mixture of DCM (6 mL) and DMSO (1 mL) at 0° C. was added Et$_3$N (184.9 mg, 1.83 mmol) and pyridine sulfur trioxide (290.8 mg, 1.83 mmol). The reaction was stirred at room temperature for 3 hours then quenched by addition of saturated aqueous NaHCO$_3$ (70 mL) and water (30 mL). The aqueous layer was extracted with diethyl ether (3×70 mL) and the pooled ether extracts were washed with 0.5 N aqueous HCl solution (30 mL) and brine (20 mL), dried (Na$_2$SO$_4$), filtered and concentrated to give the title compound as a yellow oil (189.9 mg, 100%). LCMS: RT 2.71 min; no molecular mass ion detected (h) (S)-tert-Butyl 3-((R)-1-hydroxy-2-nitroethyl)-7-methoxy-3,4-dihydroisoquinoline-2(1H)-carboxylate A9

A mixture of (1R,2R)-N1,N2-bis(4-chlorobenzyl)cyclohexane-1,2-diamine (26.4 mg, 0.073 mmol) and cupric acetate monohydrate (12.1 mg, 0.061 mmol) in ethanol (2 mL) was stirred at room temperature for 0.5 hours. Then a solution of (S)-tert-butyl 3-formyl-7-methoxy-3,4-dihydroisoquinoline-2(1H)-carboxylate A8 (185 mg, 0.61 mmol) in ethanol (2 mL) was added. The reaction mixture was cooled to 0° C., stirred for a further 0.5 hours then CH$_3$NO$_2$ (364.3 mg, 6.06 mmol) was added. The reaction was allowed to warm to room temperature and stirred 24 hrs. The mixture was concentrated and the residue obtained purified by preparative TLC (20% EtOAc/Petroleum ether) to give the title compound as an off-white solid (43 mg, 19%). LCMS: RT 2.70 min; m/z 375.1 [M+Na]$^+$.

(i) (S)-tert-Butyl 3-((R)-2-amino-1-hydroxyethyl)-7-methoxy-3,4-dihydroisoquinoline-2(1H)-carboxylate A10

A mixture of (S)-tert-butyl 3-((R)-1-hydroxy-2-nitroethyl)-7-methoxy-3,4-dihydroisoquinoline-2(1H)-carboxylate A9 (40 mg, 0.11 mg) and 10% Pd/C (48 mg) in ethanol (4 mL) was stirred at room temperature overnight under an atmosphere of H$_2$. The catalyst was removed by filtration through celite and the filtrate concentrated. The residue obtained was purified by preparative TLC (50% EtOAc/petroleum ether) to give the title compound as an off-white solid (16 mg, 44%). LCMS: RT 2.32 min; m/z 323.2 [M+H]$^+$.

(j) (3S)-tert-Butyl 3-((1R)-2-(4-(3-oxa-8-azabicyclo[3.2.1]octane-8-carbonyl)-2-ethoxybenzamido)-1-hydroxyethyl)-7-methoxy-3,4-dihydroisoquinoline-2(1H)-carboxylate A11

To a solution of (S)-tert-butyl 3-((R)-2-amino-1-hydroxyethyl)-7-methoxy-3,4-dihydroisoquinoline-2(1H)-carboxylate A10 (16 mg, 0.05 mmol) and 4-(3-oxa-8-azabicyclo[3.2.1]octane-8-carbonyl)-2-ethoxybenzoic acid I4 (16.7 mg, 0.055 mmol) in DCM (2.5 mL) was added, HOBt (0.67 mg, 0.005 mmol), DIEA (25.6 mg, 0.199 mmol) and EDCI (19.1 mg, 0.099 mmol). The resulting mixture was stirred at room temperature overnight then partitioned between saturated aqueous NaHCO$_3$ (5 mL) and CH$_2$Cl$_2$ (5 mL). The aqueous layer was extracted with CH$_2$Cl$_2$ (2×5 mL) and the combined organic fractions washed with brine (2×8 mL), dried (Na$_2$SO$_4$) and concentrated. The residue obtained was purified by preparative TLC (40% petroleum ether/EtOAc) to give the title compound (13 mg, 43%) as a white solid. LCMS: RT 2.86 min; m/z 632.3 [M+Na]$^+$, 610.4 [M+H]$^+$.

(k) 4-(3-Oxa-8-azabicyclo[3.2.1]octane-8-carbonyl)-2-ethoxy-N—((R)-2-hydroxy-2-((S)-7-methoxy-1,2,3,4-tetrahydroisoquinolin-3-yl)ethyl)benzamide 1

A solution of (3S)-tert-butyl 3-((1R)-2-(4-(3-oxa-8-azabicyclo[3.2.1]octane-8-carbonyl)-2-ethoxybenzamido)-1-hydroxyethyl)-7-methoxy-3,4-dihydroisoquinoline-2(1H)-carboxylate A11 (13 mg, 0.021 mmol) in HCl/Et$_2$O (1.8 M, 2 mL) was stirred at room temperature overnight. The reaction mixture was concentrated and washed with Et$_2$O (3 mL). The residue obtained was suspended in water (2 mL) and freeze-dried to give the title compound (8 mg, 69%) as an off-white solid. $^1$H NMR (400 MHz, CD$_3$OD) δ 7.98-7.96 (d, J=8.0 Hz, 1H), 7.22-7.15 (m, 3H), 6.90-6.88 (m, 1H), 6.79 (s, 1H), 4.65 (s, 1H), 4.44 (q, J=7.2 Hz, 2H), 4.27-4.22 (m, 3H), 3.95 (s, 1H), 3.78 (s, 3H), 3.73-3.68(m, 3H), 3.63-3.60 (m, 3H), 3.24-3.08 (m, 3H), 2.07-2.00 (m, 4H), 1.43 (t, J=7.2 Hz, 3H). LCMS: RT 2.01 min; m/z 510.3 [M+H]$^+$.

Example 2

4-(3-Oxa-8-azabicyclo[3.2.1]octane-8-carbonyl)-N—((R)-2-hydroxy-2-((S)-7-methoxy-1,2,3,4-tetrahydroisoquinolin-3-yl)ethyl)benzamide (2)

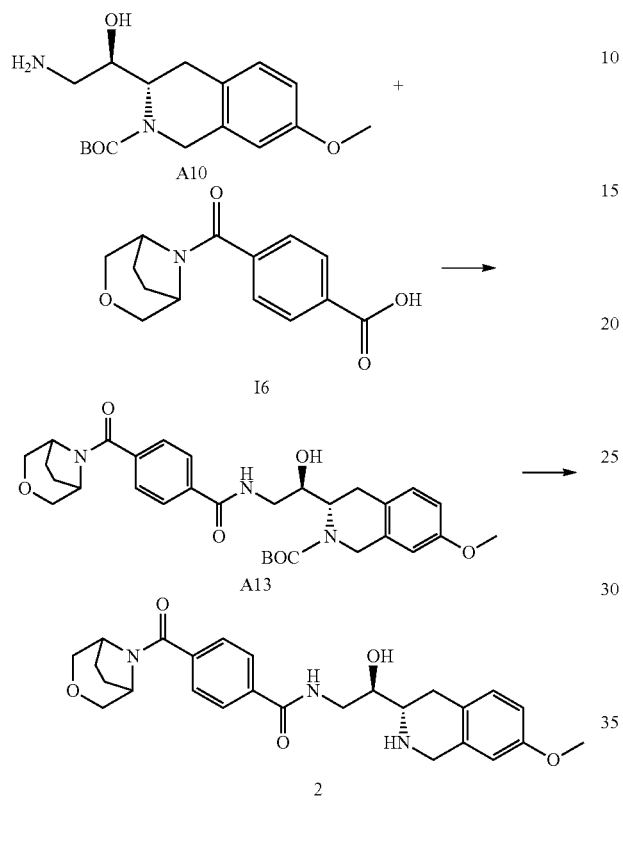

(a) (3S)-tert-Butyl 3-((1R)-2-(4-(3-oxa-8-azabicyclo [3.2.1]octane-8-carbonyl)benzamido)-1-hydroxyethyl)-7-methoxy-3,4-dihydroisoquinoline-2(1H)-carboxylate A13

To a solution of (S)-tert-butyl 3-((R)-2-amino-1-hydroxyethyl)-7-methoxy-3,4-dihydroisoquinoline-2(1H)-carboxylate A10 (45 mg, 0.14 mmol) and 4-(3-oxa-8-azabicyclo [3.2.1]octane-8-carbonyl)benzoic acid I6 (40.1 mg, 0.15 mmol) in DCM (5 mL) was added HOBt (1.89 mg, 0.014 mmol), DIEA (72 mg, 0.56 mmol) and EDCI (53.5 mg, 0.28 mmol). The resulting mixture was stirred at room temperature overnight then partitioned between DCM (5 mL) and saturated aqueous NaHCO₃ (5 mL). The aqueous layer was extracted with CH₂Cl₂ (2×8 mL) and the combined organic fractions were washed with brine (2×8 mL), dried (Na₂SO₄) and concentrated. The residue obtained was purified by preparative TLC (3% methanol/CH₂Cl₂) to give the title compound as an off-white solid (28.2 mg, 36%). LCMS: RT 2.75 min; m/z 588.3 [M+Na]⁺.

(b) 4-(3-Oxa-8-azabicyclo[3.2.1]octane-8-carbonyl)-N—((R)-2-hydroxy-2-((S)-7-methoxy-1,2,3,4-tetrahydroisoquinolin-3-yl)ethyl)benzamide 2

A solution of (3S)-tert-butyl 3-((1R)-2-(4-(3-oxa-8-azabicyclo[3.2.1]octane-8-carbonyl) benzamido)-1-hydroxyethyl)-7-methoxy-3,4-dihydroisoquinoline-2(1H)-carboxylate A13 (25 mg, 0.044 mmol) in HCl/Et₂O (2 M, 6 mL) was stirred at room temperature for 6 hours. The reaction mixture was concentrated and washed with Et₂O (3 mL). The residue obtained was taken up in water (3 mL) and freeze-dried to give the title compound as an off-white solid (12 mg, 58%). ¹H NMR (400 MHz, CD₃OD) δ 7.96 (d, J=6.8 Hz, 2H), 7.60 (d, J=6.8 Hz, 2H), 7.20 (d, J=8.4 Hz, 1H), 6.89 (d, J=8.0 Hz, 1H), 6.78 (s, 1H), 4.65 (br s, 1H), 4.46-4.42(m, 1H), 4.35-4.27 (m, 2H), 3.94 (s, 1H), 3.83-3.78 (m, 1H), 3.77 (s, 3H), 3.73-3.68 (m, 2H), 3.63-3.59 (m, 4H), 3.26-3.12 (m, 2H), 2.07-2.00 (m, 4H); LCMS: RT 3.2 min; m/z 466.2 [M+H]⁺.

Example 3

4-(3-Oxa-8-azabicyclo[3.2.1]octane-8-carbonyl)-2-ethoxy-N—((R)-2-hydroxy-2-((S)-2-methyl-1,2,3,4-tetrahydroisoquinolin-3-yl)ethyl)benzamide 2,2,2-trifluoroacetate (3)

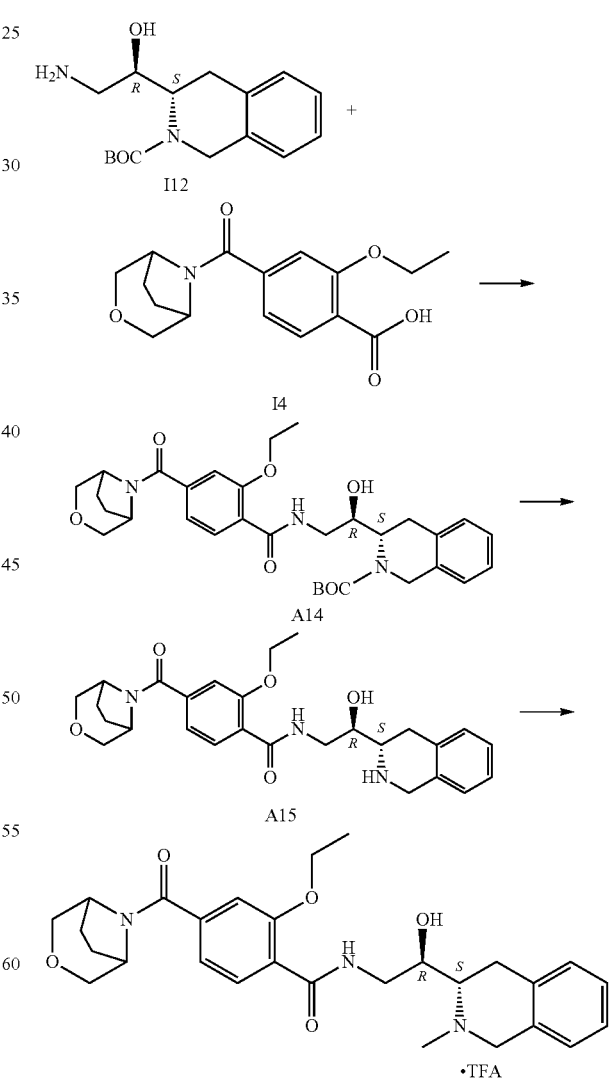

(a) tert-Butyl (3S)-3-((1R)-2-(4-(3-oxa-8-azabicyclo[3.2.1]octane-8-carbonyl)-2-ethoxybenzamido)-1-hydroxyethyl)-3,4-dihydroisoquinoline-2(1H)-carboxylate A14

To a mixture of tert-butyl (S)-3-((R)-2-amino-1-hydroxyethyl)-3,4-dihydroisoquinoline-2(1H)-carboxylate I12 (2.7 g, 9.2 mmol), 4-(3-oxa-8-azabicyclo[3.2.1]octane-8-carbonyl)-2-ethoxybenzoic acid I4 (3.1 g, 10.2 mmol), HOBt (0.13 g, 0.9 mmol) and DIPEA (4.8 g, 36.9 mmol) in dichloromethane (40 mL) was added EDCI.HCl (3.6 g, 18.5 mmol). The resulting mixture stirred overnight at room temperature. The mixture was washed with saturated sodium bicarbonate (20 mL) and the aqueous layer extracted with dichloromethane (2×15 mL). The combined organic extracts were washed with brine, dried over sodium sulfate, filtered and concentrated. The residue was purified by column chromatography (50% ethyl acetate/petroleum ether) to give the title compound (2.9 g, 55%) as an off-white solid. LCMS-C: RT 2.86 min, m/z 580.4 [M+H]$^+$ (b) 4-(3-Oxa-8-azabicyclo[3.2.1]octane-8-carbonyl)-2-ethoxy-N—((R)-2-hydroxy-2-((S)-1,2,3,4-tetrahydroisoquinolin-3-yl)ethyl)benzamide hydrochloride A15 tert-Butyl (3S)-3-((1R)-2-(4-(3-oxa-8-azabicyclo[3.2.1]octane-8-carbonyl)-2-ethoxy-benzamido)-1-hydroxyethyl)-3,4-dihydroisoquinoline-2(1H)-carboxylate A14 (3.74 g, 6.46 mmol) was dissolved in diethyl ether (40 mL), stirred vigorously, and HCl in diethyl ether (1.0M, 55 mL) was added. The reaction was stirred at ambient temperature for 18 hours before another addition of HCl in diethyl ether (1.0M, 90 mL). The reaction was stirred at ambient temperature for 6 hours and the solvent removed in vacuo to give a white solid (3.7 g). The flask was cooled in an ice-water bath and a 2 M aqueous NaOH solution (150 mL, 300 mmol) was added followed by EtOAc (100 mL). The flask was vigorously stirred for 1 hour until the solid had dissolved. The layers were separated and the aqueous layer was extracted with EtOAc (2×100 mL). The combined organic extracts were washed with water (100 mL), brine (100 mL), then dried over Na$_2$SO$_4$, filtered and concentrated in vacuo to give the title compound (2.92 g, 94% yield) as a foamy white solid. $^1$H NMR (400 MHz, CH$_3$OD) δ 8.02 (d, J=7.91 Hz, 1H), 7.24-6.97 (m, 6H), 4.64 (s, 1H), 4.25 (q, J=6.95 Hz, 2H), 4.04-3.93 (m, 3H), 3.91-3.66 (m, 5H), 3.62-3.51 (m, 2H), 3.04-2.76 (m, 3H), 2.11-1.94 (m, obscured by solvent), 1.48 (t, J=6.96 Hz, 3H).

(c) 4-(3-Oxa-8-azabicyclo[3.2.1]octane-8-carbonyl)-2-ethoxy-N—((R)-2-hydroxy-2-((S)-2-methyl-1,2,3,4-tetrahydroisoquinolin-3-yl)ethyl)benzamide 2,2,2-trifluoroacetate (3)

Sodium triacetoxyborohydride (104 mg, 0.491 mmol, 4.7 equiv) was added to a solution of 4-(3-oxa-8-azabicyclo[3.2.1]octane-8-carbonyl)-2-ethoxy-N—((R)-2-hydroxy-2-((S)-1,2,3,4-tetrahydroisoquinolin-3-yl)ethyl)benzamide A15 (free base, 50 mg, 0.10 mmol, 1 equiv), aqueous 37% (weight) formaldehyde solution (31 μL, 0.42 mmol, 4 equiv) and glacial acetic acid (2 drops) in methanol (20 mL). The reaction was stirred at 50° C. for 19 hours. The solvent was removed in vacuo and a saturated aqueous solution of sodium hydrogen carbonate was added. The aqueous mixture was extracted with EtOAc (×3) and the combined organic phases washed with water, brine, dried over MgSO$_4$, filtered and the solvent removed in vacuo to give a colourless oil. The oil was purified by column chromatography (12 g SiO$_2$ cartridge, 0-10% MeOH in EtOAc (modified by the addition of 0.1% v/v 7 M methanolic ammonia)) to give the crude material as an off-white oil. A small amount (50 mg) of the crude material was purified by preparative LCMS (method A) to give the title compound as a colourless, glass-like solid (3.2 mg, 5% yield). $^1$H NMR (400 MHz, MeOD) δ 7.99 (d, J=7.9 Hz, 1H), 7.38-7.25 (m, 3H), 7.26-7.11 (m, 3H), 4.76-4.61 (m, 1H), 4.57-4.45 (m, 3H), 4.25 (q, J=7.0 Hz, 2H), 4.01-3.52 (m, 9H), 3.49-3.24 (m, 1H), 3.10 (s, 3H), 2.16-1.88 (m, 4H), 1.44 (t, J=7.0 Hz, 3H). LCMS-B: RT 2.90 min, m/z=494.3 [M+H]$^+$.

Further General Schemes

Scheme I:

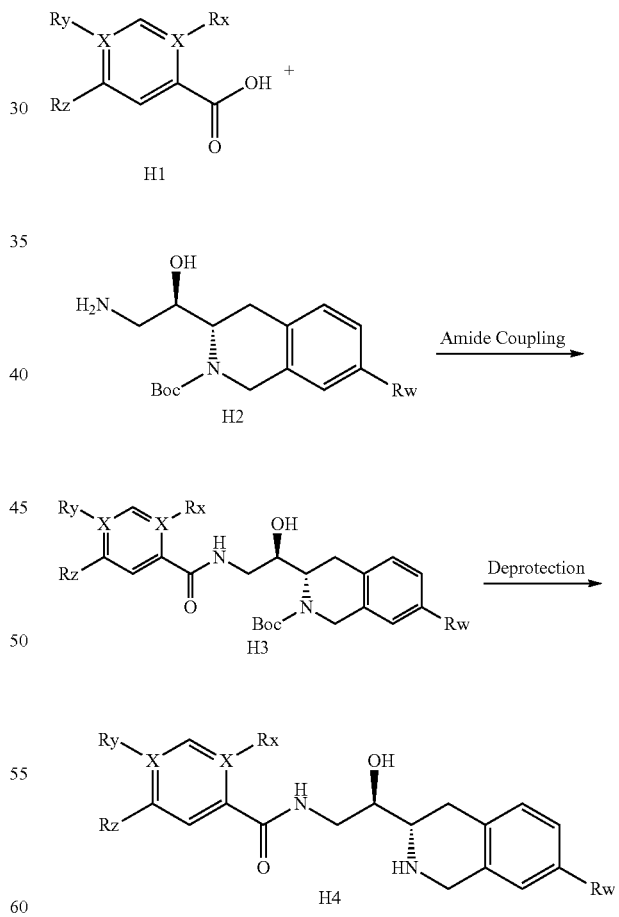

Compounds of formula H4 can be formed via a two-step sequence. An amide coupling between carboxylic acid H1 and amino alcohol H2 affords compounds with general formula H3. Deprotection affords compounds with general formula H4.

Scheme II:

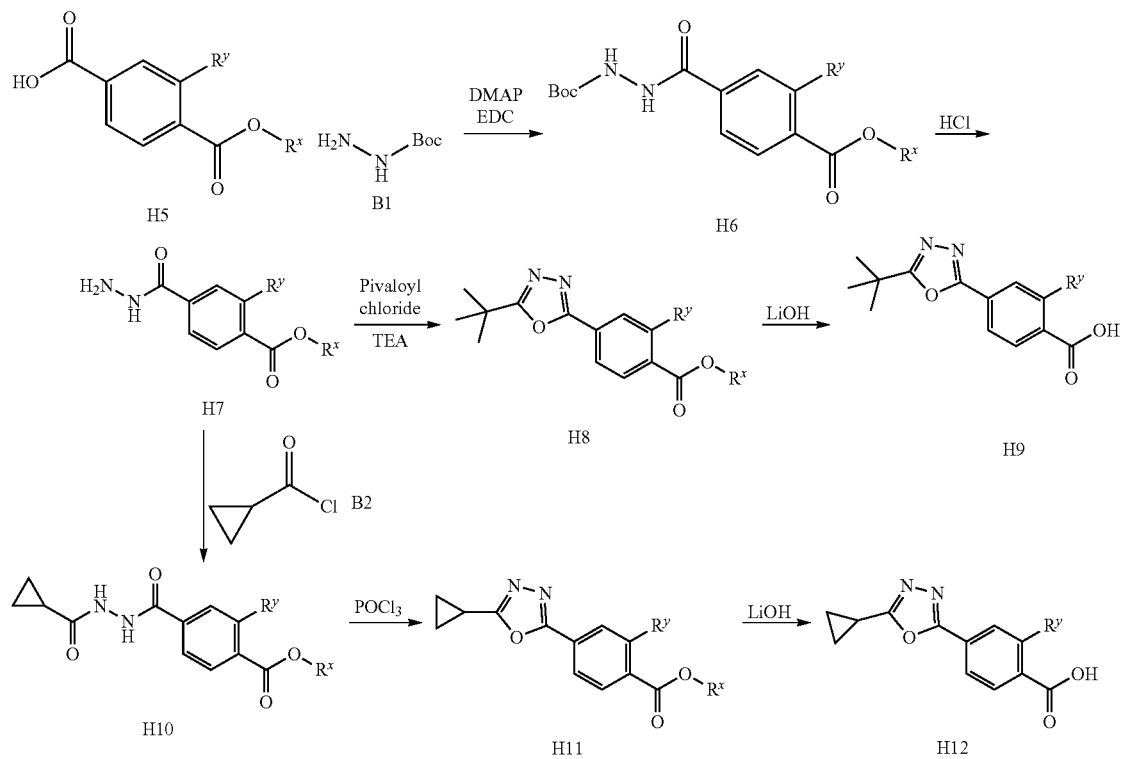

Compound H9 can be formed in the following sequence. An amide coupling between carboxylic acid H5 and hydrazine B1 affords hydrazide H6. Deprotection affords hydrazide H7, which can be used to make multiple intermediates. Reaction with pivaloyl chloride affords oxadiazole H8, while ester hydrolysis affords carboxylic acid H9. Compound H12 can be prepared from H7 as follows. Reacting hydrazide H7 with acid chloride B2 affords cyclopropyl hydrazide H10. Reaction with POCl$_3$ affords oxadiazole H11, while ester hydrolysis affords carboxylic acid H12.

Scheme III:

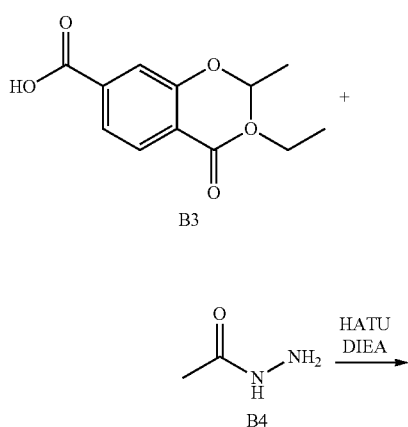

-continued

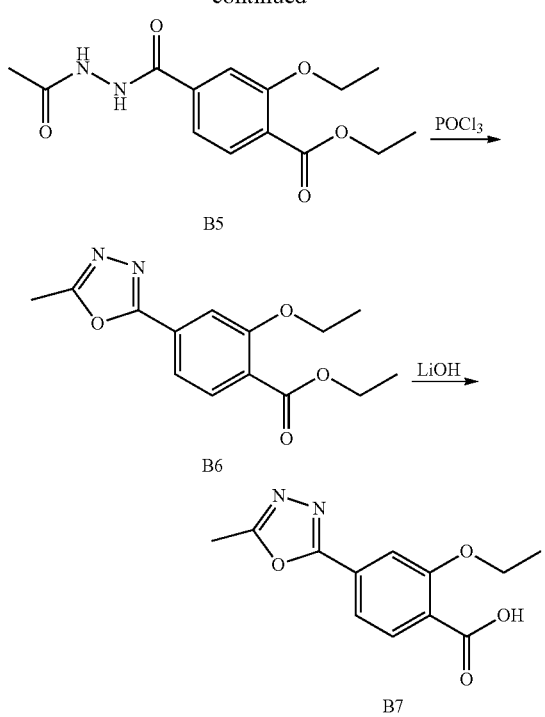

Compound B7 can be prepared from carboxylic acid B3 via an amide coupling with hydrazide B4. Ring closure with POCl$_3$ affords oxadiazole B6, which ester hydrolysis affords carboxylic acid B7.

Scheme IV:

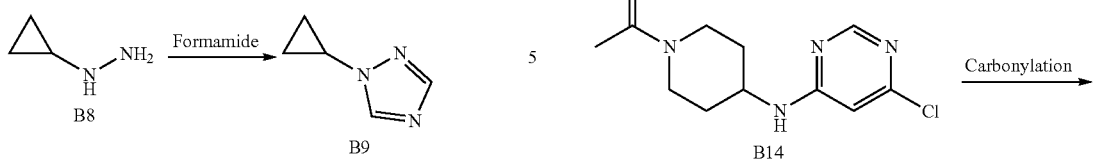

Triazole B9 can be formed in one step from hydrazine B8 and formamide.

Scheme V:

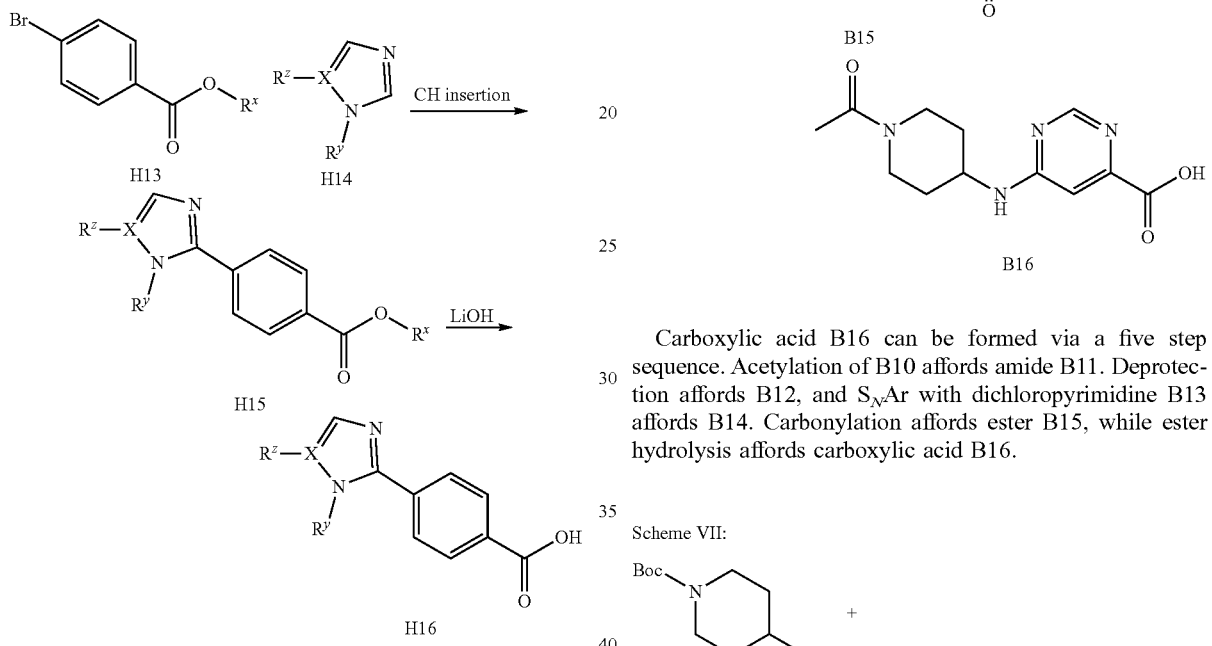

Compounds of formula H16 can be prepared via a two-step sequence. CH insertion between aryl bromide H13 and heterocycle H14 affords ester H15. Ester hydrolysis affords carboxylic acid H16.

Scheme VI:

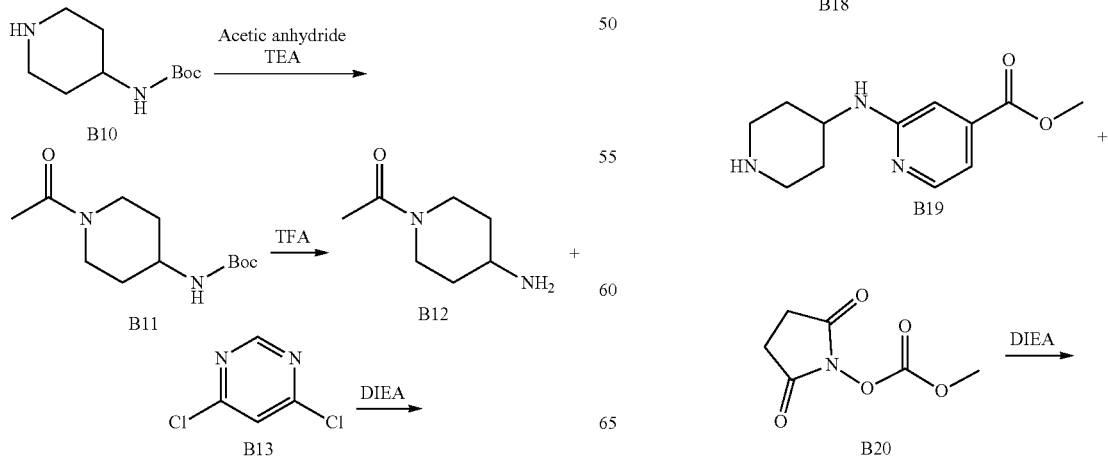

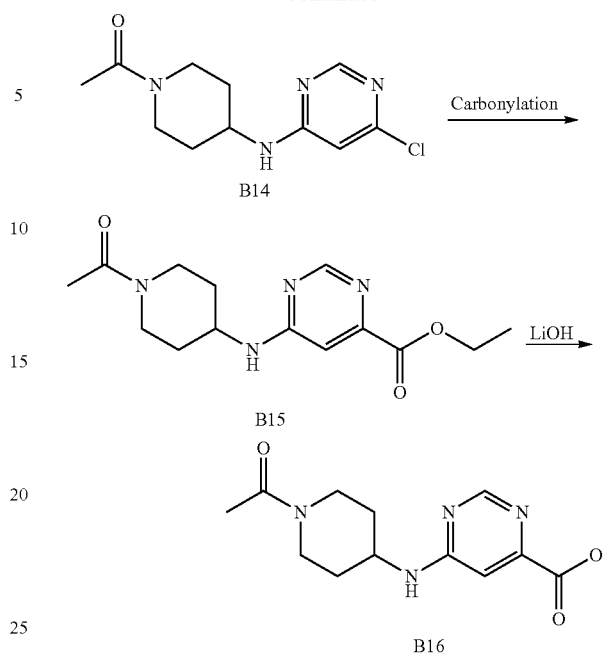

Carboxylic acid B16 can be formed via a five step sequence. Acetylation of B10 affords amide B11. Deprotection affords B12, and S$_N$Ar with dichloropyrimidine B13 affords B14. Carbonylation affords ester B15, while ester hydrolysis affords carboxylic acid B16.

Scheme VII:

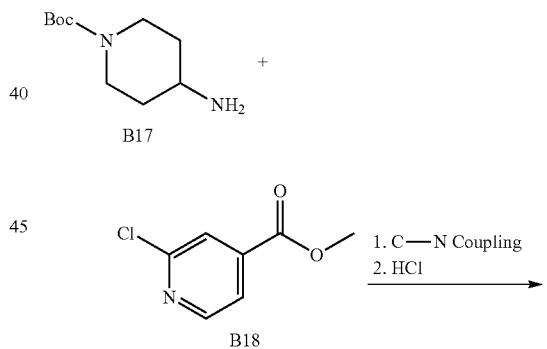

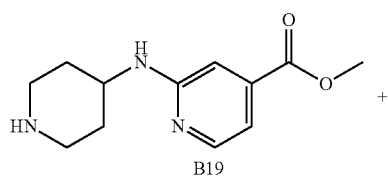

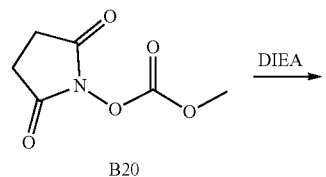

-continued

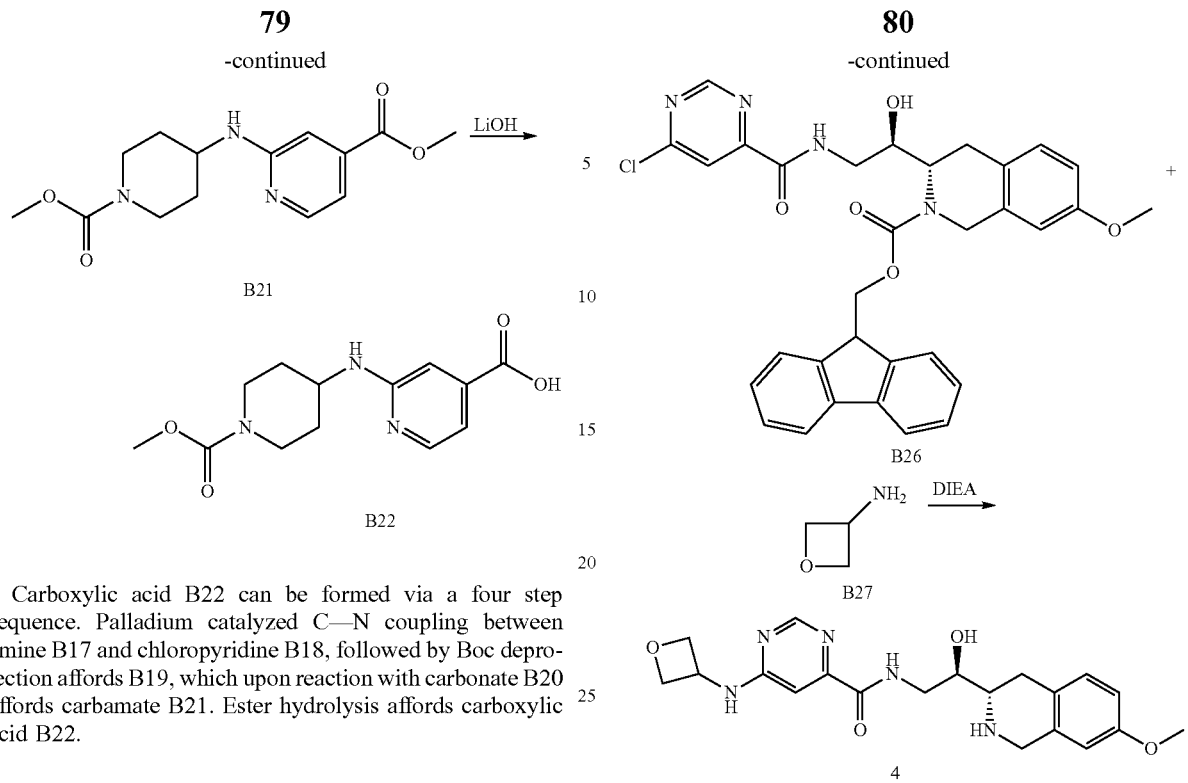

Carboxylic acid B22 can be formed via a four step sequence. Palladium catalyzed C—N coupling between amine B17 and chloropyridine B18, followed by Boc deprotection affords B19, which upon reaction with carbonate B20 affords carbamate B21. Ester hydrolysis affords carboxylic acid B22.

Scheme VIII

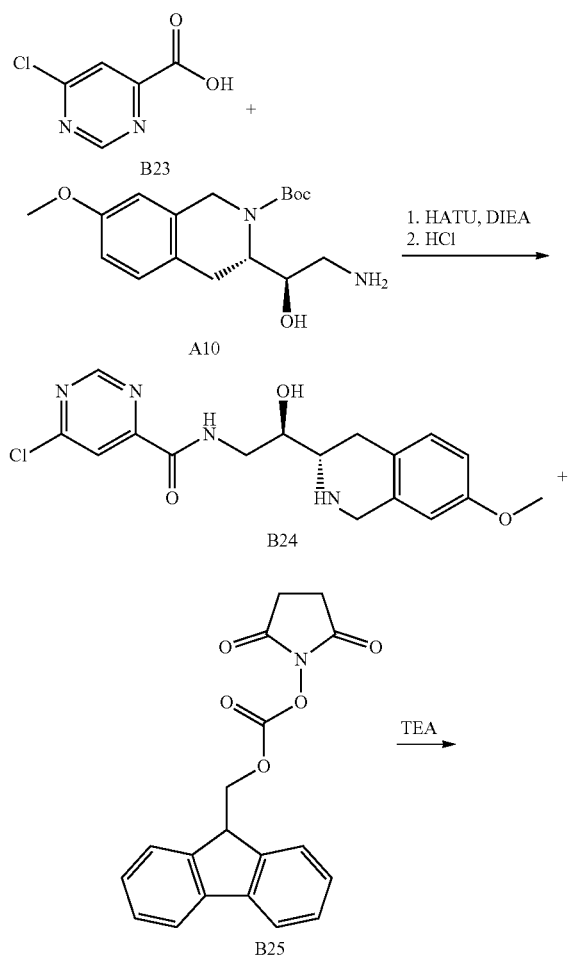

Compound 4 can be formed via the following four step sequence. Amide coupling between carboxylic acid B23 and amino alcohol A10, followed by Boc deprotection affords compound B24. Fmoc protection of B24 is achieved by reacting amine B24 with Fmoc-OSu B25 to afford B26. $S_NAr$ between chloropyrimidine B26 and amino oxetane B27 affords compound 4.

Scheme IX:

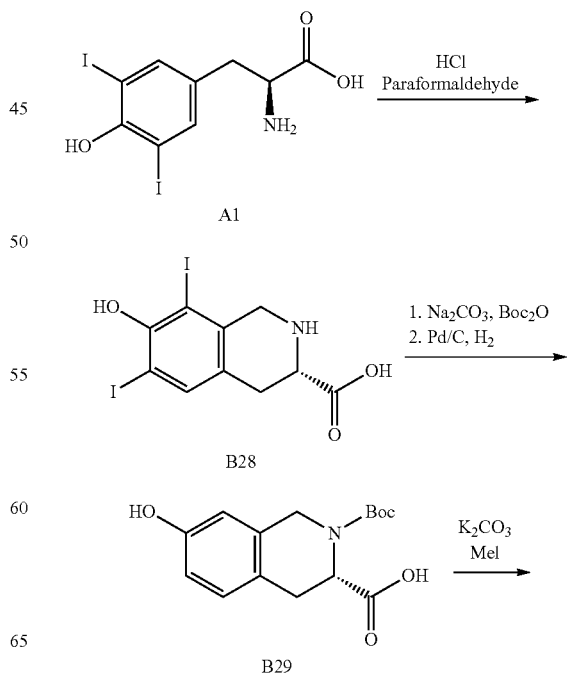

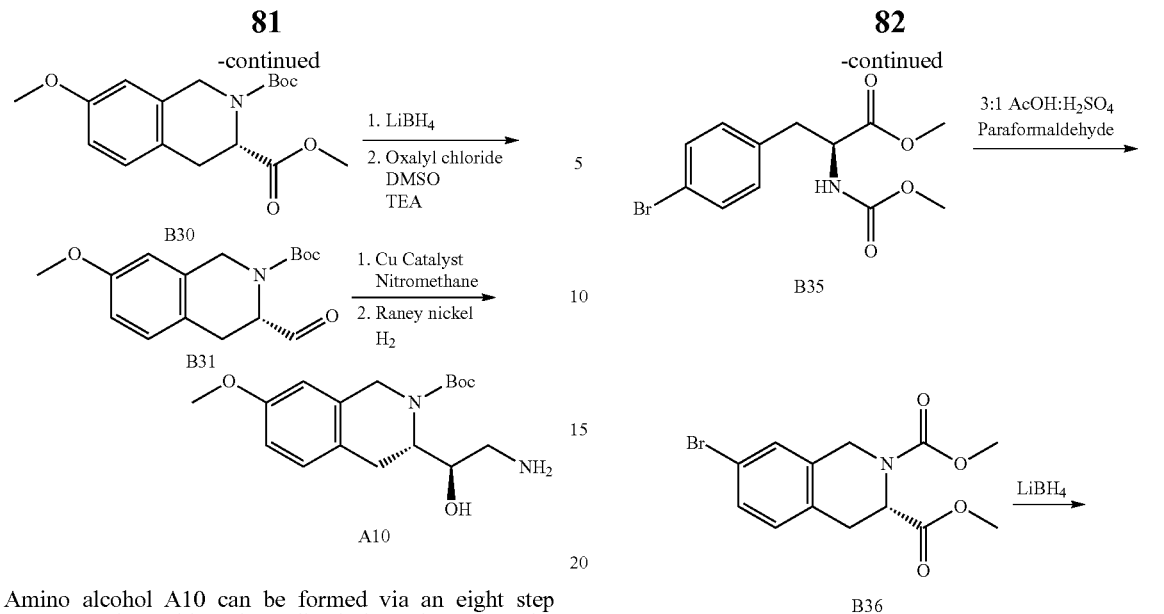

Amino alcohol A10 can be formed via an eight step sequence. Amino acid A1 is cyclized via a Pictet-Spengler reaction to afford THIQ B28. Boc protection followed by hydrogenation affords carboxylic acid B29. Alkylation affords ester B30, while reduction followed by oxidation affords aldehyde B31. Nitration followed by nitro reduction affords amino alcohol A10.

Scheme X:

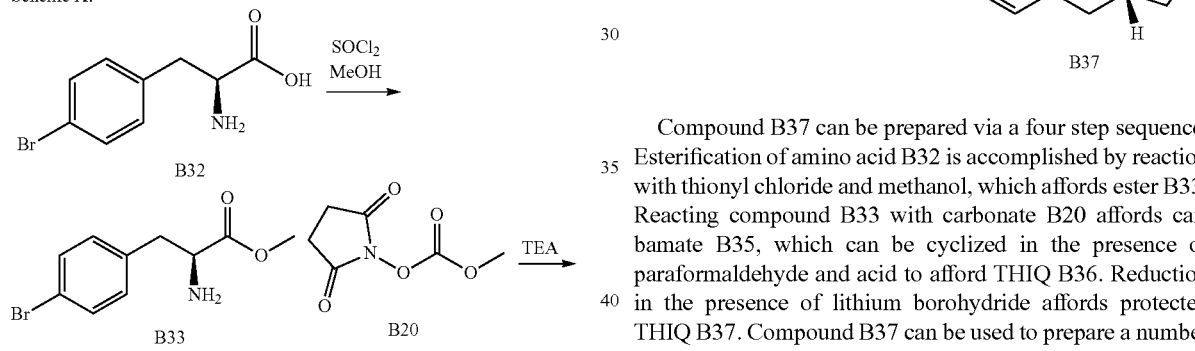

Compound B37 can be prepared via a four step sequence. Esterification of amino acid B32 is accomplished by reaction with thionyl chloride and methanol, which affords ester B33. Reacting compound B33 with carbonate B20 affords carbamate B35, which can be cyclized in the presence of paraformaldehyde and acid to afford THIQ B36. Reduction in the presence of lithium borohydride affords protected THIQ B37. Compound B37 can be used to prepare a number of intermediates as shown in the scheme below:

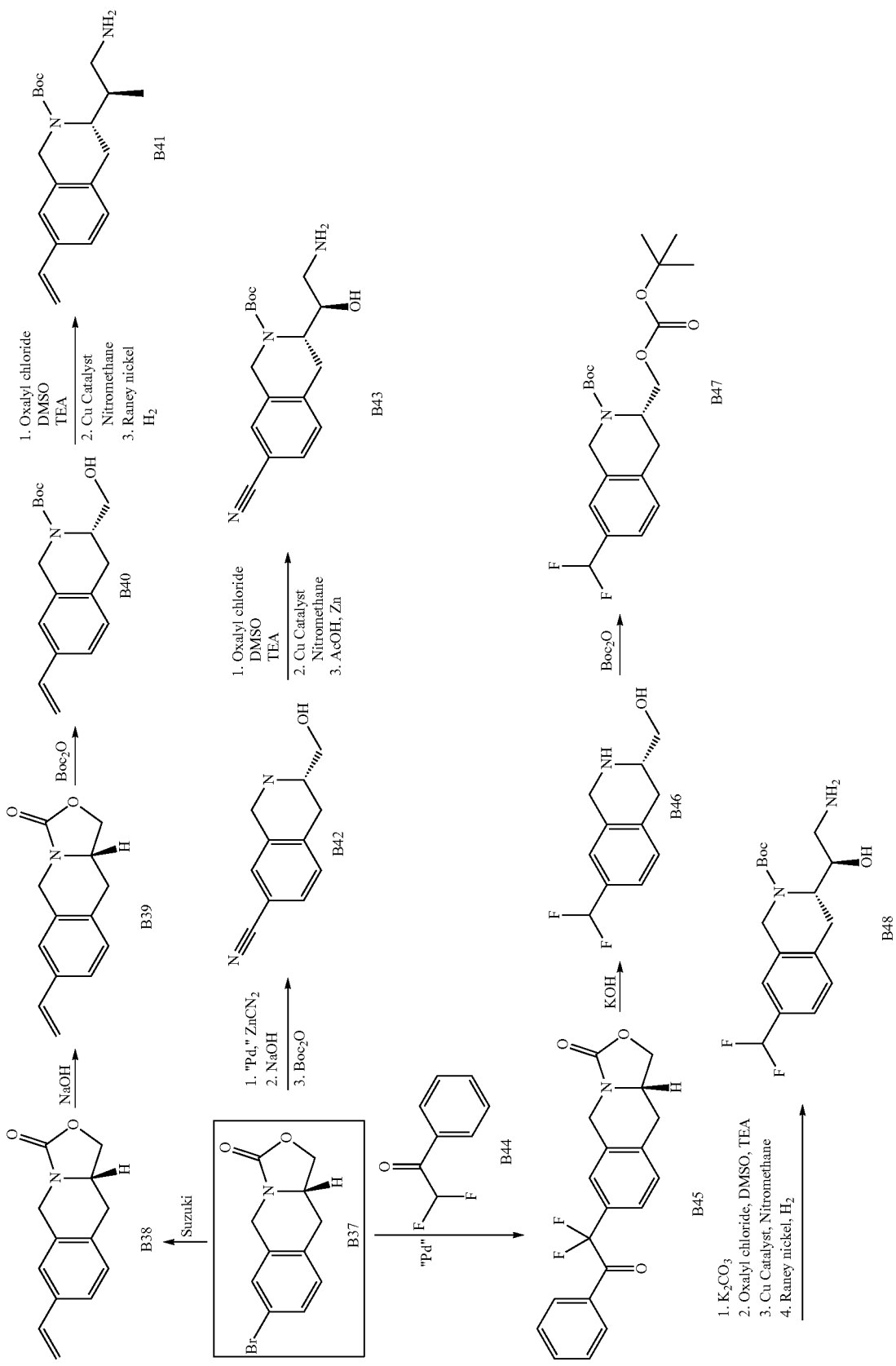

A Suzuki reaction with compound B37 affords alkene B38, while deprotection in the presence of base affords THIQ B39. Boc protection affords THIQ B40, while oxidation, nitration, and hydrogenation afford amino alcohol B41. Alternatively, a palladium catalyzed cyanation reaction, followed by deprotection and Boc protection affords THIQ B42. Oxidation, nitration, and nitro reduction afford amino alcohol B43. Alternatively, a palladium catalyzed insertion of B44 affords B45. Deprotection under basic conditions affords THIQ B46 and Boc protection affords THIQ B47. A deprotection under basic conditions, followed by oxidation, nitration, and hydrogenation afford amino alcohol B48.

Scheme XI:

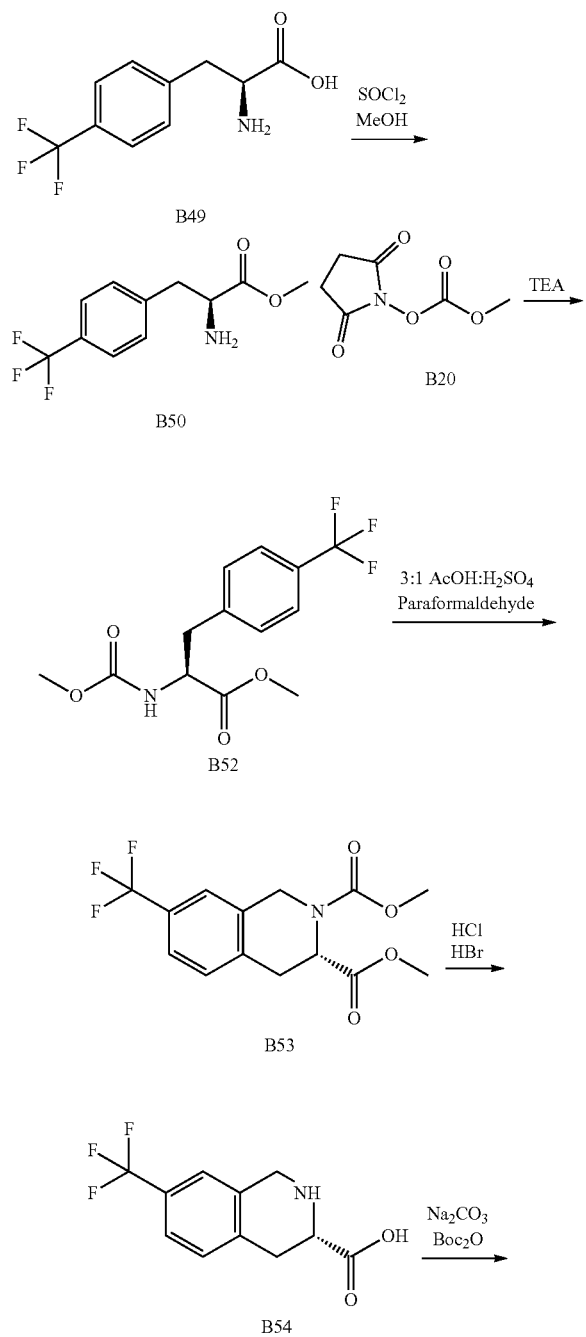

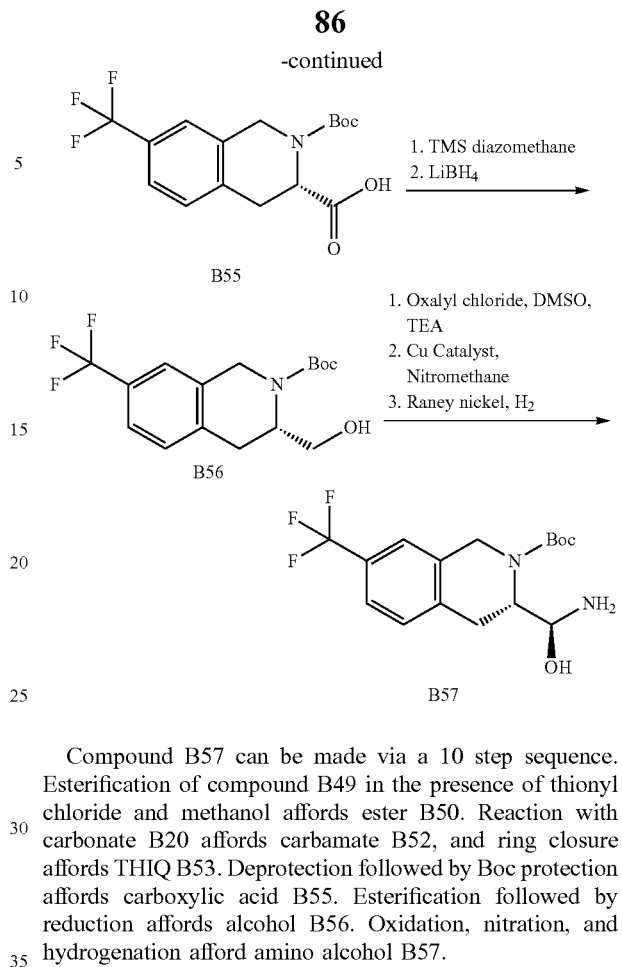

Compound B57 can be made via a 10 step sequence. Esterification of compound B49 in the presence of thionyl chloride and methanol affords ester B50. Reaction with carbonate B20 affords carbamate B52, and ring closure affords THIQ B53. Deprotection followed by Boc protection affords carboxylic acid B55. Esterification followed by reduction affords alcohol B56. Oxidation, nitration, and hydrogenation afford amino alcohol B57.

Preparation of Further Intermediates
Intermediate 1 (see Scheme II, Compound H9)

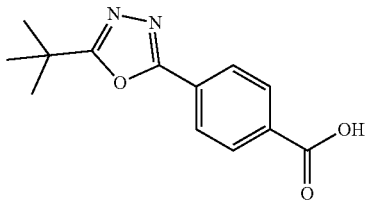 [SMILES: CC(C)(C)c1nnc(-c2ccc(C(=O)O)cc2)o1]

4-(5-(tert-butyl)-1,3,4-oxadiazol-2-yl)benzoic acid

Step 1: To a mixture of 4-(methoxycarbonyl)benzoic acid (5.0 g, 28 mmol), tert-butyl hydrazinecarboxylate (4.4 g, 33 mmol), and DMAP (13.6 g, 111 mmol) was added DCM (70 mL) and EDC (6.9 g, 36 mmol). The reaction mixture was stirred at 30° C. for 2 h. The mixture was washed with saturated aqueous sodium bicarbonate (50 mL) and water (50 mL), and then the organic layer was dried over anhydrous magnesium sulfate, filtered, and concentrated under reduced pressure. The residue was purified by column chromatography on silica (0-30% EtOAc/petroleum ether) to afford tert-butyl 2-(4-(methoxycarbonyl)benzoyl)hydrazinecarboxylate as a solid.

Step 2: A solution of tert-butyl 2-(4-(methoxycarbonyl)benzoyl)hydrazinecarboxylate (8.0 g, 27 mmol) in HCl (4 M in dioxane, 30 mL) was stirred at 30° C. for 2 h. The mixture was concentrated under reduced pressure to afford methyl 4-(hydrazinecarbonyl)benzoate hydrochloride as a solid which was used directly in the next step without further purification.

Step 3: To a solution of methyl 4-(hydrazinecarbonyl) benzoate hydrochloride (1.0 g, 4.3 mmol) and TEA (1.3 g, 13 mmol) in DCM (20 mL) at 0° C. under an atmosphere of nitrogen was added pivaloyl chloride (0.78 g, 6.5 mmol) dropwise. The reaction was stirred at 20° C. for 20 min. The mixture was quenched with water (20 mL) and extracted with DCM (3×20 mL). The combined organic layers were dried over magnesium sulfate, filtered, and concentrated under reduced pressure. The residue was purified by column chromatography on silica (0-20% EtOAc/petroleum ether) to afford methyl 4-(5-(tert-butyl)-1,3,4-oxadiazol-2-yl)benzoate as an oil. MS: 261 (M+1).

Step 4: To a solution of methyl 4-(5-(tert-butyl)-1,3,4-oxadiazol-2-yl)benzoate (250 mg, 0.86 mmol) in MeOH/water (10:1, 4 mL) was added lithium hydroxide hydrate (109 mg, 2.59 mmol). The mixture was stirred at 30° C. for 2 h. Then the mixture was acidified with HCl (1 N in water, 6 mL), diluted with water (10 mL), and extracted with EtOAc (3×10 mL). The combined organic layers were dried over magnesium sulfate, filtered, and concentrated under reduced pressure to afford 4-(5-(tert-butyl)-1,3,4-oxadiazol-2-yl)benzoic acid as a solid which was used directly in the next step without further purification. MS: 247 (M+1).

Intermediate 2 (see Scheme II, Compound H12)

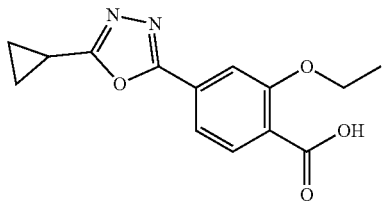 [SMILES: CCOc1cc(-c2nnc(C3CC3)o2)ccc1C(=O)O]

4-(5-cyclopropyl-1,3,4-oxadiazol-2-yl)-2-ethoxybenzoic acid

Intermediate 2 was synthesized using the same procedure as intermediate 1. MS: 275 (M+1).

Intermediate 3 (see Scheme IX, Compound A10)

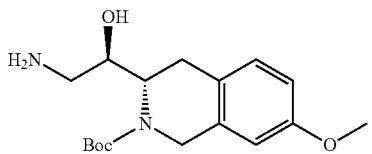 [SMILES: COc1ccc2c(c1)CN(C(=O)OC(C)(C)C)[C@H]([C@H](O)CN)C2]

(S)-tert-butyl 3-((R)-2-amino-1-hydroxyethyl)-7-methoxy-3,4-dihydroisoquinoline-2(1H)-carboxylate—Alternative Synthesis of Compound A10, in Addition to that Detailed in Example 1

Step 1: To a solution of (S)-2-amino-3-(4-hydroxy-3,5-diiodophenyl)propanoic acid (60 g, 139 mmol) in concentrated HCl (800 mL) was added 1,2-dimethoxyethane (40 mL) and paraformaldehyde (15.6 g, 520 mmol). The mixture was stirred vigorously and slowly heated to 75° C. After 30 min, more concentrated HCl (400 mL), 1,2-dimethoxyethane (20 mL) and paraformaldehyde (10.4 g, 0.346 mol) were added, and the mixture was heated at 75° C. for 12 h. The suspension was cooled in an ice bath and the solid was collected by filtration. The filter cake was washed thoroughly with 1,2-dimethoxyethane (100 mL) and dried under reduced pressure to afford (S)-7-hydroxy-6,8-diiodo-1,2,3,4-tetrahydroisoquinoline-3-carboxylic acid as a solid, which was used directly in the next step without further purification. MS: 446 (M+1).

Step 2: To a solution of (S)-7-hydroxy-6,8-diiodo-1,2,3,4-tetrahydroisoquinoline-3-carboxylic acid (31 g, 70 mmol) in THF (200 mL) and water (100 mL) was added sodium carbonate (15 g, 140 mmol) slowly. Di-tert-butyl dicarbonate (32 mL, 140 mmol) was added and the mixture was stirred at 25° C. for 1 h. The mixture was concentrated under reduced pressure, and then was diluted with MTBE (100 mL), water (200 mL), and acidified to ~pH 3 with citric acid. The mixture was extracted with EtOAc (2×50 mL), and the combined organic layers were dried over anhydrous sodium sulfate, filtered, and concentrated under reduced pressure to afford (S)-2-(tert-butoxycarbonyl)-7-hydroxy-6,8-diiodo-1,2,3,4-tetrahydroisoquinoline-3-carboxylic acid as a solid, which was used directly in the next step without further purification.

Step 3: To a solution of (S)-2-(tert-butoxycarbonyl)-7-hydroxy-6,8-diiodo-1,2,3,4-tetrahydroisoquinoline-3-carboxylic acid (30 g, 55 mmol) in MeOH (400 mL) under an atmosphere of nitrogen was added palladium on carbon (10 wt %, 5.9 g, 5.5 mmol). The mixture was stirred at 30° C. under hydrogen gas (30 psi) for 24 h. The mixture was filtered and the filtrate was concentrated under reduced pressure to afford (S)-2-(tert-butoxycarbonyl)-7-hydroxy-1,2,3,4-tetrahydroisoquinoline-3-carboxylic acid as an oil. MS: 194 (M-Boc+H).

Step 4: To a solution of (S)-2-(tert-butoxycarbonyl)-7-hydroxy-1,2,3,4-tetrahydroisoquinoline-3-carboxylic acid (13 g, 44 mmol) in DMSO (80 mL) was added potassium carbonate (12 g, 88 mmol) and iodomethane (16.4 g, 116 mmol). The mixture was stirred at 30° C. for 4 h. The reaction was diluted with water (400 mL) and extracted with EtOAc (2×200 mL). The combined organic layers were washed with brine (50 mL), dried over anhydrous sodium sulfate, filtered, and concentrated under reduced pressure. The residue was purified by column chromatography on silica (0-30% ethyl acetate/petroleum ether) to afford (S)-2-tert-butyl 3-methyl 7-hydroxy-3,4-dihydroisoquinoline-2,3(1H)-dicarboxylate as an oil. MS: 308 (M+1).

Step 5: To a solution of (S)-2-tert-butyl 3-methyl 7-hydroxy-3,4-dihydroisoquinoline-2,3(1H)-dicarboxylate (3.9 g, 12.7 mmol) in DMSO (40 mL) was added potassium carbonate (3.5 g, 25 mmol) and iodomethane (6.3 g, 44 mmol). The mixture was stirred at 30° C. for 5 h. The reaction was diluted with water (200 mL) and extracted with EtOAc (2×100 mL). The combined organic layers were washed with brine (50 mL), dried over anhydrous sodium sulfate, filtered, and concentrated under reduced pressure. The residue was purified by column chromatography on silica (0-30% ethyl acetate/petroleum ether) to afford (S)-2-tert-butyl 3-methyl 7-methoxy-3,4-dihydroisoquinoline-2,3(1H)-dicarboxylate as an oil. MS: 322 (M+1).

Step 6: To a solution of (S)-2-tert-butyl 3-methyl 7-methoxy-3,4-dihydroisoquinoline-2,3(1H)-dicarboxylate (3 g, 9.3 mmol) in THF (30 mL) was added lithium borohydride (0.41 g, 19 mmol) at 0° C. The mixture was stirred at 30° C. for 16 h. The mixture was diluted with saturated aqueous ammonium chloride (50 mL) and extracted with EtOAc (3×50 mL). The combined organic layers were dried over anhydrous sodium sulfate, filtered, and concentrated under reduced pressure. The residue was purified by column chromatography on silica (0-40% ethyl acetate/petroleum ether) to afford (S)-tert-butyl 3-(hydroxymethyl)-7-methoxy-3,4-dihydroisoquinoline-2(1H)-carboxylate as an oil. MS: 294 (M+1).

Step 7: To a solution of oxalyl chloride (1.2 mL, 13.5 mmol) in DCM (30 mL) was added DMSO (1.9 mL, 27 mmol) in DCM (2 mL) at −78° C. The solution was stirred at −78° C. for 0.5 h, and (S)-tert-butyl 3-(hydroxymethyl)-7-methoxy-3,4-dihydroisoquinoline-2(1H)-carboxylate (2.2 g, 7.5 mmol) in DCM (5 mL) was added dropwise. The solution was stirred at −78° C. for 0.5 h, and TEA (7.5 mL, 54 mmol) was added dropwise. The solution was stirred at −78° C. for 0.5 h, and slowly warmed to 10° C. and stirred for 0.5 h. The solution was quenched with water (50 mL), and extracted with DCM (2×50 mL). The combined organic layers were washed with HCl (0.6 M in water, 2×100 mL), dried over anhydrous sodium sulfate, filtered, and concentrated under reduced pressure to afford (S)-tert-butyl 3-formyl-7-methoxy-3,4-dihydroisoquinoline-2(1H)-carboxylate as an oil which was used directly in the next step without further purification. MS: 236 (M-tBu+H).

Step 8: To a solution of (S)-tert-butyl 3-formyl-7-methoxy-3,4-dihydroisoquinoline-2(1H)-carboxylate (2.0 g, 6.9 mmol) in ethanol (4 mL) was added (1R,2R)-N1,N2-bis(4-chlorobenzyl)cyclohexane-1,2-diamine Copper(II) acetate complex (0.75 g, 1.4 mmol) at 30° C. The solution was cooled to 0° C., nitromethane (4.2 g, 69 mmol) was added, and the reaction was stirred at 30° C. for 40 h. The mixture was concentrated under reduced pressure, and the residue was purified by column chromatography on silica (0-50% ethyl acetate/petroleum ether) to afford (S)-tert-butyl 3-((R)-1-hydroxy-2-nitroethyl)-7-methoxy-3,4-dihydroisoquinoline-2(1H)-carboxylate as an oil. MS: 253 (M-Boc+H).

Step 9: To a solution of (S)-tert-butyl 3-((R)-1-hydroxy-2-nitroethyl)-7-methoxy-3,4-dihydroisoquinoline-2(1H)-carboxylate (500 mg, 1.42 mmol) in ethanol (20 mL) was added Raney nickel (500 mg, 8.5 mmol). The solution was stirred at 20° C. under a balloon of hydrogen gas for 16 h. The mixture was diluted with water (20 mL) and filtered through Celite. The filtrate was concentrated under reduced pressure to afford (S)-tert-butyl 3-((R)-2-amino-1-hydroxyethyl)-7-methoxy-3,4-dihydroisoquinoline-2(1H)-carboxylate as an oil. MS: 323 (M+1).

Intermediate 4 (see Scheme X, Compound B41)

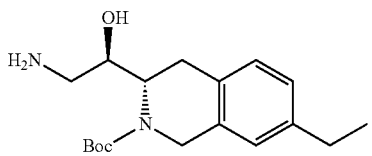 [SMILES: CCc1ccc2c(c1)CN(C(=O)OC(C)(C)C)[C@H]([C@H](O)CN)C2]

tert-butyl (3S)-3-[(1R)-2-amino-1-hydroxyethyl]-7-ethyl-3,4-dihydroisoquinoline-2(1H)-carboxylate Step 1: To a solution of (S)-2-amino-3-(4-bromophenyl)propanoic acid (25 g, 102 mmol) in MeOH (250 mL) was added SOCl$_2$ (22.4 mL, 307 mmol) dropwise at 25° C. The mixture was stirred at 80° C. for 15 h. The mixture was concentrated under reduced pressure to give (S)-methyl 2-amino-3-(4-bromophenyl)propanoate as a solid which was used directly in the next step without further purification. MS: 258, 260 (M, M+2).

Step 2: To a solution of (S)-methyl 2-amino-3-(4-bromophenyl)propanoate (26.4 g, 102 mmol) in DCM (250 mL) was added TEA (18.5 mL, 133 mmol) at 25° C. Added 2,5-dioxopyrrolidin-1-yl methyl carbonate (21.3 g, 123 mmol), and the mixture was stirred at 25° C. for 1.5 h. The mixture was concentrated under reduced pressure, and the residue was purified by column chromatography on silica (0-30% ethyl acetate/petroleum ether) to afford (S)-methyl 3-(4-bromophenyl)-2-((methoxycarbonyl)amino)propanoate as an oil. MS: 316, 318 (M, M+2).

Step 3: To a solution of (S)-methyl 3-(4-bromophenyl)-2-((methoxycarbonyl)amino)propanoate (28 g, 89 mmol) in acetic acid/sulfuric acid (3:1, v/v, 120 mL) was added paraformaldehyde (3.3 g, 89 mmol) at 25° C. The mixture was stirred at 25° C. for 1.5 h. The mixture was poured into ice water (500 mL), and diluted with EtOAc (200 mL). The mixture was extracted with EtOAc (4×200 mL). The combined organic layers were washed with saturated aqueous sodium bicarbonate (500 mL) and brine (400 mL), dried over anhydrous sodium sulfate, filtered, and concentrated under reduced pressure to afford (S)-dimethyl 7-bromo-3,4-dihydroisoquinoline-2,3(1H)-dicarboxylate as an oil which was used directly in next step. MS: 328, 330 (M, M+2).

Step 4: To a solution of (S)-dimethyl 7-bromo-3,4-dihydroisoquinoline-2,3(1H)-dicarboxylate (5 g, 15 mmol) in THF (60 mL) was added lithium borohydride (0.50 g, 23 mmol) slowly at 25° C. The mixture was stirred at 25° C. for 12 h. The reaction was diluted with water (100 mL) and EtOAc (50 mL). The mixture was extracted with EtOAc (3×50 mL), and the combined organic layers were dried over anhydrous sodium sulfate, filtered, and concentrated under reduced pressure. The residue was purified by column chromatography on silica (0-20% ethyl acetate/petroleum ether) to afford (S)-7-bromo-10,10a-dihydro-1H-oxazolo[3,4-b]isoquinolin-3(5H)-one as a solid. MS: 308, 310 (M+K, M+K+2).

Step 5: A suspension of (S)-7-bromo-10,10a-dihydro-1H-oxazolo[3,4-b]isoquinolin-3(5H)-one (200 mg, 0.75 mmol), potassium trifluoro(vinyl)borate (400 mg, 3 mmol), cesium carbonate (406 mg, 3 mmol), and chloro(2-dicyclohexylphosphino-2',4',6'-triisopropyl-1,1'-biphenyl)[2-(2'-amino-1,1'-biphenyl)]palladium(II) (59 mg, 0.075 mmol) in THF (20 mL) and water (3 mL) was placed under a nitrogen atmosphere by performing vacuum/nitrogen cycles (3×). The reaction mixture was stirred at 85° C. for 16 h. The mixture was concentrated under reduced pressure, and the residue was purified by column chromatography on silica (0-20% ethyl acetate/petroleum ether) to afford (S)-7-vinyl-10,10a-dihydro-1H-oxazolo[3,4-b]isoquinolin-3(5H)-one as a solid. MS: 216 (M+1).

Step 6: To a solution of (S)-7-vinyl-10,10a-dihydro-1H-oxazolo[3,4-b]isoquinolin-3(5H)-one (1.2 g, 5.6 mmol) in THF (50 mL) was added sodium hydroxide (2 M in water, 66 mL, 132 mmol) at 40° C. The mixture was stirred at 40° C. for 15 h to afford (S)-(7-vinyl-1,2,3,4-tetrahydroisoquinolin-3-yl)methanol which was used directly in the next step. MS: 190 (M+1).

Step 7: To the solution of (S)-(7-vinyl-1,2,3,4-tetrahydroisoquinolin-3-yl)methanol (1.1 g, 5.6 mmol) in THF (50 mL) and sodium hydroxide (2 M in water, 66 mL, 132 mmol) obtained in step 6 was added di-tert-butyl dicarbonate (3.24 mL, 13.9 mmol). The mixture was stirred at 25° C. for 1 h. The organic phase was separated, and the aqueous phase was extracted with EtOAc (3×50 mL). The combined organic layers were washed with brine (50 mL), dried over anhydrous sodium sulfate, filtered, and concentrated under reduced pressure. The residue was purified by column chromatography on silica (0-40% ethyl acetate/petroleum ether) to afford (S)-tert-butyl 3-(hydroxymethyl)-7-vinyl-3,4-dihydroisoquinoline-2(1H)-carboxylate as an oil. MS: 190 (M-Boc+H).

Step 8: To a solution of oxalyl chloride (0.106 mL, 1.24 mmol) in DCM (3 mL) was added DMSO (0.180 mL, 2.5 mmol) in DCM (1 mL) at −78° C. The solution was stirred at −78° C. for 0.5 h, and (S)-tert-butyl 3-(hydroxymethyl)-7-vinyl-3,4-dihydroisoquinoline-2(1H)-carboxylate (200 mg, 0.69 mmol) in DCM (1 mL) was added dropwise. The solution was stirred at −78° C. for 0.5 h, and TEA (0.7 mL, 5 mmol) was added dropwise. The solution was stirred at −78° C. for 0.5 h, and slowly warmed to 25° C. for 0.5 h. The solution was quenched with water (20 mL), and extracted with DCM (2×30 mL). The combined organic layers were washed with HCl (0.25 M in water, 2×30 mL), dried over anhydrous sodium sulfate, filtered, and concentrated under reduced pressure to afford (S)-tert-butyl 3-formyl-7-vinyl-3,4-dihydroisoquinoline-2(1H)-carboxylate as an oil which was used directly in the next step without further purification.

Step 9: To a solution of (S)-tert-butyl 3-formyl-7-vinyl-3,4-dihydroisoquinoline-2(1H)-carboxylate (500 mg, 1.74 mmol) in ethanol (4 mL) was added (1R,2R)—N1,N2-bis(4-chlorobenzyl)cyclohexane-1,2-diamine Copper(II) acetate complex (189 mg, 0.348 mmol) in ethanol (1 mL) at 25° C. The solution was cooled to 0° C., and nitromethane (1.1 g, 17.4 mmol) was added. The reaction was stirred at 25° C. for 48 h. The mixture was concentrated under reduced pressure, and the residue was purified by prep-TLC (1:5 ethyl acetate/petroleum ether, $R_f$=0.3) to afford (S)-tert-butyl 3-((R)-1-hydroxy-2-nitroethyl)-7-vinyl-3,4-dihydroisoquinoline-2(1H)-carboxylate as an oil.

Step 10: To a solution of (S)-tert-butyl 3-((R)-1-hydroxy-2-nitroethyl)-7-vinyl-3,4-dihydroisoquinoline-2(1H)-carboxylate (180 mg, 0.517 mmol) in ethanol (30 mL) was added Raney nickel (200 mg, 3.41 mmol) under a nitrogen atmosphere. The mixture was degassed and backfilled with hydrogen gas (3×). The resulting mixture was stirred under hydrogen gas (15 psi) at 25° C. for 1 h. The mixture was filtered, and the filtrate was concentrated under reduced pressure to afford tert-butyl (3S)-3-[(1R)-2-amino-1-hydroxyethyl]-7-ethyl-3,4-dihydroisoquinoline-2(1H)-carboxylate as an oil which was used directly in the next step without further purification. MS: 321 (M+1).

Intermediate 5 (see Scheme X, Compound 848)

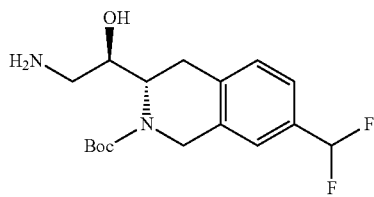 [SMILES: CC(C)(C)OC(=O)N1Cc2cc(C(F)F)ccc2C[C@H]1[C@H](O)CN]

(S)-tert-butyl 3-((R)-2-amino-1-hydroxyethyl)-7-(difluoromethyl)-3,4-dihydroisoquinoline-2(1H)-carboxylate Step 1: A mixture of bis(dibenzylideneacetone)palladium (0) (0.27 g, 0.47 mmol), 2-dicyclohexylphosphino-2',6'-dimethoxybiphenyl (0.21 g, 0.51 mmol) and cesium carbonate (12.2 g, 37.3 mmol) in toluene (60 mL) was stirred at 25° C. for 20 min under an atmosphere of argon. Added (S)-7-bromo-10,10a-dihydro-1H-oxazolo[3,4-b]isoquinolin-3(5H)-one (2.5 g, 9.3 mmol) and 2,2-difluoro-1-phenylethanone (2.2 g, 14 mmol), and the reaction mixture was heated at 100° C. for 15 h. The mixture was cooled to room temperature and water (100 mL) was added. The mixture was extracted with EtOAc (3×50 mL) and the combined organic layers were dried over sodium sulfate, filtered, and concentrated under reduced pressure. The residue was purified by column chromatography on silica (0-50% ethyl acetate/petroleum ether) to afford (S)-7-(1,1-difluoro-2-oxo-2-phenylethyl)-10,10a-dihydro-1H-oxazolo[3,4-b]isoquinolin-3(5H)-one as a solid. MS: 344 (M+1).

Step 2: To a mixture of (S)-7-(1,1-difluoro-2-oxo-2-phenylethyl)-10,10a-dihydro-1H-oxazolo[3,4-b]isoquinolin-3(5H)-one (2 g, 6 mmol) in toluene (30 mL) was added potassium hydroxide (1.6 g, 28 mmol) and water (2 mL). The mixture was heated at 110° C. for 12 h to afford (S)-(7-(difluoromethyl)-1,2,3,4-tetrahydroisoquinolin-3-yl)methanol. The mixture was used in the next step without further purification. MS: 214 (M+1).

Step 3: To a mixture of (S)-(7-(difluoromethyl)-1,2,3,4-tetrahydroisoquinolin-3-yl) methanol (1.2 g, 6 mmol) in toluene (20 mL) was added potassium hydroxide (1.6 g, 28 mmol) and water (2 mL). Di-tert-butyl dicarbonate (6.4 g, 29 mmol) was added and the mixture was stirred at 16° C. for 12 h. The reaction was diluted with water (20 mL) and the mixture was extracted with EtOAc (2×20 mL). The combined organic layers were dried over anhydrous sodium sulfate, filtered, and concentrated under reduced pressure. The residue was purified by column chromatography on silica (0-10% ethyl acetate/petroleum ether) to afford (S)-tert-butyl 3-(((tert-butoxycarbonyl)oxy)methyl)-7-(difluoromethyl)-3,4-dihydroisoquinoline-2(1H)-carboxylate as an oil. MS: 436 (M+Na).

Step 4: To a mixture of (S)-tert-butyl 3-(((tert-butoxycarbonyl)oxy)methyl)-7-(difluoromethyl)-3,4-dihydroisoquinoline-2(1H)-carboxylate (1.2 g, 2.9 mmol) in methanol (5 mL) was added potassium carbonate (0.40 g, 2.9 mmol). The mixture was stirred at 16° C. for 12 h. The mixture was filtered, and the filtrate was concentrated under reduced pressure. The residue was purified by column chromatography on silica (0-30% ethyl acetate/petroleum ether) to afford (S)-tert-butyl 7-(difluoromethyl)-3-(hydroxymethyl)-3,4-dihydroisoquinoline-2(1H)-carboxylate as an oil.

Step 5: To a solution of oxalyl chloride (0.100 mL, 1.15 mmol) in DCM (10 mL) was added DMSO (0.16 mL, 2.3 mmol) in DCM (3 mL) at −78° C. The solution was stirred at −78° C. for 0.5 h, and (S)-tert-butyl 7-(difluoromethyl)-3-(hydroxymethyl)-3,4-dihydroisoquinoline-2(1H)-carboxylate (200 mg, 0.64 mmol) in DCM (3 mL) was added dropwise. The solution was stirred at −78° C. for 0.5 h, and TEA (0.641 mL, 4.60 mmol) was added dropwise. The solution was stirred at −78° C. for 0.5 h. The solution was quenched with water (40 mL), and extracted with DCM (2×40 mL). The combined organic layers were washed with saturated sodium chloride (40 mL), dried over anhydrous sodium sulfate, filtered, and concentrated under reduced pressure to afford (S)-tert-butyl 7-(difluoromethyl)-3-formyl-3,4-dihydroisoquinoline-2(1H)-carboxylate as an oil which was used directly in the next step without further purification.

Step 6: To a solution of (S)-tert-butyl 7-(difluoromethyl)-3-formyl-3,4-dihydroisoquinoline-2(1H)-carboxylate (199 mg, 0.639 mmol) in ethanol (2 mL) was added (1R,2R)—N1,N2-bis(4-chlorobenzyl)cyclohexane-1,2-diamine Copper(II) acetate complex (69 mg, 0.13 mmol) in ethanol (1 mL). The solution was cooled to 0° C., and nitromethane (0.345 mL, 6.39 mmol) was added. The reaction was stirred at 16° C. for 18 h. The mixture was concentrated under reduced pressure, and the residue was purified by column chromatography on silica (0-20% ethyl acetate/petroleum ether) to afford (S)-tert-butyl 7-(difluoromethyl)-3-((R)-1-hydroxy-2-nitroethyl)-3,4-dihydroisoquinoline-2(1H)-carboxylate as an oil. MS: 317 (M-tBu+H).

Step 7: To a solution of (S)-tert-butyl 7-(difluoromethyl)-3-((R)-1-hydroxy-2-nitroethyl)-3,4-dihydroisoquinoline-2(1H)-carboxylate (230 mg, 0.62 mmol) in methanol (30 mL) was added Raney nickel (500 mg, 8.52 mmol) under an atmosphere of nitrogen. The mixture was degassed and backfilled with hydrogen gas (3×). The resulting mixture was stirred under hydrogen (15 psi) at 25° C. for 1 h. The mixture was filtered, and the filtrate was concentrated under reduced pressure to afford (S)-tert-butyl 3-((R)-2-amino-1-hydroxyethyl)-7-(difluoromethyl)-3,4-dihydroisoquinoline-2(1H)-carboxylate as an oil, which was used directly in the next step without further purification. MS: 343 (M+1).

Intermediate 6 (see Scheme V, Compound H16)

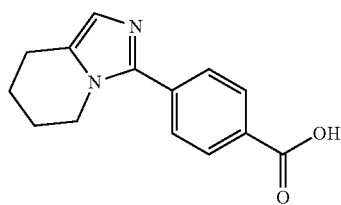 [SMILES: O=C(O)c1ccc(-c2ncc3n2CCCC3)cc1]

4-(5,6,7,8-tetrahydroimidazo[1,5-a]pyridin-3-yl)benzoic acid

Step 1: To an oven-dried, nitrogen-cooled vial was added butyldi-1-adamantylphosphine (29 mg, 0.082 mmol), palladium(II) acetate (9.2 mg, 0.041 mmol), and toluene (2 mL). The reaction mixture was heated at 50° C. for 30 minutes. To the preactivated catalyst system was added 5,6,7,8-tetrahydroimidazo[1,5-a]pyridine (50 mg, 0.41 mmol), ethyl 4-bromobenzoate (141 mg, 0.61 mmol), potassium carbonate (170 mg, 1.2 mmol), and pivalic acid (48 μL, 0.41 mmol). The mixture was evacuated and backfilled 3× with nitrogen and stirred at 105° C. for 16 h. The reaction was cooled to room temperature, filtered, and concentrated under reduced pressure. The residue was purified by column chromatography on silica gel (0-15% MeOH/DCM) to afford ethyl 4-(5,6,7,8-tetrahydroimidazo[1,5-a]pyridin-3-yl)benzoate as an oil. MS: 271 (M+1).

Step 2: To a solution of ethyl 4-(5,6,7,8-tetrahydroimidazo[1,5-a]pyridin-3-yl)benzoate (41 mg, 0.15 mmol) dissolved in THF (1.2 mL), MeOH (0.12 mL), and water (0.12 mL) was added lithium hydroxide monohydrate (32 mg, 0.75 mmol). The mixture was stirred at room temperature for 16 h. The reaction mixture was filtered and the filtrate was concentrated under reduced pressure to afford lithium 4-(5,6,7,8-tetrahydroimidazo[1,5-a]pyridin-3-yl)benzoate as a solid. MS: 243 (M+1).

Intermediate 7 (see Scheme IV and Scheme V, Compound H16)

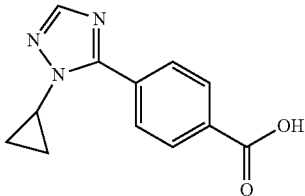 [SMILES: O=C(O)c1ccc(-c2ncnn2C2CC2)cc1]

4-(1-cyclopropyl-1H-1,2,4-triazol-5-yl)benzoic acid

Step 1: A solution of cyclopropylhydrazine hydrochloride (4 g, 37 mmol) in formamide (14.6 mL, 368 mmol) was heated at 130° C. for 60 h. The mixture was cooled to room temperature and brine (100 mL) was added. The mixture was extracted with EtOAc (3×30 mL), and the combined organic layers were washed with brine (20 mL), dried over anhydrous magnesium sulfate, filtered, and concentrated under reduced pressure. The residue was purified by column chromatography on silica (0-40% ethyl acetate/petroleum ether) to afford 1-cyclopropyl-1H-1,2,4-triazole as an oil.

Step 2: A mixture of 1-cyclopropyl-1H-1,2,4-triazole (200 mg, 1.83 mmol), methyl 4-bromobenzoate (591 mg, 2.75 mmol), 2,2-dimethylbutanoic acid (64 mg, 0.55 mmol), di(adamantan-1-yl)(butyl)phosphine (263 mg, 0.733 mmol), potassium carbonate (1.3 g, 9.2 mmol), and palladium(II) acetate (82 mg, 0.37 mmol) in toluene (10 mL) was degassed and backfilled with nitrogen gas (3×). The mixture was heated at 120° C. for 12 h. The mixture was concentrated under reduced pressure, and the residue was dissolved in water (10 mL) and EtOAc (10 mL). The organic layer was separated and the aqueous layer was extracted with EtOAc (3×15 mL). The combined organic layers were washed with brine (20 mL), dried over anhydrous magnesium sulfate, filtered, and concentrated under reduced pressure. The residue was purified by prep-TLC (petroleum ether:EtOAc=1:1) to afford methyl 4-(1-cyclopropyl-1H-1,2,4-triazol-5-yl)benzoate as an oil. MS: 244 (M+1).

Step 3: To a mixture of methyl 4-(1-cyclopropyl-1H-1,2,4-triazol-5-yl)benzoate (215 mg, 0.88 mmol) in MeOH (3 mL) and water (1 mL) was added lithium hydroxide hydrate (74 mg, 1.8 mmol). The solution was stirred at 10° C. for 1 h. The mixture was concentrated under reduced pressure. The residue was diluted with water and the pH of the solution was adjusted by the addition of HCl (1 M in water) to ~pH 2. The mixture was extracted with EtOAc (3×30 mL). The combined organic layers were washed with brine (20 mL), dried over anhydrous magnesium sulfate, filtered, and concentrated under reduced pressure to afford 4-(1-cyclopropyl-1H-1,2,4-triazol-5-yl)benzoic acid as a solid, which was used in next step without further purification. MS: 230 (M+1).

Intermediate 8 (see Scheme III, Compound B7)

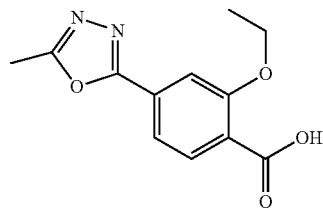 [SMILES: CCOc1cc(-c2nnc(C)o2)ccc1C(=O)O]

2-ethoxy-4-(5-methyl-1,3,4-oxadiazol-2-yl)benzoic acid

Step 1: To a solution of 3-ethoxy-4-(ethoxycarbonyl) benzoic acid (1 g, 4.2 mmol) in DCM (35 mL) was added HATU (2.1 g, 5.5 mmol), DIEA (2.2 mL, 12.6 mmol), and acetohydrazide (0.311 g, 4.20 mmol). The solution was stirred at 20° C. for 16 h, and the solution was concentrated under reduced pressure. The residue was purified by column chromatography on silica (0-5% MeOH/DCM) to afford ethyl 4-(2-acetylhydrazinecarbonyl)-2-ethoxybenzoate as a solid. MS: 295 (M+1).

Step 2: A mixture of ethyl 4-(2-acetylhydrazinecarbonyl)-2-ethoxybenzoate (1 g, 3.4 mmol) in POCl₃ (13 mL, 140 mmol) was placed under a nitrogen atmosphere by performing three vacuum/nitrogen cycles. The mixture was heated at 105° C. for 20 h. The mixture was poured into ice water (100 mL) and extracted with DCM (2×100 mL). The combined organic layers were washed with saturated aqueous sodium bicarbonate (70 mL), dried over anhydrous sodium sulfate, filtered, and concentrated under reduced pressure. The residue was purified by column chromatography on silica (0-20% EtOAc/hexanes) to afford ethyl 2-ethoxy-4-(5-methyl-1,3,4-oxadiazol-2-yl)benzoate as a solid. MS: 277 (M+1).

Step 3: To a solution of ethyl 2-ethoxy-4-(5-methyl-1,3,4-oxadiazol-2-yl)benzoate (500 mg, 1.08 mmol) in MeOH (5 mL) and water (2 mL) was added lithium hydroxide (230 mg, 5.50 mmol). The reaction was stirred at 25° C. for 4 h. The reaction was quenched by the addition of water (30 mL), and HCl (6 M in water) was added to ~pH 2. The mixture was extracted with EtOAc (3×30 mL), and the combined organic layers were washed with brine, dried over anhydrous magnesium sulfate, filtered, and concentrated under reduced pressure to afford 2-ethoxy-4-(5-methyl-1,3,4-oxadiazol-2-yl)benzoic acid as a solid which was used in next step without further purification. MS: 249 (M+1).

Intermediate 9 (see Scheme XI, Compound B57)

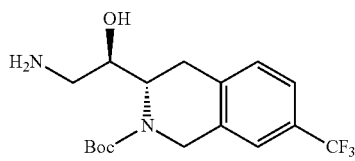 [SMILES: CC(C)(C)OC(=O)N1Cc2cc(C(F)(F)F)ccc2C[C@H]1[C@H](O)CN]

tert-butyl (3S)-3-[(1R)-2-amino-1-hydroxyethyl]-7-(trifluoromethyl)-3,4-dihydroisoquinoline-2(1H)-carboxylate Step 1: To a solution of (S)-2-amino-3-(4-(trifluoromethyl)phenyl)propanoic acid (7.5 g, 32 mmol) in MeOH (60 mL) was added thionyl chloride (7 mL, 96 mmol) dropwise at 15° C. The reaction was stirred at 80° C. for 15 h. The mixture was concentrated under reduced pressure to afford (S)-methyl 2-amino-3-(4-(trifluoromethyl)phenyl)propanoate as a solid which was used directly in next step without further purification. MS: 248 (M+1).

Step 2: To a solution of (S)-methyl 2-amino-3-(4-(trifluoromethyl)phenyl)propanoate (7.9 g, 32 mmol) in DCM (70 mL) was added TEA (6.7 mL, 48 mmol) and 2,5-dioxopyrrolidin-1-yl methyl carbonate (6.7 g, 39 mmol). The reaction was stirred at 25° C. for 1 h, and the mixture was concentrated under reduced pressure. The residue was purified by column chromatography on silica (0-30% ethyl acetate/petroleum ether) to afford (S)-methyl 2-((methoxycarbonyl)amino)-3-(4-(trifluoromethyl)phenyl)propanoate as an oil. MS: 306 (M+1).

Step 3: To a solution of (S)-methyl 2-((methoxycarbonyl)amino)-3-(4-(trifluoromethyl)phenyl)propanoate (300 mg, 0.983 mmol) in acetic acid/sulfuric acid (3:1, v/v, 4 mL) was added paraformaldehyde (35 mg, 0.983 mmol). The mixture was stirred at 28° C. for 1.5 h. The mixture was poured into ice water (20 mL) and diluted with EtOAc (10 mL). The mixture was extracted with EtOAc (4×10 mL). The combined organic layers were washed with saturated aqueous sodium bicarbonate (40 mL), brine (20 mL), dried over anhydrous sodium sulfate, filtered, and concentrated under reduced pressure. The residue was purified by reverse phase HPLC (ACN/water with 0.1% TFA modifier) to afford (S)-dimethyl 7-(trifluoromethyl)-3,4-dihydroisoquinoline-2,3(1H)-dicarboxylate as a solid. MS: 318 (M+1).

Step 4: A mixture of (S)-dimethyl 7-(trifluoromethyl)-3,4-dihydroisoquinoline-2,3(1H)-dicarboxylate (9.98 g, 31.5 mmol) in concentrated HCl (50 mL) and hydrobromic acid in acetic acid (33~40%, 50 mL) was stirred at 110° C. for 15 h. The mixture was concentrated under reduced pressure to afford (S)-7-(trifluoromethyl)-1,2,3,4-tetrahydroisoquinoline-3-carboxylic acid as a solid which was used directly in next step without further purification. MS: 246 (M+1).

Step 5: To a solution of (S)-7-(trifluoromethyl)-1,2,3,4-tetrahydroisoquinoline-3-carboxylic acid (5 g, 20.4 mmol) in 1,4-dioxane (10 mL) and water (5 mL) was added sodium carbonate (4.3 g, 41 mmol) slowly. Di-tert-butyl dicarbonate (14 mL, 61 mmol) was added and the reaction was stirred at 25° C. for 1 h. The mixture was concentrated under reduced pressure, and the residue was quenched with water (100 mL). This mixture was diluted with tert-butyl methyl ether (100 mL), and the aqueous layer was acidified to pH ~3 with citric acid. The mixture was extracted with EtOAc (2×100 mL), and the combined organic layers were dried over anhydrous sodium sulfate, filtered, and concentrated under reduced pressure to afford (S)-2-(tert-butoxycarbonyl)-7-(trifluoromethyl)-1,2,3,4-tetrahydroisoquinoline-3-carboxylic acid as an oil which was used directly in next step without further purification. MS: 246 (M-Boc+H).

Step 6: To a solution of (S)-2-(tert-butoxycarbonyl)-7-(trifluoromethyl)-1,2,3,4-tetrahydroisoquinoline-3-carboxylic acid (500 mg, 1.448 mmol) in toluene (10 mL) and THF (2 mL) was added (trimethylsilyl)diazomethane (1.74 mL, 3.48 mmol) slowly at 25° C. The mixture was stirred at 25° C. for 5 min. To the mixture was added AcOH (6 mL) slowly. The mixture was concentrated under reduced pressure to give (S)-2-tert-butyl 3-methyl 7-(trifluoromethyl)-3,4-dihydroisoquinoline-2,3(1H)-dicarboxylate as an oil which was used directly in next step.

Step 7: To a solution of (S)-2-tert-butyl 3-methyl 7-(trifluoromethyl)-3,4-dihydroisoquinoline-2,3(1H)-dicarboxylate (520 mg, 1.45 mmol) in THF (6 mL) was added lithium borohydride (126 mg, 5.79 mmol). The reaction was stirred at 25° C. for 15 h, and the mixture was quenched with water (20 mL) slowly. The mixture was extracted with EtOAc (3×20 mL), and the combined organic layers were washed with brine (30 mL), dried over anhydrous sodium sulfate, filtered, and concentrated under reduced pressure. The residue was purified by column chromatography on silica (0-30% ethyl acetate/petroleum ether) to afford (S)-tert-butyl 3-(hydroxymethyl)-7-(trifluoromethyl)-3,4-dihydroisoquinoline-2(1H)-carboxylate as an oil. MS: 276 (M-tBu+H).

Step 8: To a solution of oxalyl chloride (0.093 mL, 1.1 mmol) in DCM (3 mL) was added DMSO (0.154 mL, 2.17 mmol) in DCM (1 mL) at −78° C. The mixture was stirred at −78° C. for 30 min, then (S)-tert-butyl 3-(hydroxymethyl)-7-(trifluoromethyl)-3,4-dihydroisoquinoline-2(1H)-carboxylate (200 mg, 0.604 mmol) in DCM (2 mL) was added at −78° C. The mixture was stirred at −78° C. for 30 min, then TEA (0.606 mL, 4.35 mmol) was added at −78° C. The mixture was stirred at −78° C. for 20 min. The mixture was quenched with water (20 mL) and extracted with DCM (3×20 mL). The combined organic layers were washed with HCl (0.1 M in water), washed with brine (20 mL), dried over anhydrous sodium sulfate, filtered, and concentrated under reduced pressure to afford (S)-tert-butyl 3-formyl-7-(trifluoromethyl)-3,4-dihydroisoquinoline-2(1H)-carboxylate as an oil which was used directly in next step without further purification.

Step 9: To a solution of (S)-tert-butyl 3-formyl-7-(trifluoromethyl)-3,4-dihydroisoquinoline-2(1H)-carboxylate (150 mg, 0.455 mmol) in ethanol (3 mL) was added (1R,2R)—N1,N2-bis(4-chlorobenzyl)cyclohexane-1,2-diamine Copper(II) acetate complex (49 mg, 0.091 mmol) in ethanol (2 mL). The solution was cooled to 0° C. and nitromethane (280 mg, 4.6 mmol) was added. The reaction mixture was stirred at 25° C. for 48 h. The mixture was concentrated under reduced pressure, and the residue was purified by prep-TLC (1:3 ethyl acetate/petroleum ether, $R_f$=0.3) to afford (S)-tert-butyl 3-((R)-1-hydroxy-2-nitroethyl)-7-(trifluoromethyl)-3,4-dihydroisoquinoline-2(1H)-carboxylate as an oil. MS: 335 (M-tBu+H).

Step 10: To a solution of (S)-tert-butyl 3-((R)-1-hydroxy-2-nitroethyl)-7-(trifluoromethyl)-3,4-dihydroisoquinoline-2(1H)-carboxylate (90 mg, 0.23 mmol) in ethanol (20 mL) was added Raney nickel (100 mg, 1.70 mmol) under an atmosphere of nitrogen. The mixture was degassed and backfilled with hydrogen (3×), and the resulting mixture was stirred under hydrogen (15 psi) at 25° C. for 1 h. The mixture was filtered, and the filtrate was concentrated under reduced pressure to afford tert-butyl (3S)-3-[(1R)-2-amino-1-hydroxyethyl]-7-(trifluoromethyl)-3,4-dihydroisoquinoline-2(1H)-carboxylate as an oil which was used in next step without further purification. MS: 305 (M-tBu+H).

Intermediate 10 (see Scheme X, Compound B43)

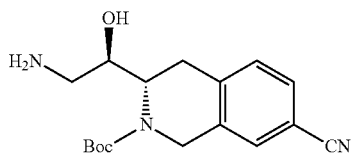 [SMILES: CC(C)(C)OC(=O)N1Cc2cc(C#N)ccc2C[C@H]1[C@H](O)CN]

tert-butyl (3S)-3-[(1R)-2-amino-1-hydroxyethyl]-7-cyano-3,4-dihydroisoquinoline-2(1H)-carboxylate Step 1: To a mixture of (S)-7-bromo-10,10a-dihydro-1H-oxazolo[3,4-b]isoquinolin-3(5H)-one (200 mg, 0.75 mmol) and dicyanozinc (438 mg, 3.73 mmol) in DMF (5 mL) was added Pd(PPh$_3$)$_4$ (172 mg, 0.149 mmol) at 25° C. The mixture was degassed and backfilled with nitrogen (3×), and stirred at 80° C. for 15 h under an atmosphere of nitrogen. The mixture was cooled to room temperature, quenched with water (50 mL), and extracted with EtOAc (3×20 mL). The combined organic layers were washed with brine (40 mL), dried over anhydrous sodium sulfate, filtered, and concentrated under reduced pressure. The residue was purified by prep-TLC (2:1 ethyl acetate/petroleum ether, $R_f$=0.3) to afford (S)-3-oxo-3,5,10,10a-tetrahydro-1H-oxazolo[3,4-b]isoquinoline-7-carbonitrile as a solid. MS: 215 (M+1).

Step 2: To a solution of (S)-3-oxo-3,5,10,10a-tetrahydro-1H-oxazolo[3,4-b]isoquinoline-7-carbonitrile (2 g, 9.3 mmol) in THF (100 mL) was added sodium hydroxide (2M in water, 187 mL, 373 mmol). The reaction mixture was stirred at 25° C. for 12 h to afford (S)-3-(hydroxymethyl)-1,2,3,4-tetrahydroisoquinoline-7-carbonitrile. The reaction was used directly in next step. MS: 189 (M+1).

Step 3: To the solution of (S)-3-(hydroxymethyl)-1,2,3,4-tetrahydroisoquinoline-7-carbonitrile (2 g, 10.6 mmol) in THF (100 mL) and sodium hydroxide (2M in water, 187 mL, 373 mmol) obtained in step 2 was added di-tert-butyl dicarbonate (6.2 mL, 27 mmol). The mixture was stirred at 25° C. for 1 h and then extracted with EtOAc (3×50 mL). The combined organic layers were washed with brine (50 mL), dried over anhydrous sodium sulfate, filtered and concentrated under reduced pressure. The residue was purified by column chromatography on silica (0-50% ethyl acetate/petroleum ether) to afford (S)-tert-butyl 7-cyano-3-(hydroxymethyl)-3,4-dihydroisoquinoline-2(1H)-carboxylate as an oil. MS: 189 (M-Boc+H).

Step 4: To a stirred solution of oxalyl chloride (0.13 mL, 1.5 mmol) in DCM (3 mL) was added DMSO (0.213 mL, 3.00 mmol) in DCM (1 mL) at −78° C. The solution was stirred at −78° C. for 0.5 h, and (S)-tert-butyl 7-cyano-3-(hydroxymethyl)-3,4-dihydroisoquinoline-2(1H)-carboxylate (240 mg, 0.83 mmol) in DCM (1 mL) was added dropwise. The solution was stirred at −78° C. for 0.5 h, and TEA (0.84 mL, 6 mmol) was added dropwise. The solution was stirred at −78° C. for 0.5 h, and then slowly warmed to room temperature and stirred for 0.5 h. The mixture was quenched with water (30 mL) and extracted with DCM (2×20 mL). The combined organic layers were washed with HCl (0.25 M in water, 20 mL×2), dried over sodium sulfate, filtered, and concentrated under reduced pressure to afford (S)-tert-butyl 7-cyano-3-formyl-3,4-dihydroisoquinoline-2(1H)-carboxylate as an oil which was used directly in the next step without further purification.

Step 5: To a solution of (S)-tert-butyl 7-cyano-3-formyl-3,4-dihydroisoquinoline-2(1H)-carboxylate (240 mg, 0.84 mmol) in ethanol (3 mL) was added (1R,2R)—N1,N2-bis(4-chlorobenzyl)cyclohexane-1,2-diamine copper(II) acetate complex (91 mg, 0.17 mmol) in ethanol (1 mL). The solution was cooled to 0° C., and nitromethane (512 mg, 8.38 mmol) was added. The reaction was stirred at 25° C. for 48 h, and the mixture was concentrated under reduced pressure. The residue was purified by prep-TLC (1:3 ethyl acetate/petroleum ether, $R_f$=0.3) to afford (S)-tert-butyl 7-cyano-3-((R)-1-hydroxy-2-nitroethyl)-3,4-dihydroisoquinoline-2(1H)-carboxylate as an oil.

Step 6: To a solution of (S)-tert-butyl 7-cyano-3-((R)-1-hydroxy-2-nitroethyl)-3,4-dihydroisoquinoline-2(1H)-carboxylate (110 mg, 0.32 mmol) in AcOH (10 mL) was added zinc (207 mg, 3.17 mmol). The mixture was stirred at 25° C. for 12 h. More zinc (207 mg, 3.17 mmol) was added, and the mixture was stirred at 25° C. for 12 h. The mixture was poured into saturated aqueous sodium bicarbonate (200 mL), and the mixture was extracted with EtOAc (3×100 mL). The combined organic layers were washed with brine (150 mL), dried over anhydrous sodium sulfate, filtered, and concentrated under reduced pressure to afford tert-butyl (3S)-3-[(1R)-2-amino-1-hydroxyethyl]-7-cyano-3,4-dihydroisoquinoline-2(1H)-carboxylate as an oil which was used directly in next step without further purification. MS: 318 (M+1).

Intermediate 11 (see Scheme VI, Compound B16)

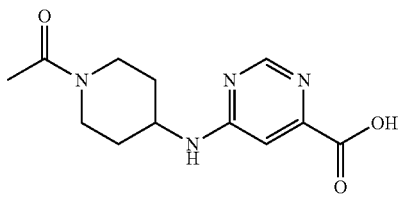 [SMILES: CC(=O)N1CCC(Nc2cc(C(=O)O)ncn2)CC1]

6-((1-acetylpiperidin-4-yl)amino)pyrimidine-4-carboxylic acid

Step 1: To a solution of tert-butyl piperidin-4-ylcarbamate (10 g, 50 mmol) and TEA (10 mL, 775 mmol) in DCM (50 mL) was added acetic anhydride (5.1 g, 50 mmol) at 0° C. The resulting mixture was stirred at 0° C. for 1.5 h. The reaction was quenched with water (30 mL), and the organic layer was washed with saturated aqueous sodium bicarbonate (50 mL), dried over anhydrous sodium sulfate, filtered, and concentrated under reduced pressure to afford tert-butyl (1-acetylpiperidin-4-yl)carbamate as a solid, which was used in next step without further purification.

Step 2: To a solution of tert-butyl (1-acetylpiperidin-4-yl)carbamate (13 g, 55 mmol) was added TFA (24 mL, 312 mmol) in DCM (25 mL). The mixture was stirred at 20° C. for 30 min. The reaction was concentrated under reduced pressure to afford 1-(4-aminopiperidin-1-yl)ethanone, TFA as a solid, which was used in next step without further purification.

Step 3: To a solution of 1-(4-aminopiperidin-1-yl)ethanone, TFA (24 g, 134 mmol) in 2-propanol (80 mL) was added DIEA (23.4 mL, 134 mmol) and 4,6-dichloropyrimidine (20 g, 134 mmol). The mixture was stirred at 100° C. for 4 h under an atmosphere of nitrogen. The mixture was concentrated under reduced pressure and the residue was dissolved in water (60 mL). The aqueous layer was extracted with EtOAc (3×80 mL), and the combined organic layers were washed with brine (60 mL), dried over anhydrous sodium sulfate, filtered, and concentrated under reduced pressure. The residue was purified by column chromatography on silica (100% ethyl acetate) to afford 1-(4-((6-chloropyrimidin-4-yl)amino)piperidin-1-yl)ethanone as an oil.

Step 4: To a solution of 1-(4-((6-chloropyrimidin-4-yl)amino)piperidin-1-yl)ethanone (10 g, 39 mmol) and potassium acetate (11.6 g, 118 mmol) in ethanol (90 mL) was added PdCl$_2$(dppf) (2.9 g, 3.9 mmol). The mixture was degassed and backfilled with CO (3×), and the resulting mixture was stirred under CO (50 psi) at 70° C. for 16 h. The mixture was concentrated under reduced pressure, and the residue was purified by column chromatography on silica (0-5% ethyl acetate/MeOH) to afford ethyl 6-((1-acetylpiperidin-4-yl)amino)pyrimidine-4-carboxylate as an oil. MS: 293 (M+1).

Step 5: To a solution of ethyl 6-((1-acetylpiperidin-4-yl)amino)pyrimidine-4-carboxylate (7.5 g, 26 mmol) in MeOH (60 mL) and water (5 mL) was added lithium hydroxide hydrate (1.4 g, 33 mmol). The mixture was stirred at 20° C. for 1.5 h. The mixture was acidified by adding HCl (12 N in water, 2 mL), and the mixture was concentrated under reduced pressure to afford 6-((1-acetylpiperidin-4-yl)amino)pyrimidine-4-carboxylic acid as a solid, which was used in next step without further purification. MS: 265 (M+1).

Intermediate 12 (see Scheme VII, Compound B22)

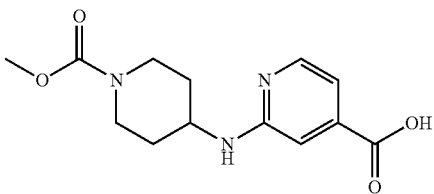 [SMILES: COC(=O)N1CCC(Nc2cc(C(=O)O)ccn2)CC1]

2-{[1-(methoxycarbonyl)piperidin-4-yl]amino}pyridine-4-carboxylic acid

Step 1: To a solution of tert-butyl 4-aminopiperidine-1-carboxylate (500 mg, 2.5 mmol) in toluene (20 mL) was added palladium(II) acetate (56 mg, 0.25 mmol), cesium carbonate (1.06 g, 3.25 mmol), 2,2'-bis(diphenylphosphino)-1,1'-binaphthalene (155 mg, 0.250 mmol), and methyl 2-chloroisonicotinate (386 mg, 2.25 mmol). The mixture was placed under an atmosphere of nitrogen by degassing and backfilling with nitrogen (3×). The reaction mixture was stirred at 90° C. for 10 h. The mixture was diluted with water (50 mL) and extracted with DCM (3×30 mL). The combined organic layers were dried over anhydrous sodium sulfate, filtered, and concentrated under reduced pressure. The residue was purified by column chromatography on silica (0-50% ethyl acetate/petroleum ether) to afford methyl 2-((1-(tert-butoxycarbonyl)piperidin-4-yl)amino)isonicotinate as a solid. MS: 336 (M+1).

Step 2: A solution of methyl 2-((1-(tert-butoxycarbonyl)piperidin-4-yl)amino)isonicotinate (460 mg, 1.37 mmol) in HCl (4 M in MeOH, 20 mL) was stirred for 2 h at 20° C. The mixture was concentrated under reduced pressure to afford methyl 2-(piperidin-4-ylamino)isonicotinate dihydrochloride as a solid which was used directly in next step without further purification. MS: 236 (M+1).

Step 3: To a solution of methyl 2-(piperidin-4-ylamino)isonicotinate dihydrochloride (351 mg, 1.14 mmol) in DCM (20 mL) at 0° C. was added 2,5-dioxopyrrolidin-1-yl methyl carbonate (237 mg, 1.37 mmol) and DIEA (589 mg, 4.56 mmol). The reaction mixture was stirred at 20° C. for 2 h. The mixture was concentrated under reduced pressure and the residue was purified by column chromatography on silica (0-50% ethyl acetate/petroleum ether) to afford methyl 2-((1-(methoxycarbonyl)piperidin-4-yl)amino)isonicotinate as a solid. MS: 294 (M+1).

Step 4: To a solution of methyl 2-((1-(methoxycarbonyl)piperidin-4-yl)amino)isonicotinate (280 mg, 0.96 mmol) in THF (2 mL), MeOH (2 mL) and water (2 mL) was added lithium hydroxide (34 mg, 1.4 mmol) at 0° C. The reaction mixture was stirred at 20° C. for 2 h. Added HCl (1 M in water) to ~pH 3, and the mixture was concentrated under reduced pressure to afford 2-{[1-(methoxycarbonyl)piperidin-4-yl]amino}pyridine-4-carboxylic acid as a solid, which was used in next step without further purification. MS: 280 (M+1).

Intermediate 13 (see Scheme I, Compound H3)

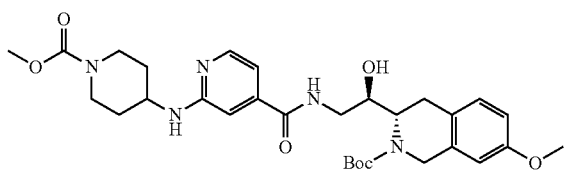

tert-butyl (3S)-3-[(1R)-1-hydroxy-2-{[(2-{[1-(methoxycarbonyl)piperidin-4-yl]amino}pyridin-4-yl)carbonyl]amino}ethyl]-7-methoxy-3,4-dihydroisoquinoline-2(1H)-carboxylate To a mixture of (S)-tert-butyl 3-((R)-2-amino-1-hydroxyethyl)-6-methoxy-3,4-dihydroisoquinoline-2(1H)-carboxylate (60 mg, 0.19 mmol) in DMF (2 mL) was added 2-((1-(methoxycarbonyl)piperidin-4-yl)amino)isonicotinic acid (87 mg, 0.31 mmol), 2,4,6-tributyl-1,3,5,2,4,6-trioxatriphosphinane 2,4,6-trioxide (298 mg, 0.414 mmol) and DIEA (94 mg, 0.72 mmol). The reaction mixture was stirred at 25° C. for 1 h. The residue was purified by reverse phase HPLC (ACN/water with 0.1% TFA modifier) to afford tert-butyl (3S)-3-[(1R)-1-hydroxy-2-{[(2-{[1-(methoxycarbonyl)piperidin-4-yl]amino}pyridin-4-yl)carbonyl]amino}ethyl]-7-methoxy-3,4-dihydroisoquinoline-2(1H)-carboxylate as a solid. MS: 584 (M+1).

Example 4

N—((R)-2-hydroxy-2-((S)-7-methoxy-1,2,3,4-tetrahydroisoquinolin-3-yl)ethyl)-6-(oxetan-3-ylamino)pyrimidine-4-carboxamide

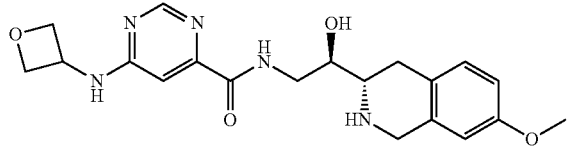 [SMILES: COc1ccc2c(c1)CN[C@H]([C@H](O)CNC(=O)c1cc(NC3COC3)ncn1)C2]

See Scheme VIII

Step 1: To a solution of 6-chloropyrimidine-4-carboxylic acid (29.5 mg, 0.186 mmol), HATU (78 mg, 0.21 mmol) and DIEA (0.217 mL, 1.24 mmol) in DCM (2 mL) was added (S)-tert-butyl 3-((R)-2-amino-1-hydroxyethyl)-7-methoxy-3,4-dihydroisoquinoline-2(1H)-carboxylate A10 (50 mg, 0.16 mmol). The mixture was stirred at 25° C. for 5 min. The reaction was purified by prep-TLC (1:2 ethyl acetate/petroleum ether, $R_f$=0.2) to afford (S)-tert-butyl 3-((R)-2-(6-chloropyrimidine-4-carboxamido)-1-hydroxyethyl)-7-methoxy-3,4-dihydroisoquinoline-2(1H)-carboxylate as a solid which was used in next step without further purification. MS: 485 (M+Na).

Step 2: A mixture of (S)-tert-butyl 3-((R)-2-(6-chloropyrimidine-4-carboxamido)-1-hydroxyethyl)-7-methoxy-3,4-dihydroisoquinoline-2(1H)-carboxylate (30 mg, 0.065 mmol) in HCl (4 M in dioxane, 5 mL) was stirred at 25° C. for 30 min. The mixture was concentrated under reduced pressure to afford 6-chloro-N—((R)-2-hydroxy-2-((S)-7-methoxy-1,2,3,4-tetrahydroisoquinolin-3-yl)ethyl)pyrimidine-4-carboxamide as a solid, which was used in next step without further purification.

Step 3: To a solution of 6-chloro-N—((R)-2-hydroxy-2-((S)-7-methoxy-1,2,3,4-tetrahydroisoquinolin-3-yl)ethyl)pyrimidine-4-carboxamide (86 mg, 0.24 mmol) in DCM (5 mL) was added TEA (0.1 mL, 0.7 mmol) and (9H-fluoren-9-yl)methyl (2,5-dioxopyrrolidin-1-yl) carbonate (160 mg, 0.474 mmol). The mixture was stirred at 25° C. for 30 min. The mixture was concentrated under reduced pressure, and the residue was purified by prep-TLC (1:1 ethyl acetate/petroleum ether, $R_f$=0.3) to afford (S)-(9H-fluoren-9-yl)methyl 3-((R)-2-(6-chloropyrimidine-4-carboxamido)-1-hydroxyethyl)-7-methoxy-3,4-dihydroisoquinoline-2(1H)-carboxylate as a solid. MS: 607 (M+Na).

Step 4: To a solution of (S)-(9H-fluoren-9-yl)methyl 3-((R)-2-(6-chloropyrimidine-4-carboxamido)-1-hydroxyethyl)-7-methoxy-3,4-dihydroisoquinoline-2(1H)-carboxylate (50 mg, 0.085 mmol) and DIEA (0.090 mL, 0.51 mmol) in isopropanol (5 mL) was added oxetan-3-amine (62.5 mg, 0.855 mmol). The mixture was stirred at 110° C. for 4 h. The mixture was concentrated under reduced pressure, and the residue was purified by reverse phase HPLC (ACN/water with 0.05% ammonia hydroxide modifier) to afford N—((R)-2-hydroxy-2-((S)-7-methoxy-1,2,3,4-tetrahydroisoquinolin-3-yl)ethyl)-6-(oxetan-3-ylamino)pyrimidine-4-carboxamide as a solid. MS: 400 (M+1). $^1$H NMR (400 MHz, DMSO-$d_6$) δ 8.69 (m, 1H), 8.56-8.44 (m, 2H), 7.12 (br s, 1H), 6.98 (d, J=8.16 Hz, 1H), 6.68 (m, 1H), 6.59 (s, 1H), 5.13-4.94 (m, 2H), 4.82 (t, J=6.62 Hz, 2H), 4.46 (m, 2H), 4.10-3.99 (m, 1H), 3.90-3.75 (m, 2H), 3.68 (s, 3H), 3.67-3.52 (m, 3H), 2.76-2.57 (m, 2H), 2.33 (br s, 1H).

Example 5

2-ethoxy-N-{(2R)-2-hydroxy-2-[(3S)-7-methoxy-1,2,3,4-tetrahydroisoquinolin-3-yl]ethyl}-4-(5-methyl-1,3,4-oxadiazol-2-yl)benzamide

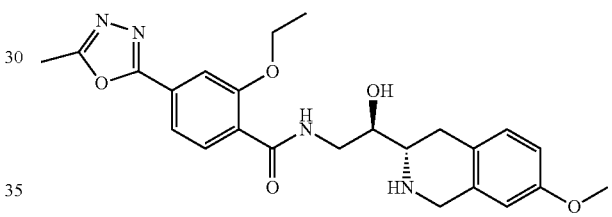

Step 1: To a solution of 2-ethoxy-4-(5-methyl-1,3,4-oxadiazol-2-yl)benzoic acid (Intermediate 8) (50 mg, 0.20 mmol) in DCM (2 mL) was added HATU (89 mg, 0.23 mmol) and DIEA (0.03 mL, 0.2 mmol). The reaction mixture was stirred at 30° C. for 5 min. (S)-tert-butyl 3-((R)-2-amino-1-hydroxyethyl)-7-methoxy-3,4-dihydroisoquinoline-2(1H)-carboxylate A10 (60 mg, 0.186 mmol) was added to the mixture, and the reaction was stirred at 30° C. for 2 h. The mixture was purified by prep-TLC (1:4 ethyl acetate/petroleum ether) to afford (S)-tert-butyl 3-((R)-2-(2-ethoxy-4-(5-methyl-1,3,4-oxadiazol-2-yl)benzamido)-1-hydroxyethyl)-7-methoxy-3,4-dihydroisoquinoline-2(1H)-carboxylate as an oil. MS: 553 (M+1).

Step 2: To a solution of (S)-tert-butyl 3-((R)-2-(2-ethoxy-4-(5-methyl-1,3,4-oxadiazol-2-yl)benzamido)-1-hydroxyethyl)-7-methoxy-3,4-dihydroisoquinoline-2(1H)-carboxylate (45 mg, 0.08 mmol) in EtOAc (1 mL) was added HCl (4M in EtOAc, 4 mL). The reaction was stirred at 26° C. for 2 h. The mixture was concentrated under reduced pressure, and the residue was purified by reverse phase HPLC (ACN/water with 10 mM NH$_4$HCO$_3$ modifier) to afford 2-ethoxy-N-{(2R)-2-hydroxy-2-[(3S)-7-methoxy-1,2,3,4-tetrahydroisoquinolin-3-yl]ethyl}-4-(5-methyl-1,3,4-oxadiazol-2-yl)benzamide as a solid. MS: 453 (M+1). $^1$H NMR (400 MHz, CD$_3$OD) δ 8.06 (d, J=8.0 Hz, 1H), 7.69 (s, 1H), 7.65 (d, J=8.0 Hz, 1H), 7.01 (d, J=8.4 Hz, 1H), 6.78 (dd, J=1.6, 8.8 Hz, 1H), 6.59 (s, 1H), 4.28 (q, J=6.8 Hz, 2H), 4.05-3.92 (m, 2H), 3.89-3.80 (m, 1H), 3.79-3.68 (m, 4H), 3.60-3.45 (m, 1H), 2.99-2.89 (m, 1H), 2.87-2.07 (m, 2H), 2.61 (s, 3H), 1.48 (t, J=7.04 Hz, 3H).

Example 6

4-(5-cyclopropyl-1,3,4-oxadiazol-2-yl)-2-ethoxy-N-{(2R)-2-hydroxy-2-[(3S)-7-methoxy-1,2,3,4-tetrahydroisoquinolin-3-yl]ethyl}benzamide

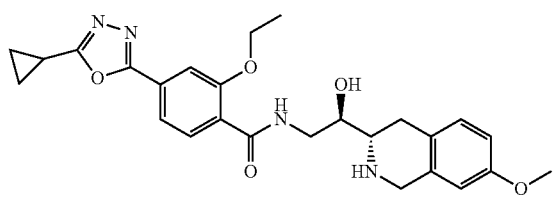 [SMILES: CCOc1cc(-c2nnc(C3CC3)o2)ccc1C(=O)NC[C@@H](O)[C@@H]1Cc2ccc(OC)cc2CN1]

Step 1: To a solution of 4-(5-cyclopropyl-1,3,4-oxadiazol-2-yl)-2-ethoxybenzoic acid (Intermediate 2) (70 mg, 0.26 mmol) and HATU (126 mg, 0.33 mmol) in DCM (3 mL) was added DIEA (99 mg, 0.77 mmol) and (S)-tert-butyl 3-((R)-2-amino-1-hydroxyethyl)-7-methoxy-3,4-dihydroisoquinoline-2(1H)-carboxylate A10 (90 mg, 0.28 mmol). The reaction was stirred at 28° C. for 1 h. The mixture was dissolved in water (20 mL), and extracted with DCM (2×10 mL). The combined organic layers were dried over anhydrous sodium sulfate, filtered, and concentrated under reduced pressure. The residue was purified by reverse phase HPLC (ACN/water with 0.1% TFA modifier) to afford (S)-tert-butyl 3-((R)-2-(4-(5-cyclopropyl-1,3,4-oxadiazol-2-yl)-2-ethoxybenzamido)-1-hydroxyethyl)-7-methoxy-3,4-dihydroisoquinoline-2(1H)-carboxylate, TFA as solid. MS: 579 (M+1).

Step 2: To a solution of (S)-tert-butyl 3-((R)-2-(4-(5-cyclopropyl-1,3,4-oxadiazol-2-yl)-2-ethoxybenzamido)-1-hydroxyethyl)-7-methoxy-3,4-dihydroisoquinoline-2(1H)-carboxylate (100 mg, 0.173 mmol) in DCM (3 mL) was added TFA (0.5 mL, 6.5 mmol). The mixture was stirred at 25° C. for 1 h. The solution was concentrated under reduced pressure, and the residue was purified by reverse phase HPLC (ACN/water with 10 mM $NH_4HCO_3$ modifier) to afford 4-(5-cyclopropyl-1,3,4-oxadiazol-2-yl)-2-ethoxy-N-{(2R)-2-hydroxy-2-[(3S)-7-methoxy-1,2,3,4-tetrahydroisoquinolin-3-yl]ethyl}benzamide as a solid. MS: 479 (M+1). $^1$H NMR (400 MHz, $CDCl_3$) δ=8.52 (m, 1H), 8.27 (d, J=8.2 Hz, 1H), 7.65 (d, J=1.2 Hz, 1H), 7.57 (dd, J=1.5, 8.1 Hz, 1H), 7.02 (d, J=8.4 Hz, 1H), 6.71 (dd, J=2.4, 8.4 Hz, 1H), 6.52 (d, J=2.3 Hz, 1H), 4.28 (q, J=6.8 Hz, 2H), 4.09-3.94 (m, 2H), 3.93-3.78 (m, 2H), 3.75 (s, 3H), 3.64-3.51 (m, 1H), 3.02 (m, 1H), 2.84-2.70 (m, 2H), 2.30-2.16 (m, 1H), 1.54 (t, J=6.8 Hz, 3H), 1.27-1.12 (m, 4H).

The compounds in the following table were prepared using the methodology herein and the general procedure described in Examples 5 and 6

| Ex. No. | Structure and Chemical Name | [M + H]⁺ | Amide Coupling | Deprotection |
|---|---|---|---|---|
| 7 | 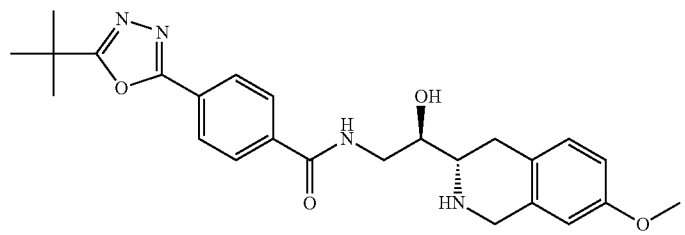<br>4-(5-tert-butyl-1,3,4-oxadiazol-2-yl)-N-{(2R)-2-hydroxy-2-[(3S)-7-methoxy-1,2,3,4-tetrahydroisoquinolin-3-yl]ethyl}benzamide | 451 | HATU | HCl |
| 8 | 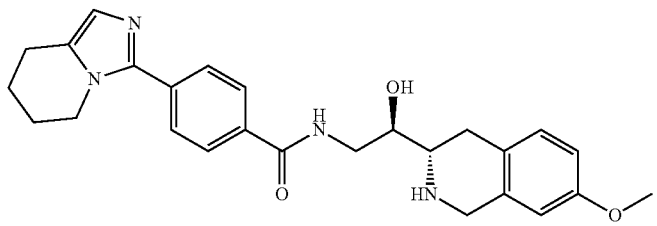<br>N-{(2R)-2-hydroxy-2-[(3S)-7-methoxy-1,2,3,4-tetrahydroisoquinolin-3-yl]ethyl}-4-(5,6,7,8-tetrahydroimidazo[1,5-a]pyridin-3-yl)benzamide | 447 | HATU | TFA |

| Ex. No. | Structure and Chemical Name | [M + H]⁺ | Amide Coupling | Deprotection |
|---|---|---|---|---|
| 9 | 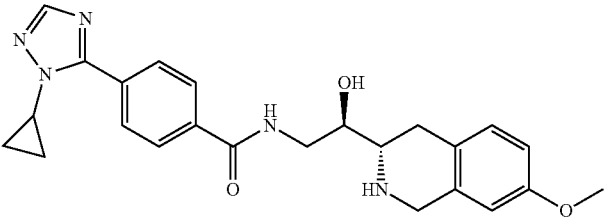4-(1-cyclopropyl-1H-1,2,4-triazol-5-yl)-N-{(2R)-2-hydroxy-2-[(3S)-7-methoxy-1,2,3,4-tetrahydroisoquinolin-3-yl]ethyl}benzamide | 434 | HATU | HCl |
| 10 | 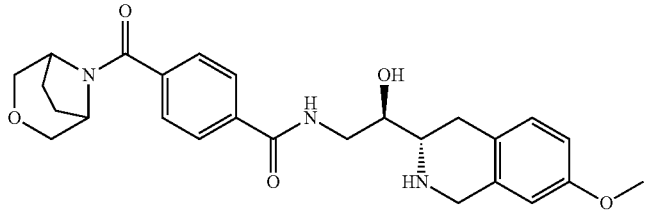N-{(2R)-2-[(3S)-7-ethyl-1,2,3,4-tetrahydroisoquinolin-3-yl]-2-hydroxyethyl}-4-(3-oxa-8-azabicyclo[3.2.1]oct-8-ylcarbonyl)benzamide | 464 | HATU | HCl |
| 11 | 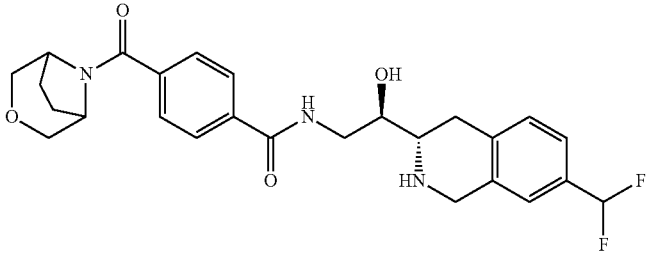N-{(2R)-2-[(3S)-7-(difluroomethyl)-1,2,3,4-tetrahydroisoquinolin-3-yl]-2-hydroxyethyl}-4-(3-oxa-8-azabicyclo[3.2.1]oct-8-ylcarbonyl)benzamide | 486 | T3P | HCl |
| 12 | 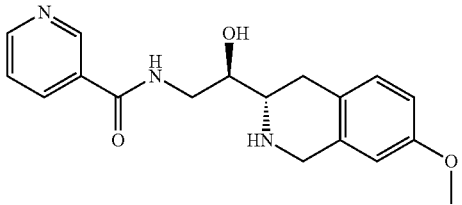N-{(2R)-2-hydroxy-2-[(3S)-7-methoxy-1,2,3,4-tetrahydroisoquinolin-3-yl]ethyl}pyridine-3-carboxamide | 328 | T3P | HCl |

| Ex. No. | Structure and Chemical Name | [M + H]⁺ | Amide Coupling | Deprotection |
|---|---|---|---|---|
| 13 | 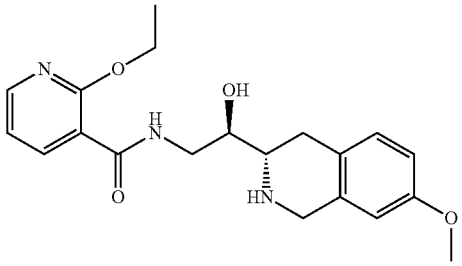<br>2-ethoxy-N-{(2R)-2-hydroxy-2-[(3S)-7-methoxy-1,2,3,4-tetrahydroisoquinolin-3-yl]ethyl}pyridine-3-carboxamide | 372 | T3P | HCl |
| 14 | 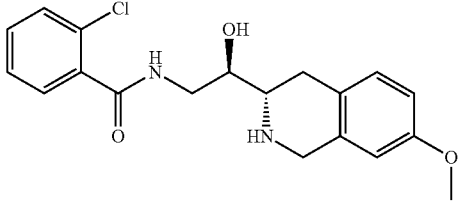<br>2-chloro-N-{(2R)-2-hydroxy-2-[(3S)-7-methoxy-1,2,3,4-tetrahydroisoquinolin-3-yl]ethyl}benzamide | 361 | T3P | HCl |
| 15 | 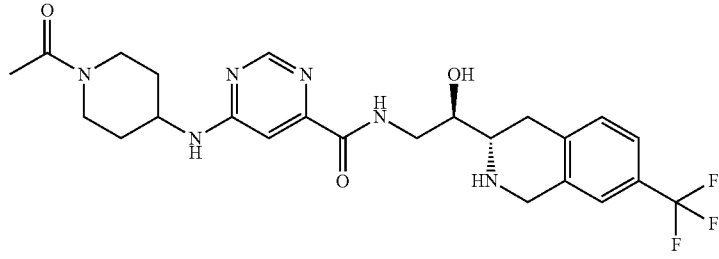<br>6-[(1-acetylpiperidin-4-yl)amino]-N-{(2R)-2-hydroxy-2-[(3S)-7-(trifluoromethyl)-1,2,3,4-tetrahydroisoquinolin-3-yl]ethyl}pyrimidine-4-carboxamide | 507 | HATU | HCl |
| 16 | 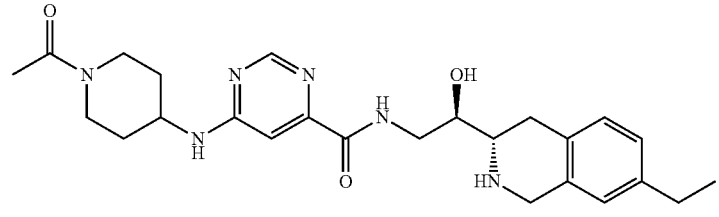<br>6-[(1-acetylpiperidin-4-yl)amino]-N-{(2R)-2-[(3S)-7-ethyl-1,2,3,4-tetrahydroisoquinolin-3-yl]-2-hydroxyethyl}pyrimidine-4-carboxamide | 467 | T3P | HCl |

| Ex. No. | Structure and Chemical Name | [M + H]+ | Amide Coupling | Deprotection |
|---|---|---|---|---|
| 17 | 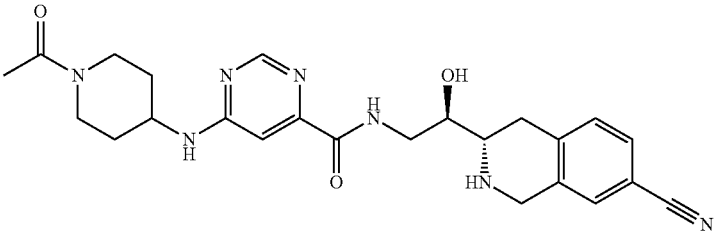<br>6-[(1-acetylpiperidin-4-yl)amino]-N-{(2R)-2-[(3S)-7-cyano-1,2,3,4-tetrahydroisoquinolin-3-yl]-2-hydroxyethyl}pyrimidine-4-carboxamide | 464 | T3P | HCl |
| 18 | 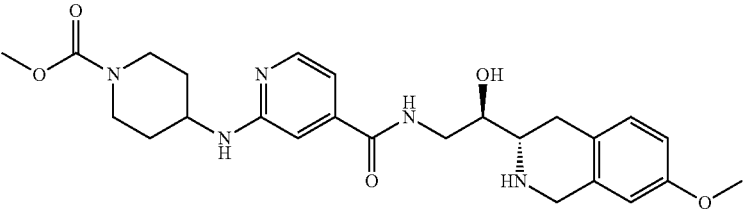<br>methyl 4-{[4-({(2R)-2-hydroxy-2-[(3S)-7-methoxy-1,2,3,4-tetrahydroisoquinolin-3-yl]ethyl}carbamoyl)pyridin-2-yl]amino}piperidine-1-carboxylate | 484 | T3P | HCl |

Assays

PRMT5 Biochemical Assay

Compounds of the Invention may be Tested for In Vitro Activity in the Following Assay:

A histone H4 derived peptide is used as substrate (amino acid sequence: Ser-Gly-Arg-Gly-Lys-Gly-Gly-Lys-Gly-Leu-Gly-Lys-Gly-Gly-Ala-Lys-Arg-His-Arg-Lys-Val-NH$_2$). Full-length PRMT5 enzyme (NCBI Reference sequence NP_006100.2) was co-expressed with His$_6$-MEP50 in insect cells and purified via Nickel immobilized metal affinity and gel filtration chromatography ("the enzyme").

The 6 µL reactions are run in Greiner brand black 384-well low volume assay plates. All reactions contained assay buffer (phosphate buffered saline, 0.01% (v/v) Tween-20, 0.01% (w/v) albumin from chicken egg white, 1 mM Dithiothreitol, 1 µM peptide substrate, 1 µM S-Adenosyl methionine, and 15 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 4 hours at 37 degree Celsius. Reaction progress was measured using the Transcreener™ EPIGEN methyltransferase assay (Bell-Brook Labs, Madison, Wis.) as recommended by the manufacturer. To each reaction 2 µL detection mix were added, containing coupling enzymes, fluorescence polarisation tracer, and AMP antibody. Plates were incubated for 90 minutes before being read on a Perkin Elmer EnVision™ plate reader in fluorescence polarisation mode. IC$_{50}$ values were obtained from the raw readings by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the IC$_{50}$ value, and D is the slope.

| Example Number | IC$_{50}$ (µM) |
|---|---|
| 1 | 0.015 |
| 2 | 0.018 |
| 3 | 1.009 |

PRMT5 Biomarker Assay

Compounds of the Invention may be Tested for Potency to Inhibit Symmetrical Dimethylation of Arginine in the Following Assay:

The cell line TE11 was seeded at a density of 6,000 cells per well in 96 well optical quality tissue culture plates in DME medium and 10% foetal bovine serum, and allowed to adhere for 5 hours under standard culture conditions (37 degree Celsius, 5% CO$_2$). Compound dilutions prepared in DMSO were added to the medium, with negative control wells reserved for treatment with DMSO only and maximum inhibition controls receiving a potent PRMT5 inhibitor compound at 1 µM concentration. After incubation for 72 hours, the cells were fixed with 3.7% formaldehyde in PBS for 30 minutes at room temperature, washed with phosphate buffer saline and blocked with Odyssey blocking buffer (LI-COR, Lincoln, Nebr.). Rabbit anti-Di-Methyl Histone H4 Arginine 3 specific antibody (Epigentek) in Odyssey blocking buffer was added and incubated for 14 hours at 4 degree Celsius. After washing, anti-rabbit secondary antibody labelled with Alexa647 dye (LifeTechnologies) and Hoechst 33342 (1 μg/mL, SigmaAldrich) were added for 1 hour incubation. Plates were washed and read on a PerkinElmer Envision 2103 in fluorescence intensity scanning mode (24 scans across the well area). The plates were imaged on a PerkinElmer Phenix high content imaging platform. Using a Columbus image analysis pipeline, individual nuclei were located by Hoechst 33342 stain and the methylation level was calculated from the Alexa647-related intensity in the same area. $IC_{50}$ values were obtained from the mean Alexa647-related intensity per cell by calculating percent inhibition (% I) for each well relative to controls on the same plate (% I=(I−CN)/(CP−CN) where CN/CP are the averages of the negative/maximum inhibition controls, respectively), then fitting the % I data vs. compound concentration [I] to % I=(A+((B−A)/(1+((C/[I])^D)))) where A is the lower asymptote, B is the upper asymptote, C is the $IC_{50}$ value, and D is the slope.

| Example Number | $IC_{50}$ (μM) |
|---|---|
| 1 | 0.00019 |
| 2 | 0.00040 |
| 3 | 0.00712 |

PRMT5-MEP50 Enzyme Methylation Assay

PRMT5/MEP50 biochemical assay is a direct measurement of the methylation activity of the enzyme complex on a short peptide substrate derived from the N-terminus of H4 histone. Methylation experiment is performed with recombinant protein. The assessment of inhibitory effect ($IC_{50}$) of small molecules is measured by the effectiveness of the compounds to inhibit this reaction.

In this assay, the potency ($IC_{50}$) of each compound was determined from a twenty-point (1:2 serial dilution; top compound concentration of 100000 nM) titration curve using the following outlined procedure. To each well of a white ProxiPlus 384 well-plate, 100 nL of compound (1% DMSO in final assay volume of 10 μL) was dispensed, followed by the addition of 8 μL of 1× assay buffer (50 mM Bicine pH 8.0, 1 mM DTT, 0.004% Tween20, 0.01% BSA) containing 0.5 nM of Full-length (FL)-PRMT5-MEP50 enzyme complex (recombinant proteins from baculovirus-transfected Sf21 cells: FL-PRMT5; MW=73837 kDa and FL-MEP50; MW=38614). Plates were sealed and placed in a 37° C. humidified chamber for 30 minutes pre-incubation with compounds. Subsequently, each reaction was initiated by the addition of 2 μL 1× assay buffer containing 75 nM biotinylated H4R3(Me1) peptide, and 15 μM S-(5'-Adenosyl)-L-Methionine Chloride (SAM). The final reaction in each well of 10 μL consists of 0.5 nM PRMT5-MEP50,75 nM biotinylated-peptide, and 15 μM SAM. Methylation reactions were allowed to proceed for 150 minutes in a sealed plate at 37° C. Reactions were immediately quenched by the addition of 1 μL of 10% formic acid. Plates were then frozen and shipped to SAMDI™ Tech Inc. to determine the percent conversion from K4R3(Me1) to K4R3(Me2). $IC_{50}$ values were determined by 7 parameters biphasic fit model plotting the percent product conversion vs. ($Log_{10}$) compound concentrations.

PRMT5 Cell Target Engagement (TE) Assay

The PRMT5 TE assay is a biomarker assay for identifying compounds that inhibit symmetric dimethylation of arginine (SDMA) of PRMT5 substrates. This assay detects symmetrically dimethylated nuclear proteins using high content imaging technology. Detection of the expression of symmetrically dimethylated nucleo proteins is through a mixture of primary rabbit monoclonal antibodies to SDMA (CST 13222), which in turn recognized by an Alexafluor 488 dye-conjugated anti-rabbit IgG secondary antibody. The IN Cell Analyzer 2200 measures nuclear Alexafluor 488 fluorescent dye intensity that is directly related to the level of expression of symmetrically dimethylated nuclear proteins at the single cell level. Nuclear AF488 dye intensities are compared to the mean value for DMSO treated cells (MIN) to report percent of inhibition for each compound-treated well.

In this assay, the cell potency ($EC_{50}$) of each compound was determined from a ten point (1:3 serial dilution; top compound concentration of 10000 nM) titration curve using the following outlined procedure. Each well of a BD falcon collagen coated black/clear bottom 384-well plate was seeded with 4000 MCF-7 cells and allowed to attach for 5 hours. Media from cell plate was removed at 0.5 mm above the bottom of the plate and replaced with 30 μL of fresh media containing 1.2× compounds in 0.1% DMSO. Cells were treated for 3 days in 37° C. $CO_2$ incubator. On day 3, cells were fixed with Cytofix, permeabilized with 0.4% Triton-X-100/Cytofix, and washed with D-PBS without Ca/Mg. Cells were blocked with Licor Odessey blocking reagent for one hour at room temperature, followed by incubation with anti-SDMA (1:1000) antibody at 4° C. overnight. 1° antibody was removed, followed by three washings with DPBS without Ca/Mg and 0.05% Tween20. Hoechst (5 μg/ml), Cell Mask deep stain (1:2000) and Alexa488-conjugated goat anti-rabbit IgG (2 μg/mL) was added for 1 hour at room temperature. A final washing step (three washes) was performed before sealing plate for imaging on In Cell Analyzer 2200. Images from analyzer were uploaded to Columbus (at WP) for image analysis. $IC_{50}$ values were determined by 4 parameters robust fit of percent fluorescence units vs. ($Log_{10}$) compound concentrations.

| Ex. No. | Enzyme Methylation Assay ($EC_{50}\_1$, nM; $EC_{50}\_2$, nM) | TE Assay ($EC_{50}$, nM) |
|---|---|---|
| 1 | 0.27; 5 | 19 |
| 2 | 0.62; 126 | 17 |
| 3 | 47; 574 | 5440 |
| 4 | 21; 8431 | |
| 5 | 2; 890 | 2151 |
| 6 | 2; 781 | 203 |
| 7 | 3; 994 | 167 |
| 8 | 0.62; 225 | 80 |
| 9 | 0.56; 334 | 70 |
| 10 | 1; 549 | 345 |
| 11 | 0.93; 451 | 135 |
| 12 | 32; 11600 | 4644 |
| 13 | 21; 8081 | 4657 |
| 14 | 12; 4279 | 3201 |
| 15 | 23; 7231 | 2187 |
| 16 | 7; 3697 | 846 |
| 17 | 180; 34900 | 10000 |
| 18 | 0.79; 185 | 19 |

The invention claimed is:

1. A compound of formula I:

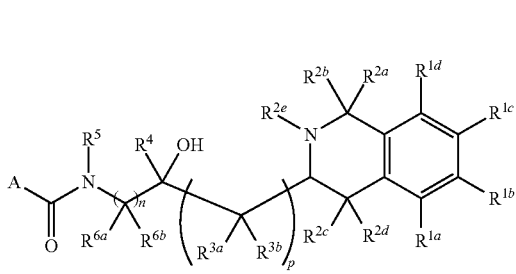

wherein:

n is 1 or 2;

p is 0 or 1;

$R^{1a}$, $R^{1b}$, $R^{1c}$ and $R^{1d}$ are independently selected from the group consisting of H, halo, $C_{1-4}$ alkoxy, $C_{1-4}$ alkyl, $C_{1-4}$ fluoroalkyl, $C_{3-4}$ cycloalkyl, NH—$C_{1-4}$ alkyl and cyano;

$R^{2a}$ and $R^{2b}$ are independently selected from the group consisting of:
(i) F;
(ii) H;
(iii) Me; and
(iv) $CH_2OH$;

$R^{2c}$ and $R^{2d}$ are independently selected from the group consisting of:
(i) F;
(ii) H;
(iii) Me; and
(iv) $CH_2OH$;

$R^{2e}$ is H or Me;

$R^{3a}$ and $R^{3b}$ are independently selected from H and Me;

$R^4$ is either H or Me;

$R^5$ is either H or Me;

$R^{6a}$ and $R^{6b}$ are independently selected from H and Me;

A is either
(i) optionally substituted phenyl;
(ii) optionally substituted naphthyl; or
(iii) optionally substituted $C_{5-12}$ heteroaryl;

wherein when $R^{2e}$ is H, at least one of $R^{1a}$, $R^{1b}$, $R^{1c}$ and $R^{1d}$ is selected from $C_{1-4}$ alkoxy, $C_{2-4}$ alkyl, $C_{1-4}$ fluoroalkyl, $C_{3-4}$ cycloalkyl, NH—$C_{1-4}$ alkyl and cyano.

2. A compound according to claim 1, wherein n is 1.

3. A compound according to claim 1, wherein p is 0.

4. A compound according to claim 1, wherein one of $R^{1a}$, $R^{1b}$, $R^{1c}$ and $R^{1d}$ is halo, $C_{1-4}$ alkoxy, $C_{1-4}$ alkyl, $C_{1-4}$ fluoroalkyl, $C_{3-4}$ cycloalkyl, NH—$C_{1-4}$ alkyl or cyano.

5. A compound according to claim 1, wherein $R^{1c}$ is methoxy.

6. A compound according to claim 1, wherein $R^{2a}$, $R^{2b}$, $R^{2c}$ and $R^{2d}$ are all H.

7. A compound according to claim 1, wherein $R^4$ is H.

8. A compound according to claim 1, wherein $R^5$ is H.

9. A compound according to claim 1, wherein $R^{6a}$ and $R^{6b}$ are both H.

10. A compound according to claim 1 which is of formula Ia:

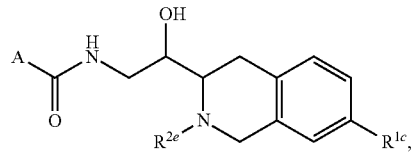

wherein $R^{1c}$ is H or methoxy and $R^{2e}$ is H or methyl, and one of $R^{1c}$ and $R^{2e}$ is not H.

11. A compound according to claim 1, which has the following stereochemistry:

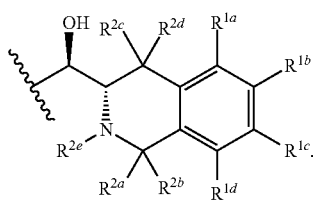

12. A compound according to claim 1, wherein the optional substituents on A are independently selected from the group consisting of: $C_{1-4}$ alkyl, $C_{1-4}$ fluoroalkyl, $C_{3-6}$ cycloalkyl, $C_{5-6}$ heteroaryl, $C_{5-6}$ heteroaryl methyl, $C_{4-6}$ heterocyclyl, $C_{4-6}$ heterocyclyl methyl, phenyl, benzyl, halo, amido, amidomethyl, acylamido, acylamidomethyl, $C_{1-4}$ alkyl ester, $C_{1-4}$ alkyl ester methyl, $C_{1-4}$ alkyl carbamoyl, $C_{1-4}$ alkyl carbamoyl methyl, $C_{1-4}$ alkylacyl, $C_{1-4}$ alkylacyl methyl, phenylcarbonyl, carboxy, carboxymethyl, ether, amino, aminomethyl, sulfonamido, sulfonamino, sulfone, sulfoxide, nitrile and nitrilemethyl and when A is phenyl, the optional substituent may also be a fused $C_{5-6}$ $N_1$-containing heterocyclic ring.

13. A compound according to claim 12, wherein A is phenyl which has 1 or 2 substituents.

14. A compound according to claim 13, wherein the substituents are selected from: $C_{1-4}$ alkyl, fluoro, chloro, bromo, acetyl, methoxy, ethoxy, —C(=O)Me, —C(=O)Et, —$CH_2$C(=O)Me, phenyl, —$CF_3$, —$CF_2$H, —CN, —$CH_2$CN, —OBn, —OPh, —$OCF_3$, —$OCF_2$H, —O—($C_6H_4$)—CN, —COOH, —$CH_2$COOH, —C(=O)OMe, —C(=O)$NH_2$, —C(=O)NMeH, —C(=O)$NMe_2$, —C(=O)$N^iPr$H, —C(=O)-piperidinyl, —C(=O)-pyrrolidinyl, —C(=O)-morpholino (which may be bridged or substituted with one or two methyl groups), —C(=O)-azetidinyl, —$CH_2$C(=O)$NH_2$, —$CH_2$C(=O)-azetidinyl, —$CH_2$C(=O)NMeH, —$CH_2$C(=O)$N^iPr$H, —$CH_2$C(=O)-pyrrolidinyl, —$CH_2$C(=O)-morpholino, —$CH_2$-morpholino, —$CH_2$-methylpiperazinyl, —$OCH_2$pyridinyl, —$OCH_2$-methyloxadiazolyl, —$CH_2$-imidazolyl, —O-tetrahydropyranyl, —$CH_2$-tetraydropyanyl, —NH-methylpyrazinyl, —$CH_2$-triazolyl, —$NHSO_2$Ph, —$NHSO_2$Me, —$SO_2$NMePh, —$SO_2NMe_2$, —$SO_2$NHEt, —$SO_2CF_3$, -γ-lactam, —$CH_2$NHC(=O)Me, —$CH_2$NHC(=O)OMe, —$CH_2$NHC(=O)$CF_3$, morpholino, —$CH_2NH_2$, —C(=O)Ph, —$OCH_2$-isoxazolyl, —NH-pyrimidinyl, pyridizinyl, pyrimidinyl, pyridinyl, pyrazolyl, methylpyrazolyl, dimethylpyrazolyl, pyrazinyl, pyridazinyl, methyloxadiazolyl, oxadiazolyl, dimethyloxadiazolyl, isoxazolyl, dimethyltriazolyl, imidazolyl, benzimidazolyl and thiadiazolyl.

15. A compound according to claim 13, wherein in the ortho position of the phenyl group there is a halo, $C_{1-4}$ alkyl, methoxy or ethoxy substituent.

16. A compound according to claim 13, wherein in the para position of the phenyl group there is an amido or amidomethyl substituent.

17. A compound according to claim 1, wherein A is a $C_{5-12}$ heteroaryl group which is either pyridinyl or pyrimidinyl.

18. A compound according to claim 17, wherein the $C_{5-12}$ heteroaryl group is unsubstituted.

19. A compound according to claim 17, wherein the $C_{5-12}$ heteroaryl group has 1 substituent.

20. A compound according to claim 19, wherein in the ortho position of a $C_6$ heteroayl group, or α-position of $C_5$ and $C_{7-12}$ heteroaryl group there is a halo or methoxy substituent.

21. A compound according to claim 19, wherein in the meta position of a $C_6$ heteroayl group, or in the β-position of a $C_5$ or $C_{7-12}$ heteroaryl group, there is an amino substituent.

22. A compound according to claim 1, wherein A is selected from phenyl with a para-amido substituent;
    phenyl with a para-amido substituent, and an ortho-ethoxy group;
    pyridyl with para ether or amino group, where the ether or amino substituent is a $C_{5-6}$ heterocyclic group, with an optional ortho-ethoxy group; and
    pyridyl with a meta ether group, where the pyridyl N is in the para position.

23. A compound according to claim 1, wherein the compound is selected from the group consisting of:
    4-(3-Oxa-8-azabicyclo[3.2.1]octane-8-carbonyl)-2-ethoxy-N—((R)-2-hydroxy-2-((S)-7-methoxy-1,2,3,4-tetrahydroisoquinolin-3-yl)ethyl)benzamide (1);
    4-(3-Oxa-8-azabicyclo[3.2.1] octane-8-carbonyl)-N—((R)-2-hydroxy-2-((S)-7-methoxy-1,2,3,4-tetrahydroisoquinolin-3-yl)ethyl)benzamide (2); and
    4-(3-Oxa-8-azabicyclo[3.2.1] octane-8-carbonyl)-2-ethoxy-N—((R)-2-hydroxy-2-((S)-2-methyl-1,2,3,4-tetrahydroisoquinolin-3-yl)ethyl)benzamide (3).

24. A pharmaceutical composition comprising a compound according to claim 1, and a pharmaceutically acceptable excipient.

* * * * *